US012703881B2

(12) United States Patent
Nappi et al.

(10) Patent No.: US 12,703,881 B2
(45) Date of Patent: Aug. 11, 2026

(54) METHOD FOR LABELING NUCLEIC ACID

(71) Applicant: CAMBRIDGE ENTERPRISE LIMITED, Cambridge (GB)

(72) Inventors: Manuel Nappi, Cambridge (GB); Alexandre Hofer, Cambridge (GB); Shankar Balasubramanian, Cambridge (GB); Matthew J. Gaunt, Cambridge (GB)

(73) Assignee: CAMBRIDGE ENTERPRISE LIMITED, Cambridge (GB)

(*) Notice: Subject to any disclaimer, the term of this patent is extended or adjusted under 35 U.S.C. 154(b) by 658 days.

(21) Appl. No.: 18/025,664

(22) PCT Filed: Sep. 14, 2021

(86) PCT No.: PCT/EP2021/075252
§ 371 (c)(1),
(2) Date: Mar. 10, 2023

(87) PCT Pub. No.: WO2022/053718
PCT Pub. Date: Mar. 17, 2022

(65) Prior Publication Data

US 2023/0416815 A1 Dec. 28, 2023

(30) Foreign Application Priority Data

Sep. 14, 2020 (GB) ..................................... 2014404

(51) Int. Cl.
*C12Q 1/68* (2018.01)
*C07D 213/61* (2006.01)
(Continued)

(52) U.S. Cl.
CPC ......... *C12Q 1/6874* (2013.01); *C07D 213/61* (2013.01); *C07D 213/75* (2013.01);
(Continued)

(58) Field of Classification Search
CPC .. C12Q 1/6886; C12Q 1/6874; C12Q 1/6818; C12Q 2527/125; C12Q 2537/164;
(Continued)

(56) References Cited

U.S. PATENT DOCUMENTS

| | | | |
|---|---|---|---|
| 10,328,256 | B1 | 6/2019 | Gliner |
| 2015/0051402 | A1 | 2/2015 | Liu et al. |
| 2019/0078132 | A1 | 3/2019 | Xiao |

FOREIGN PATENT DOCUMENTS

| | | |
|---|---|---|
| JP | 2009507036 | 2/2009 |
| WO | WO-2007028129 A1 | 3/2007 |

(Continued)

OTHER PUBLICATIONS

Cheng Li-Jie et al: "Enantioselective propargylic [1,3]-rearrangements: copper-catalyzed 0-to-N migrations toward C—N bond formation", Chemical Science, vol. 8, No. 6, Jan. 1, 2017 (Jan. 1, 2017), pp. 4299-4305, XP055881317, United Kingdom ISSN: 2041-6520, DOI: 10.1039/C7SC01042G. Retrieved from the Internet: URL: https://pubs.rsc.org/en/content/articlepdf/2017/sc/c7sc01042g>.

(Continued)

*Primary Examiner* — Jezia Riley
(74) *Attorney, Agent, or Firm* — Wilson Sonsini Goodrich & Rosati

(57) ABSTRACT

The invention provides a method for labeling a nucleic acid comprising N6-methyl adenine. The method comprises forming an alpha-amino radical on the N6-methyl group of $N^6$mAde, and capturing the alpha-amino radical with a radical acceptor comprising a nitrosopyridyl group. The presence of $N^6$mAde in a nucleic acid may then be established by detection of the labeled nucleic acid, or the labeled nucleic acid may be extracted or further modified using the label. Also provided is a method for mapping the position of (Continued)

$N^6$mAde within a target nucleic acid, and probe molecules and kits for use in the method.

16 Claims, 11 Drawing Sheets

Specification includes a Sequence Listing.

(51) Int. Cl.
*C07D 213/75* (2006.01)
*C07D 213/81* (2006.01)
*C12Q 1/6818* (2018.01)
*C12Q 1/6874* (2018.01)
*C12Q 1/6806* (2018.01)
(52) U.S. Cl.
CPC ......... *C07D 213/81* (2013.01); *C12Q 1/6818* (2013.01); *C12Q 1/6806* (2013.01)
(58) Field of Classification Search
CPC .. C12Q 1/6806; C07D 417/12; C07D 213/61; C07D 213/75; C07D 213/81
See application file for complete search history.

(56) References Cited

FOREIGN PATENT DOCUMENTS

| | | |
|---|---|---|
| WO | WO-2010037001 A2 | 4/2010 |
| WO | WO-2013017853 A2 | 2/2013 |
| WO | WO-2013090588 A1 | 6/2013 |
| WO | WO-2014083118 A1 | 6/2014 |
| WO | WO-2015124955 A1 | 8/2015 |
| WO | WO-2015145133 A1 | 10/2015 |
| WO | WO-2016016639 A1 | 2/2016 |
| WO | WO-2016034908 A1 | 3/2016 |
| WO | WO-2016063034 A1 | 4/2016 |
| WO | WO-2016063059 A1 | 4/2016 |
| WO | WO-2016079509 A1 | 5/2016 |
| WO | WO-2016170319 A1 | 10/2016 |
| WO | WO-2016189288 A1 | 12/2016 |
| WO | WO-2017039002 A1 | 3/2017 |
| WO | WO-2018211329 A2 | 11/2018 |
| WO | WO-2019064063 A1 | 4/2019 |
| WO | WO-2019239218 A2 | 12/2019 |
| WO | WO-2020026031 A2 | 2/2020 |
| WO | WO-2020194057 A1 | 10/2020 |
| WO | WO-2021072435 A2 | 4/2021 |
| WO | WO-2022023753 A1 | 2/2022 |

OTHER PUBLICATIONS

Zhang Guoqiang et al: "N6-Methyladenine DNA Modification in *Drosophila*", Cell, Elsevier, Amsterdam NL, vol. 161, No. 4, Apr. 30, 2015 (Apr. 30, 2015), pp. 893-906, XP029224288, ISSN: 0092-8674, DOI: 10.1016/J.CELL.2015.04.018.
Tao P. Wu et al: "DNA methylation on N6-adenine in mammalian embryonic stem cells", Nature, vol. 532, No. 7599, Mar. 30, 2016 (Mar. 30, 2016), pp. 329-333, XP055423560, London ISSN: 0028-0836, DOI: 10.1038/nature 17640.
Xie Li-Jun et al: "Identification of Flavin Mononucleotide as a Cell-Active Artificial N 6-Methyladenosine RNA Demethylase", Angewandte Chemie International Edition, vol. 58, No. 15, Apr. 1, 2019 (Apr. 1, 2019), pp. 5028-5032, XP055880741, ISSN: 1433-7851, DOI: 10.1002/anie.201900901 Retrieved from the Internet: URL:https://onlinelibrary.wiley.com/doi/fu ll-XML/10.1002/anie.201900901>.
Arroyo, et al., Spin Trapping and Spin Labelling Studied Using EPR Spectroscopy. C. M. Encyclopedia of Spectroscopy and Spectrometry 2189-2198 (1999).
Blanksby, et al., Bond Dissociation Energies of Organic Molecules. Accounts of Chemical Research 36:255-263 (2003).
Cibian, et al., The Relationship between Structure and Properties in Zn Complexes of Bulky N,N Diarylformamidinate N-Oxides. European Journal of Inorganic Chemistry 177-185 (2016).
Dinnocenzo, et al., Deprotonation of Tertiary Amine Cation Radicals. A Direct Experimental Approach. Journal of the American Chemical Society 111:8646-8653 (1989).
Dombrowski, et al., α—C—H Bond Dissociation Energies of Some Tertiary Amines. The Journal of Organic Chemistry 64:427-431 (1999).
Douvlataniotis, et al., No evidence for DNA N6-methyladenine in mammals. Science Advances 6: eaay3335 (2020).
Fisher, et al., Synthesis of Hindered α-Amino Carbonyls: Copper-Catalyzed Radical Addition with Nitroso Compounds. Journal of the American Chemical Society 137:11614-11617 (2015).
Fu, et al., N6-Methyldeoxyadenosine Marks Active Transcription Start Sites in Chlamydomonas. Cell 161:879-892 (2015).
Gomez-Mejiba, et al., Immuno-spin trapping of protein and DNA radicals: "Tagging" free radicals to locate and understand the redox process. Free Radical Biology and Medicine 46:853-865 (2009).
Green, et al., Polymerase Chain Reaction. Cold Spring Harbor Protocols 436:456 (2019).
Greer, et al., DNA Methylation on N6-Adenine in C. elegans. Cell 161:868-878 (2015).
Gui, et al., Practical olefin hydroamination with nitroarenes. Science 348:886-891 (2015).
Haga, et al., Luminescence Quenching of the Tris(2,2/-bipyrazine)ruthenium(II)Cation and Its Monoprotonated Complex. Inorganic Chemistry 24:1901-1906 (1985).
Hao, et al., N6-Deoxyadenosine Methylation in Mammalian Mitochondrial DNA. Molecular Cell 78 (2020).
Jeffrey, et al., O—H hydrogen bonding promotes H-atom transfer from a C—H bonds for C-alkylation of alcohols. Science 349:1532-1536 (2015).
Jia, et al., A ruthenium bisoxazoline complex as a photoredox catalyst for nitro compound reduction under visible light. Dalton Transactions 48:9949-9953 (2019).
Kalyanasundaram, et al., Photophysics, Photochemistry and Solar Energy Conversion With Tris (Bipyridyl)Ruthenium(II) and Its Analogues. Coordination Chemistry Reviews 46:159-244 (1982).
Krajete, et al., Iminohydroxamato Early and Late Transition Metal Halide Complexes—New Precatalysts for Aluminoxane-Cocatalyzed Olefin Insertion Polymerization. European Journal of Inorganic Chemistry 1740-1752 (2004).
Laarhoven, et al., Determination of Bond Dissociation Enthalpies in Solution by Photoacoustic Calorimetry. Accounts of Chemical Research 32:342-349 (1999).
Le, et al., Selective sp3 C—H alkylation via polarity-match-based cross-coupling. Nature 547:79-83(2017).
Lentini, et al., A reassessment of DNA-immunoprecipitation-based genomic profiling. Nature methods 15:499-504 (2018).
Liu, et al., Gas-Phase and Solution-Phase Homolytic Bond Dissociation Energies of H—N+ Bonds in the Conjugate Acids of Nitrogen Bases. The Journal of Organic Chemistry 61:4778-4783 (1996).
Martinez, et al., Catalytic Mechanisms of Fe(II)- and 2-Oxoglutarate-dependent Oxygenases. Journal of Biological Chemistry 290:20702-20711 (2015).
Meisel, et al., One-Electron Redox Potentials of Nitro Compounds and Radiosensitizers. Correlation with Spin Densities of Their Radical Anions. Journal of the American Chemical Society 97:5198-5203 (1975).
Mondo, et al., Widespread adenine N6-methylation of active genes in fungi. Nature Genetics 49:964-968 (2017).
Nappi, et al., Selective Chemical Functionalization at N6-Methyladenosine Residues in DNA Enabled by Visible-Light-Mediated Photoredox Catalysis. Journal of the American Chemical Society 142:21484-21492 (2020).
O'Brown, et al., Sources of artifact in measurements of 6mA and 4mC abundance in eukaryotic genomic DNA. Genomics 20:445-459 (2019).
PCT/EP2021/075252 International Search Report and Written Opinion dated Jan. 28, 2022.

(56) References Cited

OTHER PUBLICATIONS

Roberts, et al., Polarity-reversal catalysis of hydrogen-atom abstraction reactions: concepts and applications in organic chemistry. Chemical Society Reviews journal 28:25-35 (1999).
Sako, et al., N6-Substituent Effect on the Photooxidation of 2,3-0-Isopropyl ideneadenosines with a Pyrimido [ 5,4-g] pteridinetetraone N-Oxide. Chemical Evidence for the Generation and Reactivity of Adenosyl Cation Radicals. Journal of the Chemical Society 1:1801-1805 (1992).
Sanchez-Romero, et al., DNA methylation in bacteria: from the methyl group to the methylome. Current Opinion in Microbiology 25:9-16 (2015).
Schubeler, et al., Function and information content of DNA methylation. Nature 517:321-326 (2015).
Song, et al., Selective Chemical Labeling Reveals the Genome-Wide Distribution of 5-Hydroxymethylcytosine. Nature Biotechnology 29(1):68-72 (2011).
Vincent, et al., Hydrolysis and Hydrogenolysis of Formamidines: N,N-Dimethyl and N,N-Dibenzyl Formamidines as Protective Groups for Primary Amines. The Journal of Organic Chemistry 64:991-997 (1999).
White, et al., Enantioselective N-Heterocyclic Carbene-Catalyzed β-Hydroxylation of Enals Using Nitroarenes: An Atom Transfer Reaction That Proceeds via Single Electron Transfer. Journal of the American Chemical Society 136:14674-14677 (2014).
Xie, et al., Identification of Flavin Mononucleotide as a Cell-Active Artificial N 6-Methyladenosine RNA Demethylase. Angewandte Chemie International Edition 58(15):5028-5032 (2019).
Yao, et al., DNA N6-methyladenine is dynamically regulated in the mouse brain following environmental stress. Nature Communications 8:1122 (2017).
Lee, B.S. et al. Copper nitride nanoparticles supported on a superparamagnetic mesoporous microsphere for toxic-free click chemistry. Chemical communications 46.22: 3935-3937 (2010).
Liu, A. et al. Synthesis and insecticidal activity of novel nitropyridyl-based dichloropropene ethers. Journal of Agricultural and Food Chemistry 63.34:7469-7475 (2015).
Veltri, L. et al. A multicomponent palladium-catalyzed carbonylative approach to imidazopyridinyl-N, N-dialkylacetamides. Journal of Catalysis 386: 53-59 (2020).

Recovery of dsDNA (99bp) after photoredox reaction (qPCR)

SEQUENCE LISTING

```
<160> NUMBER OF SEQ ID NOS: 13

<210> SEQ ID NO 1
<211> LENGTH: 99
<212> TYPE: DNA
<213> ORGANISM: Artificial Sequence
<220> FEATURE:
<223> OTHER INFORMATION: synthetic construct

<400> SEQUENCE: 1

aacggaagca gaacagaacg aagcaagacg agcaacacga acagaacacg aaacgatgca     60

agagagcaag caagcaacgt tcgttgctgt tcgctgttg                            99
```

-continued

<210> SEQ ID NO 2
<211> LENGTH: 99
<212> TYPE: DNA
<213> ORGANISM: Artificial Sequence
<220> FEATURE:
<223> OTHER INFORMATION: synthetic construct

<400> SEQUENCE: 2
aacgaagcag aacgcagaag aagcaagacg accaacacgt acggaacacg aaacgaagca 60
tgcgccgaag caagccacgt tcggttgctg ttctgttcg 99

<210> SEQ ID NO 3
<211> LENGTH: 20
<212> TYPE: DNA
<213> ORGANISM: Artificial Sequence
<220> FEATURE:
<223> OTHER INFORMATION: synthetic construct

<400> SEQUENCE: 3
caacagcgaa cagcaacgaa 20

<210> SEQ ID NO 4
<211> LENGTH: 20
<212> TYPE: DNA
<213> ORGANISM: Artificial Sequence
<220> FEATURE:
<223> OTHER INFORMATION: synthetic construct

<400> SEQUENCE: 4
cgaacagaac agcaaccgaa 20

<210> SEQ ID NO 5
<211> LENGTH: 13
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (9)..(9)
<223> OTHER INFORMATION: n = m6a

<400> SEQUENCE: 5
cttgacagnc tag 13

<210> SEQ ID NO 6
<211> LENGTH: 41
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (31)..(31)
<223> OTHER INFORMATION: n = m6a

<400> SEQUENCE: 6
gcgcttggct ggtgggtgat tctgcaactc ngatcatgct a 41

<210> SEQ ID NO 7
<211> LENGTH: 13
<212> TYPE: DNA
<213> ORGANISM: Artificial Sequence
<220> FEATURE:
<223> OTHER INFORMATION: synthetic construct

<400> SEQUENCE: 7
cttgacagac tag 13

<210> SEQ ID NO 8
<211> LENGTH: 11
<212> TYPE: DNA
<213> ORGANISM: Artificial Sequence
<220> FEATURE:
<223> OTHER INFORMATION: synthetic construct

<400> SEQUENCE: 8
cgtactagac g 11

<210> SEQ ID NO 9
<211> LENGTH: 41
<212> TYPE: DNA
<213> ORGANISM: Artificial Sequence
<220> FEATURE:
<223> OTHER INFORMATION: synthetic construct

<400> SEQUENCE: 9
gcgcttggct ggtgggtgat tctgcaactc agatcatgct a 41

<210> SEQ ID NO 10
<211> LENGTH: 20
<212> TYPE: DNA
<213> ORGANISM: Artificial Sequence
<220> FEATURE:
<223> OTHER INFORMATION: synthetic construct

<400> SEQUENCE: 10
cgcgaaccga ccacccacta 20

<210> SEQ ID NO 11
<211> LENGTH: 30
<212> TYPE: DNA
<213> ORGANISM: Artificial Sequence
<220> FEATURE:
<223> OTHER INFORMATION: synthtic construct

<400> SEQUENCE: 11
cgcgaaccga ccacccacta agacgttgag 30

<210> SEQ ID NO 12
<211> LENGTH: 31
<212> TYPE: DNA
<213> ORGANISM: Artificial Sequence
<220> FEATURE:
<223> OTHER INFORMATION: synthetic construct

<400> SEQUENCE: 12
cgcgaaccga ccacccacta agacgttgag t 31

<210> SEQ ID NO 13
<211> LENGTH: 32
<212> TYPE: DNA
<213> ORGANISM: Artificial Sequence
<220> FEATURE:
<223> OTHER INFORMATION: synthetic construct

<400> SEQUENCE: 13
cgcgaaccga ccacccacta agacgttgag tc 32

METHOD FOR LABELING NUCLEIC ACID

The project leading to this application has received funding from the European Union's Horizon 2020 research and innovation program under the Marie Sklodowska-Curie grant agreement Nos 702462 and 789407

RELATED APPLICATIONS

This application is a national stage application of PCT/EP2021/075252, filed Sep. 14, 2021, which claims the benefit of GB 2014404.4, filed on 14 September 2020 (14 Sep. 2020), the contents of each of which are hereby incorporated by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,049 Byte ASCII (Text) file named "41794_251_ST25.TXT," created on Mar. 9, 2023.

FIELD OF THE INVENTION

The present invention relates to a method of labeling and isolating a nucleic acid containing N6-methyl adenine, and to mapping the position of N6-methyl adenine in a target nucleic acid.

BACKGROUND

Beyond the core genetic information stored in the four-letter sequence of the DNA alphabet—adenine (A), cytosine (C), guanine (G) and thymine (T), a second layer of molecular programming exists in the form of reversible chemical modifications to the canonical nucleobases—the, so called, epigenetic code. Bacteria can methylate A and C in their own genome to distinguish it from invading DNA and to control mismatch repair and genome replication (Sánchez-Romero 2015). In eukaryotes, DNA methylation was thought to only occur at C (Schübeler 2015), which has been linked to gene regulation and has stimulated significant efforts into the development of chemical methods for its detection and mapping, leading to a better understanding of its function (Hofer 2019).

N6-methyl adenine ($N^6$mAde) is a methylated nucleobase that may be present in both the DNA and RNA of organisms. The DNA nucleoside N6-methyl deoxyadenosine ($N^6$mdAdo; $N^6$mdA) may be present in the genomic and mitochondrial DNA of eukaryotes. $N^6$mdA may also be present in plants, fungi and mammals, including humans, and may play biologically important roles in gene regulation, neurobiology and disease states. The RNA nucleoside N6-methyl adenosine ($N^6$mAdo; $N^6$ mA) may also be present in the RNA of prokaryotes and eukaryotes, including in mRNA, rRNA and tRNA. $N^6$ mA in RNA may modulate gene expression and mediate cell differentiation and may also play an important role in disease states.

Methods of detecting the presence of N6-methyl adenine in nucleic acids by enrichment sequencing are often unreliable, particularly as the relative abundance of this base in DNA and RNA is low.

Antibody immunoprecipitation methods such as $m^6$dA-DIP-seq, $m^6$A-seq, $m^6$dA-CLIP-exo-seq and miCLIP/$m^6$A-CLIP are limited by the binding specificity of the antibody used. Potential unspecific binding of these antibodies to repeat regions and cap $m^6$A sites has been reported. Antibodies are also known to show biases for densely methylated regions. For these reasons, many datasets generated through this approach are questionable.

Endonuclease enzymes have also been used to detect N6-methyl adenine in RNA and DNA (m6A-REF-seq or MAZTER-seq). This approach is limited by the recognition of the endonuclease enzymes, which are only able to detect N6-methyl adenine in specific sequence contexts.

Other enzymatic methods of N6-methyl adenine detection include the use of demethylases (m6A-SEAL), deaminases (DART-seq) and methyltransferases. These methods are generally complex. Additionally, DART-seq requires transfection, methyltransferases are not selective for N6-methyl adenine, and double-stranded DNA is a poor substrate for m6A-SEAL.

Third-generation sequencing techniques including single-molecule real-time (SMRT) sequencing and Nanopore sequencing can be used to detect N6-methyl adenine. However, a very high sequencing depth is required for reliable detection due to the low signal-to-noise ratios achieved by these methods. In addition, these techniques are very expensive and are not routinely used for the sequencing of large eukaryotic genomes.

While understanding the biological roles of $N^6$mdA and $N^6$mA is still nascent and the accuracy of common detection methods have been questioned (Lentini 2018; O'Brown 2019; Douvlataniotis 2020), it is notable, from a chemical perspective, that it is the only nucleotide modification known in mammalian DNA that contains a secondary amine feature. Even though methyl groups within N-methylamines are not traditionally reactive, the exclusivity of this motif might underpin a site-selective chemical approach with which to covalently modify and manipulate $N^6$mAde. There is currently no method to covalently modify nucleic acid sequences selectively at N6-methyl adenine, to the best of our knowledge.

SUMMARY OF THE INVENTION

In general aspect the present invention provides a method for labeling a nucleic acid comprising a secondary amine structure, such as N6-methyl adenine ($N^6$mAde). The method involves site-specific chemical modification of a secondary amine structure, such as $N^6$mAde. This allows chemical modification and manipulation of the feature such as within a nucleic acid.

In some embodiments, the method includes the generation of an N6-methyl adenine radical and the reaction of the radical with a radical acceptor. The presence of $N^6$mAde in a nucleic acid may then be established either by detection of the labeled nucleic acid, or the labeled nucleic acid may be extracted or further modified using the label.

In a first aspect of the invention, there is provided a method for labeling a nucleic acid comprising N6-methyl adenine ($N^6$mAde), the method comprising:

i) forming an alpha-amino radical on the N6-methyl group of $N^6$mAde; and ii) capturing the alpha-amino radical with a radical acceptor comprising a nitrosopyridyl group (O=N-Py-).

Preferably, the alpha-amino radical is formed by contacting the nucleic acid comprising $N^6$mAde with an amine-centered radical cation to abstract a hydrogen atom from the N6-methyl group of $N^6$mAde.

The method may comprise oxidizing an amine to generate the amine-centered radical cation.

Preferably, the amine is a tertiary amine, such as a quinuclidine having the formula:

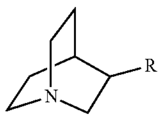

where R is selected from a hydrogen atom, a hydroxyl group, a $C_{1-6}$ alkyl group, a $C_{1-6}$ alkoxy group, a $C_{1-6}$ acyloxy group, a $C_{1-6}$ reverse ester group or a group —$C(OH)R_1R_2$ (where $R_1$ and $R_2$ are selected from $C_{1-6}$ alkyl). More preferably, R is hydrogen.

A photocatalyst may be used to oxidize the amine.

Preferably, the photocatalyst, in either the excited state or reduced form, has a reduction potential of at least +1.10 V vs SCE to at most +1.45 V vs SCE. More preferably, the photocatalyst is a transition metal photocatalyst, such as a ruthenium or iridium photocatalyst. The photocatalyst may be selected from $[Ru(phen)_3]^{2+}$ and $[Ru(bpz)_3]^{2+}$.

The radical acceptor may be a probe having the formula-(I):

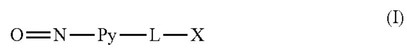

$$O{=}N—Py—L—X \quad (I)$$

where -Py- is a pyridinediyl group, -L- is a linker and —X is a label.

Preferably, —X is a click reaction partner (—$C^1$), such as a group selected from $C_{2-20}$ alkynyl, $C_{2-20}$ alkenyl, isocyanide, azido, nitrone, nitrile oxide and tetrazine. More preferably, —$C^1$ is a $C_{2-20}$ alkynyl group, such as an ethynyl group.

The probe may be formed in-situ from a precursor having the formula (II):

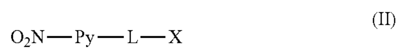

$$O_2N—Py—L—X \quad (II)$$

where -Py- is a pyridinediyl group, -L- is a linker and —X is a label.

The probe may be formed by reducing the precursor of formula (II).

Preferably, a photocatalyst is used to reduce the precursor of formula (II), such as wherein the same photocatalyst is used to reduce the precursor of formula (II) and to oxidize an amine to generate an amine-centered radical cation.

The nucleic acid may be DNA.

The method may further comprise:

iii) contacting the labeled nucleic acid with a bifunctional probe having the formula:

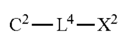

$$C^2—L^4—X^2$$

where —$C^2$ is a complementary click reaction partner, -$L^4$- is a linker and —$X^2$ is a label, such that the bifunctional probe covalently binds to the labeled nucleic acid.

Preferably, —$C^2$ is an azido group (—$N_3$). Preferably, —$X^2$ is an isolation label (—$X_{Iso}$) that binds to a binding agent, such as wherein the isolation label (—$X_{Iso}$) is biotin.

In a second aspect of the invention, there is provided a method for extracting a nucleic acid comprising $N^6$mAde from a sample, the method comprising:

i) labeling a nucleic acid comprising $N^6$mAde in the sample using the methods of the first aspect, such that the nucleic acid is covalently bound to a bifunctional probe comprising an isolation label (—$X_{Iso}$);

ii) contacting the bifunctional probe having the nucleic acid covalently bound thereto with a binding agent that binds to the isolation label (—$X_{Iso}$); and iii) extracting the binding agent having the bifunctional probe and labeled nucleic acid bound thereto from the sample.

Preferably, the binding agent comprises streptavidin. Preferably, the binding agent is immobilized on a solid support, optionally wherein the solid support is a microbead, such as a magnetic microbead.

The sample may comprise a population of nucleic acids.

The method may further comprise:

iv) contacting the binding agent with an amine nucleophile to release a nucleic acid.

Preferably, the amine nucleophile has the formula:

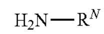

$$H_2N—R^N$$

where —$R^N$ is a $C_{1-6}$ alkyl group or —$NH_2$

In a third aspect of the invention there is provided a method for labeling a nucleic acid comprising $N^6$mAde, the method comprising:

i) contacting a nucleic acid comprising $N^6$mAde with a reaction mixture comprising:

(a) a compound comprising a nitropyridyl group ($O_2$N-Py-);

(b) a tertiary amine; and (c) a photocatalyst, such that the compound covalently attaches to the N6-methyl position of $N^6$mAde.

The preferred features of the first and second aspect apply equally to the third aspect.

In a fourth aspect of the invention, there is provided a method of labeling a nucleic acid comprising $N^6$mAde, the method comprising reacting a nucleic acid comprising $N^6$mAde with a radical acceptor comprising a nitrosopyridyl group (O═N-Py-) to produce a conjugate having the formula:

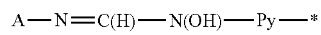

$$A—N{=}C(H)—N(OH)—Py—*$$

where -A is a 6-purinyl group, -Py- is a pyridinediyl group and * represents the attachment position with the remainder of the radical acceptor.

The preferred features of the first and second aspects apply equally to the fourth aspect.

In a fifth aspect of the invention, there is provided a compound of formula (III):

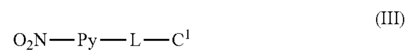

$$O_2N—Py—L—C^1 \quad (III)$$

where, -Py- is a pyridinediyl group, -L- is a linker and —$C^1$ is a click reaction partner such as a group selected from $C_{2-20}$ alkynyl, $C_{2-20}$ alkenyl or isocyanide (—$N^+{\equiv}C^-$).

In a sixth aspect of the invention, there is provided the use of a compound of formula (I) as a radical acceptor:

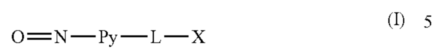

(I)

where -Py- is a pyridinediyl group, -L- is a linker and —X is a label.

In a seventh aspect of the invention, there is provided a kit comprising:

(a) a compound comprising a nitropyridyl group ($O_2N$-Py-); and (b) a tertiary amine; and (c) a photocatalyst, The preferred features of the first and second aspects apply equally to the sixth and seventh aspects.

In an eight aspect of the invention, there is provided a method for mapping the position of $N^6$mAde within a target nucleic acid, the method comprising:

i) providing a target nucleic acid comprising $N^6$mAde, wherein the target nucleic acid has a known primary nucleotide sequence;

ii) labeling the target nucleic acid using the method of the first or third aspect;

iii) amplifying the target nucleic acid to produce a population of nucleic acid fragments;

iv) sequencing the population of nucleic acid fragments to determine the base sequence of the nucleic acid fragments; and v) comparing the nucleotide sequence of the nucleic acid fragments to the nucleotide sequence of the target nucleic acid, wherein termination of the nucleotide sequence of the nucleic acid fragments indicates the position of an $N^6$mAde residue in the nucleotide sequence of the target nucleic acid.

The preferred features of the first and second aspects apply equally to the eighth aspect.

These and other aspects and embodiments of the invention are described in further detail below.

SUMMARY OF FIGURES

The present invention is described with reference to the figures listed below.

DETAILED DESCRIPTION OF THE INVENTION

Figure 1:
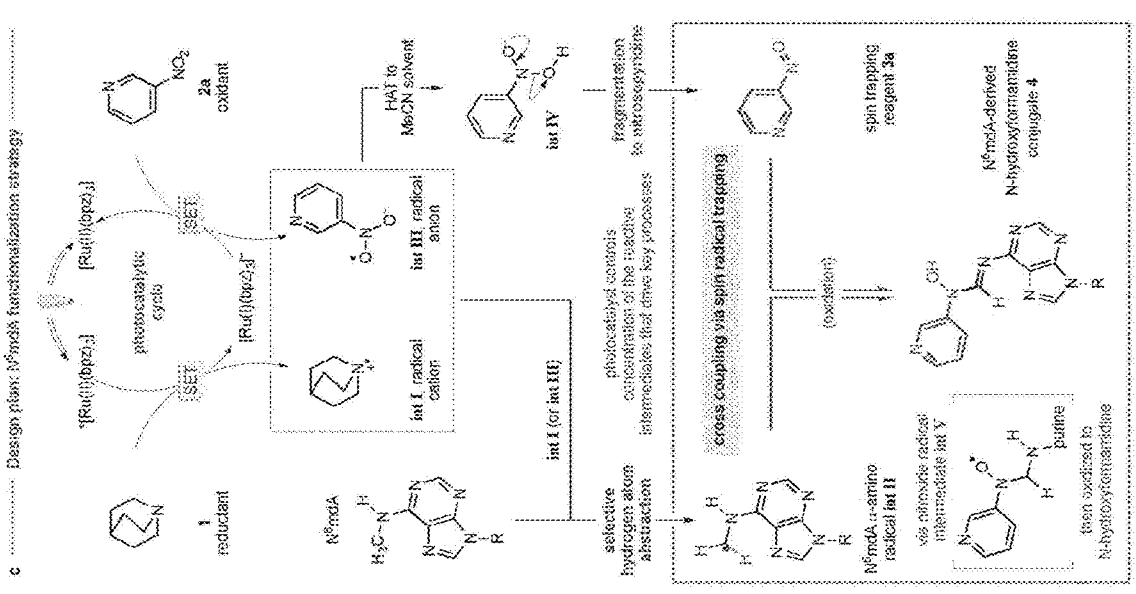
FIG. 1 is a schematic overview of the methods of the present invention. a) Shows a selective HAA at N6mdA. b) Shows a nitrosoarene-derived radical acceptor and a stable precursor nitroarene used for in-situ generation of the radical acceptor. c) Shows an overview of the photoredox-facilitated covalent modification of $N^6$mdA based on the merger of selective HAA and radical trapping via in-situ generation of nitrosoarenes.
Figure 1:
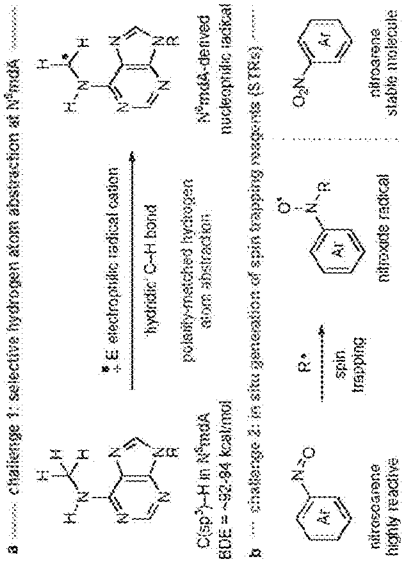

The present invention provides a method for labeling N6-methyl adenine ($N^6$mAde). An alpha-amino radical is formed on the N6-methyl group of $N^6$mAde. A radical acceptor, such as a probe of formula (I), captures the alpha-amino radical. Thus, the radical acceptor or probe covalently binds to the N6-methyl position of $N^6$mAde and thereby labels the nucleic acid comprising $N^6$mAde. Herein, the labeled nucleic acid may also be referred to as an N6-labeled nucleic acid.

Alpha-Amino Radical Formation

The method of the present invention comprises forming an alpha-amino radical on the N6-methyl group of $N^6$mAde. That is, the method comprises radicalization of the N6-methyl group of $N^6$mAde.

The alpha-amino radical may be formed by abstracting a hydrogen atom from the N6-methyl group of $N^6$mAde.

The hydrogen atom abstraction (HAA) process is preferably not an enzymatic HAA. That is, the methods of the invention preferably do not form the alpha-amino radical using an enzyme, such as an iron-centered dioxygenase.

Preferably, an electrophilic radical cation is used to abstract a hydrogen from the N6-methyl group of $N^6$mAde. That is, the method comprises contacting a nucleic acid comprising $N^6$mAde with an electrophilic radical cation to abstract a hydrogen from the N6-methyl group of $N^6$mAde and form an alpha-amino radical on the N6-methyl group of $N^6$mAde.

An electrophilic radical cation is capable of reacting with an election-rich C—H bonds to abstract a hydrogen atom and form a nucleophilic (electron-rich) radical. C—H bond positioned adjacent (alpha) to a heteroatom, such as the C—H bonds of the N6-methyl group of $N^6$mAde, are electron rich C—H bonds. As such, an electrophilic radical cation selectively forms a radical on the N6-alpha position of $N^6$mAde. That is, the electrophilic radical cation selectively abstracts a hydrogen from the N6-methyl group of $N^6$mAde and forms an alpha-amino radical on the N6-methyl group of $N^6$mAde over other alkyl C—H bonds. For example, the electrophilic radical cation may selectively abstract a hydrogen from the N6-methyl group of $N^6$mAde in place of the 5-methyl group of thymine (5-methyluracil).

Preferably, the electrophilic radical cation is an amine-centered radical cation (a nitrogen-centered radical cation). Even more preferably, a tertiary amine-centered radical cation ($R_3N^{\bullet+}$) is used.

Examples of tertiary amine-centered radical cations include the amine-centered radical cations of triarylamines and bicyclic amines.

Preferred tertiary amine-centered radical cations comprise a quinuclidine ring system. A tertiary amine-centered radical formed on the quinuclidine ring system is an electrophilic radical cation particularly well matched for the C—H bond of the N6-methyl group of $N^6$mAde.

Protonated quinuclidine has a bond dissociation energy (BDE) of 101 kcal/mol meaning that its radical cation will be sufficiently reactive to remove a hydrogen atom from the N6-methyl group of $N^6$mAde.

The quinuclidine ring system may be substituted or unsubstituted. Example of substituted quinuclidine ring systems include 3-substituted quinuclidine:

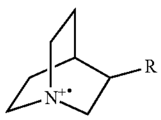

The substitution at the R position is not particularly limited. Preferably, the substituent at the R position lacks electron-rich C—H bonds in order to reduced cross-reactivity. For example, the R group may be selected from a hydroxyl group, a $C_{1-6}$ alkyl group, a $C_{1-6}$ alkoxy group, a $C_{1-6}$ acyloxy group, a $C_{1-6}$ reverse ester group or a group —$C(OH)R^1R^2$ (where $R^1$ and $R^2$ are selected from $C_{1-6}$ alkyl).

Examples of suitable ester (acyloxy) groups include —$C(O)OR^{4A}$, where —$R^{4A}$ is selected from $C_{1-6}$ alkyl.

Examples of suitable reverse ester groups —$OC(O)R^{4B}$, where —$R^{4B}$ is selected from $C_{1-6}$ alkyl, such as acetoxy (—OAc).

In a particularly preferred embodiment, the quinuclidine ring system is unsubstituted.

Alpha-Amino Radical Capture

A method of the present invention comprises capturing an alpha-amino radical formed on the N6-methyl group of $N^6$mAde using a radical acceptor, such as a probe of formula (I). The probe of formula (I) reacts with the alpha-amino radical and covalently binds to the N6-methyl position of $N^6$mAde, thereby labeling the nucleic acid comprising the $N^6$mAde. The labeled nucleic may then be detected, extracted or further modified using the probe.

Preferably, an electrophilic radical acceptor is used to capture the alpha-amino radical formed on the N6-methyl group of $N^6$mAde. An electrophilic radical acceptor is capable of reacting with a nucleophilic radical to form a new covalent bond, such as a C—C bond. The carbon-centered radical formed on the N6-methyl position of $N^6$mAde is a nucleophilic radical. As such, an electrophilic radical acceptor selectively reacts with a radical formed on the N6-methyl position of $N^6$mAde in preference to other radical species, such as the electrophilic radical cation itself.

Electrophilic radical acceptors comprising groups such as nitrone (e.g. 5,5,-dimethyl-1-pyrroline-N-oxide; DMPO) may be used to capture the alpha-amino radical formed on the N6-methyl group of $N^6$mAde.

Preferred radical acceptors comprise a nitroso group (O═N—). Particularly preferred radical acceptors comprise a nitrosoaryl group. The nitroso group of the nitrosaryl group is particularly suitable for the interception of nucleophilic carbon-centered radicals, such as the alpha-amino radical formed at the N6-methyl position of $N^6$mAde. Accordingly, in some embodiments the method may comprise capturing an alpha-amino radical formed on the N6-methyl group of $N^6$mAde with a radical acceptor comprising a nitrosoaryl group (O═N—Ar—).

The method comprises capturing an alpha-amino radical formed on the N6-methyl group of $N^6$mAde with a radical acceptor comprising a nitrosopyridyl group (O═N-Py-). The pyridine ring is advantageous as it increases the aqueous solubility of the radical acceptor.

The nitrosopyridyl group (O═N-Py-) of the radical acceptor may contain no further substituents. That is, the nitrosopyridyl group may be bound to hydrogen (H) to give a nitrosopyridine (O═N-Py).

In a preferred embodiment, the method comprises capturing an alpha-amino radical formed on the $N^6$-methyl group of $N^6$mAde with a probe of formula (I):

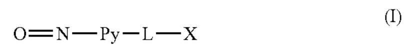

(I)

where -Py- is a pyridinediyl group, -L- is a linker and —X is a label.

The pyridinediyl group (-Py-) is a divalent pyridine (Py) group in which the two free valencies each form part of a single bond to an adjacent atom.

The pyridine ring in the pyridinediyl group (-Py-) may be substituted. The substituents are not particularly limited, provided they do not contain electron-rich C—H bonds, such as C—H bonds alpha to the pyridine ring.

For example, the pyridine ring in the pyridinediyl group (-Py-) may be independently substituted with one, two or three groups selected from the following groups:

Branched $C_{4-6}$ alkyl groups such as tert-butyl (-tBu), tert-pentyl and neo-hexyl.

$C_{5-20}$ aryl or $C_{5-20}$ heteroaryl groups.

Halo groups such as bromo (—Br).

Acyl groups $—C(=O)R^{3A}$, where $—R^{3A}$ is selected from $C_{1-6}$ alkyl and $C_{5-20}$ aryl, such as acetyl (—Ac), propionyl, tert-butyryl and benzoyl (-Bz).

Ester (acyloxy) groups $—C(O)OR^{3B}$, where $—R^{3B}$ is selected from $C_{1-6}$ alkyl and $C_{5-20}$ aryl.

Reverse ester groups $—OC(O)R^{3C}$, where $—R^{3C}$ is selected from $C_{1-6}$ alkyl and $C_{5-20}$ aryl, such as acetoxy (—OAc).

Amide (carboxamide) groups $—C(=O)NR^{3D1}R^{3D2}$, where $—R^{3D1}$ and $—R^{3D2}$ are selected from hydrogen, $C_{1-6}$ alkyl and $C_{5-20}$ aryl.

Reverse amide groups $—N(R^{3E1})C(=O)R^{3E2}$, where $—R^{3E1}$ and $—R^{3E2}$ are selected from hydrogen, $C_{1-6}$ alkyl and $C_{5-20}$ aryl, such as acetamide (—N(H)C(=O)Me).

The attachment position between the nitroso group and the pyridine ring is not particularly limited. The nitroso group may be attached to the pyridine ring at the ortho, meta or para position with respect to the pyridine nitrogen atom. Preferably, the nitroso group attaches to the pyridine ring in the meta-position with respect to the pyridine nitrogen atom.

The attachment position between the linker group and the pyridine ring and is not particularly limited. The linker group may be attached to the pyridine ring at the ortho, meta or para position with respect to the pyridine nitrogen atom. Preferably, the linker group attaches to the pyridine ring at ortho or meta position with respect to the pyridine nitrogen atom. More preferably, the pyridine ring attaches to the linker group at the meta position with respect to the pyridine nitrogen atom.

In one embodiment, the attachment position between the nitroso group and the pyridine ring is at the meta position with respect to the pyridine nitrogen atom, and the attachment position between linker group and the pyridine ring is at the ortho or meta position with respect to the pyridine nitrogen atom. That is, the nitrosopyridyl group O═N-Py- may be represented formula (IV) or (V):

formula (IV)

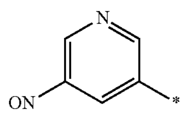

formula (V)

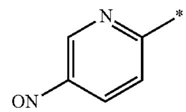

Preferably, the nitrosopyridyl group O═N-Py- is represented by formula (IV).

The label —X may comprise a detection label ($—X_{Det}$), an isolation label ($—X_{Iso}$) or a modification label ($—X_{Mod}$) as discussed for the label $—X^2$, below.

In a preferred embodiment, the label —X is a modification label ($—X_{Mod}$). That is, the method comprises capturing an alpha-amino radical formed on the N6-methyl group of $N^6$mAde with a probe having the formula:

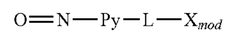

where -Py- is a pyridinediyl group, -L- is a linker and $—X_{Mod}$ is a modification label.

A modification label ($—X_{Mod}$) is any functional group suitable for further modification of the $N^6$mAde. Such functional handles are known to a person skilled in the art. Typical examples include click reaction partners, nucleophilic groups such as sulfhydryl groups or amine groups, electrophilic groups such as Michael acceptors (e.g maleimide groups) or activated esters (e.g. N-hydroxysuccinimide ester) or cross-coupling reaction partners. The modification label may be in protected form, and the protecting group may be removed as required for use of the modification label.

Preferably, the label ($—X_{Mod}$) is a click reaction partner ($—C^1$). Thus, the method comprises capturing an alpha-amino radical formed on the N6-methyl group of $N^6$mAde with a radical acceptor having the formula:

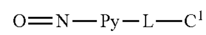

where -Py- is a pyridinediyl group, -L- is a linker and $C^1$ is a click reaction partner.

A click reaction partner may comprise any reactive group that is capable of reacting with a second reaction partner in a click reaction. Preferably, the click reaction is a bioorthogonal click reaction. That is, a click reaction that can occur inside a biological system (e.g. in the presence of other biological macromolecules) without substantially interfering with native biochemical processes within the system.

Examples of click reaction partners include groups selected from $C_{2-20}$ alkynyl, $C_{2-20}$ alkenyl, isocyanide ($—N^+{\equiv}C^-$), azido ($—N_3$), nitrone ($—R_1C{=}NR_2{}^+O^-$, where $R_2$ is not H), nitrile oxide ($—C{\equiv}N^+—O^-$) and tetrazine.

The $C_{2-20}$ alkenyl group may be a $C_{2-10}$, $C_{2-6}$ or a $C_{2-4}$ alkynyl group. The alkynyl group may be linear or branched. The carbon-carbon triple bond in the alkynyl group may be internal or terminal.

The $C_{2-20}$ alkenyl group may be a $C_{2-10}$, $C_{2-6}$ or a $C_{2-4}$ alkenyl group. The alkenyl group may be incorporated into a ring system. The alkenyl group may be linear or branched. The carbon-carbon double bond in the alkenyl group may be internal or terminal.

Preferably, the click reaction partner $—C^1$ comprises a $C_{2-20}$ alkynyl group. More preferably, the click reaction partner $—C^1$ comprises a linear $C_{2-20}$ alkynyl group. Even more preferably, the click reaction partner $—C^1$ comprises a terminal $C_{2-20}$ alkynyl group.

In one embodiment, the click reaction partner $—C^1$ is an ethynyl group. That is, preferably method comprises capturing an alpha-amino radical formed on the N6-methyl group of $N^6$mAde with a probe having the formula (VI):

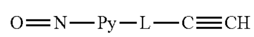

(VI)

where -Py- is a pyridinediyl group and -L- is a linker.

Optionally, the label may comprise one or more of a detection label ($—X_{Det}$), an isolation label ($—X_{Iso}$) or a modification label (—$X_{Mod}$). For example, the label may comprise a detection label such as a fluorophore for identification or localization of the $N^6$mAde, and an isolation label such as biotin for isolation of the $N^6$mAde.

The linker -L- of the probe comprises a group for connection (i.e. covalent connection) of the label (—X) to the pyridine ring. Suitable linkers are well known in the art.

Typically, the linker comprises a divalent group in which the one of the free valencies forms part of a single bond to the pyridine ring and the remaining free valency forms part of a single bond to the label (—X).

Preferably, the linker is a stable linker. That is, the linker comprises a group that is not substantially cleaved or degraded in vivo. A stable linker is typically unreactive at physiological pH, and not substantially degraded by enzymatic action in vivo.

Typically, the linker is a flexible linker. That is, the linker permits the label (—X) and pyridine ring to move relative to each other with a large degree of freedom.

Preferably, the linker -L- comprises the group:

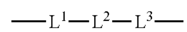

where:
- -$L^1$- is selected from a covalent bond or a $C_{8-10}$ arylene group;
- -$L^2$- is selected from an amide linkage, an ester linkage, a carbonyl linkage, an amine linkage, or an ether linkage; and
- -$L^3$- is selected from $C_{1-10}$ alkylene and $C_{1-10}$ heteroalkylene.

Preferably, the linker unit -$L^1$- is a phenylene group or a covalent bond.

Preferably, the linker unit -$L^2$- is an amide linkage —N($R^N$)—C(═O)— where $R^N$ is H or $C_{16}$alkyl, or an ester linkage —O—C(═O)—. More preferably, the linker unit -$L^2$- is an amide linkage —N($R^N$)—C(═O)—.

Preferably, the linker unit -$L^3$- is a $C_{1-10}$ alkylene group. More preferably, the linker unit -$L^2$- is a $C_{1-3}$ alkylene group. Even preferably, the linker unit -$L^2$- is a $C_{1-4}$ alkylene group. Most preferably, the linker unit -$L^2$- is a propane-1,3-diyl group.

Particularly preferred linkers include linkers having the formula (VII) to (XII):

formula (VII)

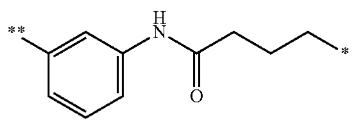

formula (VIII)

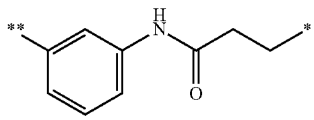

formula (IX)

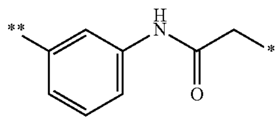

formula (X)

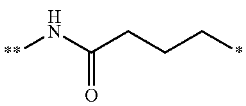

-continued formula (XI)

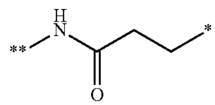

formula (XII)

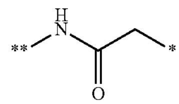

where:
- ** represents the attachment position with the pyridinediyl group (-Py-), and
- * represents the attachment position with the label (—X).

Radical Cation Formation

In a preferred embodiment, an electrophilic radical cation is used to abstract a hydrogen from the N6-methyl group of $N^6$mAde and form an alpha-amino radical on the N6-methyl group of $N^6$mAde.

The electrophilic radical cation may be formed from a precursor, for example by oxidation of the precursor. Here, the precursor for formation of the electrophilic radical cation is termed a radical precursor. That is, the method comprises oxidizing a radical precursor to form an electrophilic radical cation.

Preferably, the radical precursor is an amine, such as a tertiary amine, which is oxidized to form an amine-centered radical cation, such as a tertiary amine-centered radical cation.

Examples of tertiary amines include triarylamines and bicyclic amines.

Preferred tertiary amines comprise a quinuclidine ring system. The quinuclidine ring system may be substituted or unsubstituted. Example of substituted quinuclidine ring systems include 3-substituted quinuclidine:

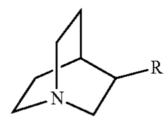

The substitution at the R position is not particularly limited, provided that it lacks electron-rich C—H bonds in order to reduced cross-reactivity. For example, the R group may be selected from a hydroxyl group, a $C_{1-6}$ alkyl group, a $C_{1-6}$ alkoxy group, a $C_{1-6}$ acyloxy group, a $C_{1-6}$ reverse ester group or a group —C(OH)$R^1R^2$ (where $R^1$ and $R^2$ are selected from $C_{1-6}$ alkyl).

In a particularly preferred embodiment, the quinuclidine ring system is unsubstituted.

Any oxidizing agent suitable for oxidizing the radical precursor to form the electrophilic radical cation may be used.

Preferably, a photocatalyst is used to oxidize the radical precursor. That is, the method comprises photocatalytically oxidizing a radical precursor to form an electrophilic radical cation.

A photocatalyst is a species that is capable of absorbing light to generate an electron-hole pair (an excited state). Single electron transfer (SET) between the radical precursor and the photocatalyst generates the electrophilic radical cation.

Preferably, the photocatalyst is a visible-light photocatalyst. That is, a photocatalyst which absorbs light in the visible range to form an excited state. This avoids the need to use ultraviolet (UV) light to excite the photocatalyst. UV light may damage or degrade nucleic acids such as RNA or DNA, which is detrimental to the labeling reaction.

Preferably, the absorption maximum for the photocatalyst is in the range 400 to 600 nm, more preferably 400 to 500 nm, and even more preferably in the range 400 to 450 nm.

The excited state of the photocatalyst is typically indicated using an asterisk (*). For example, a general photocatalyst M(0) the excitation process may be written:

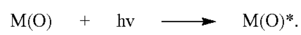

The exited state of the photocatalysts (triple excited state) may regenerate the ground state photocatalyst through either a reductive or oxidative quenching cycle.

In a reductive quenching cycle, the excited state photocatalyst first accepts an electron (is reduced) to generate a species in a lower oxidation state (the reduced form of the photocatalyst). Then, the photocatalyst donates an electron (is oxidized) to regenerate the ground state photocatalyst. For a general photocatalyst, the reductive quenching process may be written:

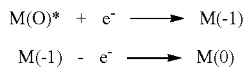

In an oxidative quenching cycle, the excited state photocatalyst first donates an electron (is oxidized) to generate a species in a higher oxidation state (the oxidized form of the photocatalyst). Then, the photocatalyst accepts an electron (is reduced) to regenerate the ground state photocatalyst. For a general photocatalyst, the reductive quenching process may be written:

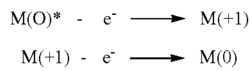

Photocatalysts may be characterized by their reduction potential against a standard reference electrode, for example the Standard Calomel Electrode (SCE). The reduction potential of each of the photocatalytic species (ground state, excited state, reduced form, oxidized form) may be known or it may be determined using standard electrochemical techniques.

Preferably, the photocatalyst (in either the excited state or reduced form) has a reduction potential of at least +1.10 V vs SCE, more preferably at least +1.15 V vs SCE, even more preferably at least +1.20 V vs SCE, and most preferably at least +1.25 V vs SCE.

Preferably, the photocatalyst (in either the excited state or reduced form) has a reduction potential of at most 1.60 V vs SCE, more preferably at most +1.55 V vs SCE, even more preferably at most +1.50 V vs SCE, and most preferably at most +1.45 V vs SCE.

Photocatalysts in which either the excited state or reduced form has a reduction potential within this range are well-matched for oxidizing a tertiary amine and generating an amine-centered radical cation, such as a quinuclidine radical cation (quinuclidine has a reduction potential of +1.10 V vs SCE).

The photocatalyst may be an organic photocatalysts or a transition metal photocatalyst.

Examples of organic photocatalysts are those based on acridinium, pyrylium, phenothiazine, phenoxazine, phenazine, phthalonitrile or flavin ring systems. Specific examples include triphenylpyrylium, 9-Mesityl-10-methylacridinium (Mes-Acr), Eosin Y, Fluorescein, riboflavin, riboflavin tetrabutyrate, riboflavin monophosphate and flavin adenine dinucleotide Preferably, the photocatalyst is a transition metal photocatalyst.

Transition metal photocatalysts typically comprise one or more ligands. The ligands may be any ligand that is suitable for stabilizing the metal in the transition metal photocatalyst.

Where two or more ligands are present, the ligands may be identical (homoleptic) or different (heteroleptic).

Example ligands for transition metal photocatalysts include those based on bipyridine ring systems, phenylpyridine ring systems, bipyrimidine ring systems, bipyrazine ring systems, phenanthroline ring systems and triphenylene ring systems.

Each ligand ring system may be substituted or unsubstituted. Typically substitutions include $C_{1-6}$ alkyl, $C_{1-3}$ haloalkyl, halo, and $C_{1-3}$ alkoxy.

Examples of phenylpyridine ligands include 2-phenylpyridine (ppy), 2-(4-fluorophenyl) pyridine (p-Fppy), 2-(4-trifluoromethylphenyl)pyridine (p-$CF_3$ppy), 4-tert-butyl-2-(4-fluorophenyl)pyridine (p-F(tBu)ppy), 2-(2,4-difluorophenyl)pyrdine (dFppy), 4-tertbutyl-2-(2,4-difluorophenyl)pyridine (dF(t-Bu)ppy), 2-(2,4-difluorophenyl)-5-(trifluoromethyl)pyridine (dF($CF_3$)ppy), 2-(2,4-difluorophenyl)-5-fluoro-pyridine (dF(F)ppy), 2-(2,4-difluorophenyl)-5-methyl-pyridine (dF(Me)ppy), 2-(2,4-difluorophenyl)-5-methoxy-pyridine (dF(OMe)ppy), 2-(2-fluoro-4-(trifluoromethyl)phenyl)-5-(trifluoromethyl) pyridine (F$CF_3$($CF_3$)ppy), 4-methyl-2-(p-tolyl)pyridine (Me (Me)ppy) and 2-(4-fluorophenyl)-5-methyl-pyridine (p-F (Me)ppy).

Examples of bipyridine ligands include 2,2'-bipyridine (bpy), 4,4'-dimethyl-2,2'-bipyridine (dmbpy), 4,4'-di-tert-butyl-2,2'-bipyridine (dtbbpy), 4,4'-bis(trifluoromethyl)-2,2'-bipyridine (4,4'-d$CF_3$bpy), 5,5'-bis(trifluoromethyl)-2,2'-bipyridine (5,5'-d$CF_3$bpy).

Examples of phenylpyridine ligands include 2-(2,4-difluorophenyl)-5-fluoropyridine, 2-(2,4-difluorophenyl)-5-methoxypyridine, 2-(2,4-difluorophenyl)-5-methylpyridine, 2-(2,4-difluorophenyl)-5-(trifluoromethyl)pyridine, 2-(4-fluorophenyl)-5-methylpyridine and 2-[2-Fluoro-4-(trifluoromethyl)phenyl]-5-(trifluoromethyl)pyridine.

Examples of bipyrimidine ligands include 2,2'-bipyrimide (bpm), Examples of bipyrazine ligands include 2,2'-bipyrazine (bpz).

Examples of phenanthroline ligands include 1,10-phenanthroline (phen), 1,4,5,8-tetraazaphenanthrene (tap) and dipyridophenazine (dppz).

Examples of triphenylene ligands include 1,4,5,8,9,12-hexaazatriphenylene (hat).

Examples of transition metal photocatalysts are those comprising ruthenium (Ru) or iridium (Ir).

Specific examples of ruthenium photocatalysts include $[Ru(bpy)_3]^{2+}$, $[Ru(phen)_3]^{2+}$, $[Ru(bpm)_3]^{2+}$, $[Ru(bpz)_3]^{2+}$, $[Ru(4,4'\text{-}dCF_3bpy)_3]^{2+}$, $[Ru(dmbpy)_3]^{2+}$ and $[Ru(dtbbpy)_3]^{2+}$.

Examples of iridium photocatalysts include $[Ir(ppy)_3]$, $[Ir(dFppy)_3]$, $[Ir(p\text{-}Fppy)_3]$, $[Ir(p\text{-}F(Me)ppy)_2(dtbbpy)]^+$, [Ir (Me(Me)ppy)$_2$(dtbbpy)]$^+$, [Ir(FCF$_3$(CF$_3$)ppy)$_2$(dtbbpy)]$^+$, [Ir(ppy)$_2$(dtbbpy)]+, [Ir(dFppy)$_2$(dtbbpy)]+, [Ir(dF(Me)ppy)$_2$(dtbbpy)]$^+$, [Ir(dF(Me)ppy)$_2$(4,4'-dCF$_3$bpy)]$^+$, [Ir(dF(F)ppy)$_2$(dtbbpy)]$^+$.

Preferably, the transition metal photocatalyst is a ruthenium photocatalyst.

More preferably, the transition metal photocatalyst is selected from [Ru(phen)$_3$]$^{2+}$ and [Ru(bpz)$_3$]$^{2+}$. Most preferably, the transition metal photocatalyst is [Ru(phen)$_3$]$^{2+}$.

Photocatalysts (including transition metal photocatalysts) typically comprise one or more counterions. The counterion may be any counterion that is suitable for stabilizing the photocatalyst.

Typically, the counterion is negatively charges. That is, typically the counterion is an anion. Typical examples of anions include inorganic anions such as halo, borate and phosphate.

Typical inorganic anions include chlorate ($Cl^-$), tetrafluoroborate $(BF_4)^-$ and hexafluorophosphate $(PF_6)^-$.

Optionally, the transition metal photocatalyst may be a hydrate. That is, the transition metal catalyst may contain water ($H_2O$).

Preferably the photocatalyst is a homogenous photocatalyst. That is, the photocatalyst exists in the same phase as the reactants. Typically, the photocatalyst is soluble in an 80% aqueous solution, such as an 85% or 90% aqueous solution. Aqueous solutions are preferred for solubility of nucleic acids.

The aqueous solubility of the photocatalysts may be know, or it may be determined using standard techniques. The metal and ligand system can be selected to adjust the aqueous solubility of the system.

In-Situ Probe Formation

In some embodiments, the method of the present invention comprises forming the radical acceptor in-situ from a precursor, such as a precursor of formula (II):

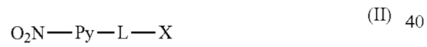

(II)

where -Py- is a pyridinediyl group, -L- is a linker and —X is a label as set out for the probe of formula (I).

The group O$_2$N— may be referred to as a nitro group. Generating the nitrosopyridine in situ from a nitropyridine precursor reduces non-radical side reactions which may occur if a large quantity of the nitrosopyridine is added at the start of the reaction.

The nitro group of the nitropyridine may be converted to a nitroso group (O═N—) such as that found in the probe of formula (I) by reduction. That is, the method may comprise reducing a precursor of formula (II) to form a probe of formula (I).

Any reducing agent suitable for reducing the precursor to form the radical acceptor may be used in the reaction.

Preferably, the nitropyridine (O$_2$N-Py-) may be reduced to the nitrosopyridine (O═N-Py-) using a photocatalyst. Suitable photocatalysts for the reduction of the nitropyridine to the nitrosopyridine include those photocatalysts used in the formation of the electrophilic radical cation. Preferably, the same photocatalyst used in the formation of the electrophilic radical cation is also used to reduce the nitropyridine to the nitrosopyridine.

Additives

The method of the present invention comprises labeling a nucleic acid comprising N6-methyl adenine. In some embodiments, the method is carried out using an additive, such as an activated alkene. The additive may be present during each of the method steps (alpha-amino radical formation and alpha-amino radical capture, and if present radical cation formation and in-situ probe formation). Typically, the additive is present in the reaction mixture during the labeling reaction.

Preferably, the additive is an activated alkene. Activated alkenes include alkenes in which the carbon-carbon double bond is conjugated to an electron-withdrawing group (EWG) and/or an electron-donating group (EDG).

Suitable electron-withdrawing groups include acyl groups —C(═O)R, where —R is selected from $C_{1-6}$ alkyl and $C_{5-20}$ aryl, such as acetyl (—Ac), propionyl, tert-butyryl and benzoyl (-Bz); ester (acyloxy) groups —C(O)OR, where —R is selected from $C_{1-6}$ alkyl and $C_{5-20}$ aryl; and amide (carboxamide) groups —C(═O)NR$^1$R$^2$, where —R$^1$ and —R$^2$ are selected from hydrogen, $C_{1-6}$ alkyl and $C_{5-20}$ aryl.

Suitable electron-donating groups include reverse ester groups —OC(O)R, where —R is selected from $C_{1-6}$ alkyl and $C_{5-20}$ aryl, such as acetoxy (—OAc); and reverse amide groups —N(R$^1$)C(═O)R$^2$, where —R$^1$ and —R$^2$ are selected from hydrogen, $C_{1-6}$ alkyl and $C_{5-20}$ aryl, such as acetamide (—N(H)C(═O)Me).

Preferably, the additive is N-acetyl dehydroalanine methyl ester (Ac-Dha-Me).

Further Aspects

In some aspects of the invention, there is provided a method for labeling a nucleic acid comprising N$^6$mAde, the method comprising:

i) contacting a nucleic acid comprising N$^6$mAde with a reaction mixture comprising:
   (a) a compound comprising a nitropyridyl group (O$_2$N-Py-);
   (b) a tertiary amine; and
   (c) a photocatalyst, such that the compound covalently attaches to the N6-methyl position of N$^6$mAde.

Preferably, the compound comprising a nitropyridyl group is a precursor of formula (II):

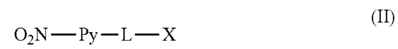

(II)

where -Py- is a pyridinediyl group, -L- is a linker and —X is a label.

Preferences for each of the components of the precursor of formula (II) (-Py-, -L-, —X) are the same as those for the probe of formula (I) as set out above.

Preferences for the tertiary amine are the same as those set out for the tertiary amine, above.

Preferences for the photocatalyst are the same as those set out for formation of the electrophilic radical cation, above.

Typically, the method comprises irradiating the reaction mixture, such as irradiating the reaction mixture with visible light. Preferably, the method comprises comprising irradiating the reaction mixture with visible light in the range 400 to 600 nm, more preferably 400 to 500 nm, and even more preferably in the range 400 to 450 nm.

The reaction mixture may contain additional components, such as solvents, as is common in the art. Particularly preferred solvents include water-acetonitrile mixtures, such as 8:1 or 9:1 water:acetonitrile.

The reaction mixture may contain additives, such as an activated alkene. Preferred additives are set out above, and include N-acetyl dehydroalanine methyl ester (Ac-Dha-Me).

N6-Methyl Adenine

The method of the present invention comprises labeling a nucleic acid comprising $N^6$mAde. Typically, the $N^6$mAde is contained within a nucleoside. Nucleosides comprising $N^6$mAde include ribonucleoside such as N6-methyl adenosine ($N^6$mAdo; $N^6$ mA) and deoxyribonucleosides such as N6-methyl deoxyadenosine ($N^6$mdAdo; $N^6$mdA). Typically, the $N^6$mAde is contained within a nucleotide. Nucleotides comprising $N^6$mAde include N6-methyl adenosine triphosphate ($N^6$mATP), N6-methyl deoxyadenosine triphosphate ($N^6$mdATP) and the mono- and di-phosphate versions.

In some embodiments, the $N^6$mAde may be contained within a nucleic acid. A nucleic acid is a polymer comprising two or more nucleotide units. The nucleic acid may be a natural nucleic acid, such as DNA or RNA, or it may be a nucleic acid analogue, such as a peptide nucleic acid (PNA), a phosphorodiamidate morpholino oligomer (PMO), a locked nucleic acid (LNA), a glycol nucleic acid (GNA) or a threose nucleic acid (TNA). The $N^6$mAde may be contained within a mixed nucleic acid comprising any of these elements.

A nucleic acid containing $N^6$mAde may contain one or more $N^6$mAde residues i.e. at least one nucleobase is $N^6$mAde. For example, a nucleic acid may contain 1, 2, 3, 4, 5 or more $N^6$mAde. One or more $N^6$mAde residues within a nucleic acid may be labeled using the methods described herein.

The method may comprise labeling $N^6$mAde within a sample. The sample may comprise a population of nucleic acids. The population may comprise one or more nucleic acids comprising $N^6$mAde. One or more nucleic acids comprising $N^6$mAde in the population may be labeled using the methods described herein.

The nucleic acids in the population may be single-stranded, double-stranded or a mixture of single and double-stranded nucleic acids. For example, cellular nucleic acids, such as cellular genomic DNA, may be double-stranded and cell-free nucleic acids, such as cfDNA, may be a mixture of single and double-stranded nucleic acids.

Preferably the nucleic acids in the population are DNA molecules, such as plasmids, synthetic DNA, viral DNA, genomic DNA preferably mammalian or human genomic DNA, and cell-free circulating DNA (cfDNA).

In other embodiments, the nucleic acids may be RNA molecules, such as genomic RNA (e.g. mammalian, plant or viral genomic RNA), mRNA, tRNA, rRNA and non-coding RNA. Genomic RNA may include mammalian, plant or viral genomic RNA.

The nucleic acids in the population may be 10 bases to 50 kbases in length, such as 20 to 3000 bases in length. Nucleic acids isolated from cellular sources may be greater than 1000 bases in length and may be fragmented, for example by sonication, for use as described herein. In some embodiments, the choice of the sequencing technique may determine the size of the nucleic acids in the population. For example, nucleic acids of 100-1000 bases may be compatible with Illumina sequencing.

In some preferred embodiments, the nucleic acids in the population may be mammalian, preferably human nucleic acids.

A method described herein may comprise isolating a population of nucleic acids from a sample. For example, the population of nucleic acids may be isolated from a sample of intact or disrupted cells or cellular material, such as mammalian cells, preferably human cells. Suitable samples include isolated cell and tissue samples, such as biopsies, including solid tissue or tumour biopsies. In some embodiments, the sample may be obtained from a formalin fixed paraffin embedded (FFPE) tissue sample or other stored sample of cellular material.

The sample may be obtained from an individual, preferably a human individual, for example a patient having or suspected of having a disease condition, such as cancer; or a healthy or at risk individual for health monitoring or assessment; or a patient undergoing treatment to assess response to a drug.

Methods of extracting and isolating genomic DNA from samples of cells are well-known in the art. For example, genomic DNA may be isolated using any convenient isolation technique, such as phenol/chloroform extraction and alcohol precipitation, caesium chloride density gradient centrifugation, solid-phase anion-exchange chromatography and silica gel-based techniques.

Whole genomic DNA isolated from cells obtained from a sample may be used directly as a population of nucleic acids as described herein, after isolation or may be subjected to further preparation steps before labeling with a probe as described herein.

For example, the genomic DNA may be fragmented, for example by sonication, shearing or endonuclease digestion, to produce genomic DNA fragments. The whole or a fraction of the genomic DNA may be used as described herein. Suitable fractions of genomic DNA may be based on size or other criteria.

Suitable populations of nucleic acids may include human genomic DNA, for example from tissue samples and human cell lines, and genomic DNA from model organisms such as *C. elegans*, yeast, bacteria, such as *E. coli*, plants, such as *Arabidopsis thaliana* and mammalian models, such as mouse.

Suitable populations of nucleic acids may also include genomic DNA from cancer cells or tumours, xenografts and other cancer models, cell-free plasma DNA, and single-cell DNA.

Following fractionation, denaturation, adaptation and/or other preparation steps, the population of nucleic acids may be optionally further purified, and provided in a suitable form for reaction with the probe as described herein. For example, the population of nucleic acids may be in aqueous solution in the absence of buffers before treatment as described herein.

Conjugate

The reaction between the nitroso group of the radical acceptor and the alpha-amino radical results in the formation of an N-hydroxyformamidine linkage (—N═C(H)—N(OH)—):

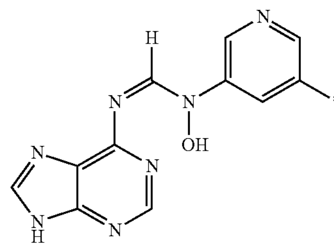

where * represents the attachment position with the remainder of the probe.

In some aspects of invention, there is provided a method of labeling a nucleic acid comprising $N^6$mAde, the method comprising reacting a nucleic acid comprising $N^6$mAde with a radical acceptor comprising a nitrosopyridyl group (O═N-Py-) to produce a conjugate having the formula:

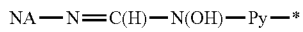

where NA is a nucleic acid, -Py- is a pyridinediyl group and * represents the attachment position with the remainder of the radical acceptor.

Preferably, the radical acceptor is a probe of formula (I). In such cases, the method produces a conjugate having the formula:

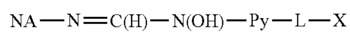

where NA is a nucleic acid, -Py- is a pyridinediyl group, L is a linker and X is a label.

Preferences for each of the components of the probe of formula (I) (-Py-, -L-, —X—) are set out above.

Optionally, the conjugate may be produced in the presence of an electrophilic radical cation, such as an amine-centered radical cation. Suitable amine-centered radical cations and suitable methods for producing the amine-centered radical cations are as described above.

Optionally, the probe of formula (I) may be formed in-situ from a precursor of formula (II). Suitable method for formation of the probe of formula (I) are as described above.

Probe Removal

The method of the present invention comprises labeling a nucleic acid comprising N6-methyl adenine. In some embodiments, the method comprises removing the label from the labeled nucleic acid.

The reaction between the nitroso group of the probe and the alpha-amino radical at the N6-methyl position of $N^6$mAde results in the formation of an N-hydroxyformamidine linkage (—N═C(H)—N(OH)—). The electrophilic nature of the N-hydroxyformamidine linkage formed between the N6-methyl group of $N^6$mAde and the radical acceptor makes it susceptible to cleavage by nucleophiles such as hydrazine ($N_2H_2$). Cleavage using such nucleophiles provides a rapid and mild method for releasing N6-hydrazonomethyl adenine, and avoids potential degradation of the sample.

Thus, the method may comprise contacting the labeled nucleic acid with a nucleophile, such as an amine nucleophile. Preferred amine nucleophiles include primary nucleophiles. Examples of primary amine nucleophiles include compounds having the formula:

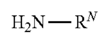

where —$R^N$ is a $C_{1-6}$ alkyl group or —$NH_2$

Preferably, the nucleophile is hydrazine. The hydrazine may be aqueous hydrazine.

Further Modification

The method of the present invention comprises labeling a nucleic acid comprising N6-methyl adenine. In some embodiments, the method comprises further modifying the labeled nucleic acid.

In some embodiments, the radical acceptor comprises a modification label (—$X_{Mod}$). This allows the labeled nucleic acid to be further modified by contacting the labeled nucleic acid with a second molecule that can covalently bind to the modification label.

Molecules that can covalently bind to the modification label can be selected by the person skilled in the art. Typically, they include molecules containing a click reaction partner, a sulfhydryl group, a maleimide group, an amine group or an activated ester, such as an N-hydroxysuccinimide ester.

A modification label comprising a sulfhydryl or maleimide group may react with a molecule comprising the other of the sulfhydryl or maleimide group to form a 3-thiosuccinimidyl ether linkage. A modification label comprising an amine group or an activated ester, such as N-hydroxysuccinimide ester, may react with a molecule comprising the other of the amine group or the activated ester to form an amide linkage. A modification label comprising a click reaction partner may react with a molecule comprising a second (complementary) click reaction partner in a click reaction.

In a preferred embodiment, the method may comprise capturing an alpha-amino radical formed on the N6-methyl group of $N^6$mAde with a probe having the formula:

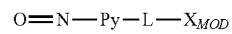

where -Py- is a pyridinediyl group, -L- is a linker and —$X_{Mod}$ is a modification label.

In such cases, the method may further comprise contacting the labeled nucleic acid with a bifunctional probe having the formula:

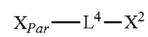

where —$X_{Par}$ is a partner group, -$L^4$- is a linker and —$X^2$ is a label, such that the partner group reacts with the modification label to covalently bind the bifunctional probe to the labeled nucleic acid.

In particularly preferred embodiment, the method may comprise capturing an alpha-amino radical formed on the N6-methyl group of $N^6$mAde with a probe having the formula:

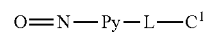

where -Py- is a pyridinediyl group, -L- is a linker and $C^1$ is a click reaction partner.

In such cases, the method may further comprise contacting the labeled nucleic acid with a bifunctional probe having the formula:

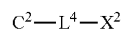

where —$C^2$ is a complementary click reaction partner, -$L^4$- is a linker and —$X^2$ is a label, such that the click reaction partners react to covalently bind the bifunctional probe to the labeled nucleic acid.

The click reaction partner —$C^2$ may comprise any reactive group that is capable of reacting with the click reaction partner —$C^1$ in a click reaction. Preferably, the click reaction is a bioorthogonal click reaction. That is, a click reaction that can occur a biological system (e.g. in the presence of other biological macromolecules) without substantially interfering with native biochemical processes within the system.

Examples of click reaction partners include selected from $C_{2-20}$ alkynyl, $C_{2-20}$ alkenyl, isocyanide (—$N^+$≡$C^-$), azido (—$N_3$), nitrone (—$R_1C$≡$NR_2{}^+O^-$, where $R_2$ is not H), nitrile oxide (—C≡$N^+$—$O^-$) and tetrazine.

Preferably, the click reaction partner —$C^2$ may comprise a group selected from azido (—$N_3$), nitrone (—$R_1C$═$NR_2{}^+$ $O^-$) where $R_2$ is not H), nitrile oxide (—C≡$N^+$—$O^-$) or tetrazine.

Preferably, the click reaction partner —$C^2$ comprises an azido group (—$N_3$). That is, preferably the method comprises contacting the labeled nucleic acid with a bifunctional probe having the formula (XIII):

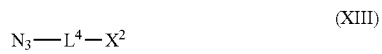

(XIII)

where $L^4$- is a linker and —$X^2$ is a label, such that the bifunctional probe covalently binds to the labeled nucleic acid.

Where the click reaction partner —$C^1$ comprises an alkynyl group (C≡C), the click reaction partner —$C^1$ may react with a click reaction partner —$C^2$ comprising an azido group (—$N_3$) through an azide-alkyne cycloaddition (AAC), for example a copper (I)-catalyzed azide-alkyne cycloaddition (CuAAC) or a strain-promoted azide-alkyne cycloaddition (SPAAC). In such cases, the product of the reaction between the two click reaction partners —$C^1$ and —$C^2$ is a 1,2,3-triazole moiety.

Where the click reaction partner $C^1$ comprises an alkyne group (C≡C), the click reaction partner $C^1$ may react with a click reaction partner $C^2$ comprising a nitrone group (—$R_1C$═$NR_2{}^+O^{--}$ where $R_2$ is not H) through a 1,3-dipolar cycloaddition. In such cases, the product of the reaction between the two click reaction partners $C^1$ and $C_2$ is an isoxazoline moiety.

Where the click reaction partner —$C^1$ comprises an alkene (C═C) such as norbornene, the click reaction partner $C^1$ may react with a click reaction partner —$C^2$ comprising a nitrile oxide group (—C═$N^+$—$O^-$) through a 1,3-dipolar cycloaddition. In such cases, the product of the reaction between the two click reaction partners —$C^1$ and —$C_2$ is an isoxazole moiety.

Where the click reaction partner —$C^1$ comprises an alkene (C═C) such as trans-cyclooctene, the click reaction partner —$C^1$ may react with a click reaction partner —$C^2$ comprising a tetrazine group through an inverse-electron demand Diels Alder reaction followed by a retro-Diels Alder reaction. In such cases, the product of the reaction between the two click reaction partners —$C^1$ and —$C_2$ is a dihydropyridazine moiety Alternatively, click reaction partner —$C^1$ comprising an isocyanide moiety (—$N^+$≡$C^{--}$) may react with a click reaction partner —$C^2$ comprising a tetrazine through a [4+1] cycloaddition followed by a retro-Diels Alder reaction. In such cases, the product of the reaction between the two click reaction partners —$C^1$ and —$C^2$ is a pyrazole moiety.

Optionally, the method may comprise reacting the labeled nucleic acid with the bifunctional probe and copper, such as a copper (I) salt. Suitable copper (I) salts may be use directly. Examples of copper (I) salts that may be used directly include cuprous bromide (CuBr) and cuprous iodide (CuI). Alternatively, suitable copper (I) salts may be generated in situ by reduction of copper (II) salts. Example copper (II) salts include copper sulfate ($CuSO_4$) or copper acetate ($Cu(OAc)_2$). Example reducing agents include sodium ascorbate.

The linker -$L^4$- of the bifunctional probe comprises a group for connection (i.e. covalent connection) of the click reaction partner —$C^2$ to the isolation label (—$X_{Iso}$). Suitable linkers are well known in the art.

Typically, the linker comprises a divalent group in which the one of the free valencies forms part of a single bond to the click reaction partner —$C^2$ and the remaining free valency forms part of a single bond to the isolation label (—$X_{Iso}$).

Preferably, the linker is a stable linker. That is, the linker comprises a group that is not substantially cleaved or degraded in vivo. A stable linker is typically unreactive at physiological pH, and not substantially degraded by enzymatic action in vivo.

Typically, the linker is a flexible linker. That is, the linker permits the click reaction partner —$C^2$ and isolation label ($X_{Iso}$) to move relative to each other with a large degree of freedom.

Typical linkers comprise groups selected from alkylene, heteroalkylene, cycloalkylene, heterocycloalkylene, arylene and heteroarylene. Mixed linkers comprising different groups in covalent connection, such as alkylene-arylene (aralkylene) and heteroalkylene-arylene, may be permitted.

Preferred linkers comprise groups selected from alkylene and heteroalkylene, such as $C_{2-12}$ alkylene and $C_{2-12}$ heteroalkylene groups. More preferred linkers comprise heteroalkylene groups. Even more preferred linkers comprise polyalkylene glycol groups. Most preferred linkers comprise polyethylene glycol (PEG) groups.

The linker may vary in length. Typically, the linker contains two or more repeated units. Typically, the linker contains at most eight repeat units. That is, the linker may be represented as:

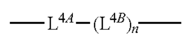

where:

-$L^{4A}$- is $C_{1-4}$ alkylene;

-$L^{4B}$- is $C_{1-4}$ heteroalkylene; and n is 0 to 8.

Preferably, n is between 0 and 6. More preferably, n is between 2 and 4. Even more preferably n is 3.

Preferably -$L^{4A}$- is $C_{1-3}$ alkylene. More preferably, -$L^{4A}$- is ethylene.

Preferably -$L^{4B}$- is a $C_{1-4}$ alkylene ether group. Examples of $C_{1-4}$ alkylene ether groups include methylene glycol (—$CH_2O$—) ethylene glycol (—$CH_2CH_2O$—), propylene glycol (—$CH_2CH_2CH_2O$—) and tetramethylene glycol (—$CH_2CH_2CH_2CH_2O$—). More preferably, -$L^{4B}$- is ethylene glycol (—$CH_2CH_2O$—).

The label $X^2$ may comprise a detection label (—$X_{Det}$), an isolation label (—$X_{Iso}$) or a modification label (—$X_{Mod}$).

A detection label (—$X_{Det}$) is group suitable for detection of the $N^6$mAde. Typical detection labels include light-sensitive groups such as a chromophore, a fluorescent or a phosphorescent label; or a radiolabel. Such labels are detectable by standard experimental techniques, such as spectroscopic techniques.

An isolation label ($—X_{Iso}$) is a group suitable for isolation of the $N^6$mAde. For example, isolation by contacting the labeled nucleic acid with a binding agent that binds to the isolation label. Typical isolation labels include binding groups, such as affinity tags for pull-down assays. Examples of such binding groups include a GST-tag, a myc-tag, a FLAG-tag and biotin.

A modification label ($—X_{Mod}$) is any functional group suitable for further modification of the labeled nucleic acid. Typical modification labels are set out for the probe of formula (I), above.

Preferably, the label $—X^2$ comprises an isolation label ($—X_{Iso}$). That is, preferably the method comprises contacting the labeled nucleic acid with a bifunctional probe having the formula:

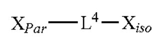

where $—X_{Par}$ is a partner group, $-L^4-$ is a linker and $—X_{Iso}$ is an isolation label, such that the partner group reacts with the modification label to covalently bind the bifunctional probe to the labeled nucleic acid.

Incorporation of an isolation label into the labeled nucleic acid permits isolation of nucleic acids comprising $N^6$mAde.

Preferably, the isolation label is biotin.

Extraction

The method of the present invention comprises labeling a nucleic acid comprising N6-methyl adenine. In some embodiments, the method comprises isolating the labeled nucleic acid.

In some embodiments, the radical acceptor probe comprises an isolation label ($—X_{Iso}$). In other embodiments, a nucleic acid labeled with a modification label ($—X_{Mod}$) is further modified by reaction with a bifunctional probe containing an isolation label ($—X_{Iso}$). In either case, the labeled nucleic acid may be isolated by contacting the labeled nucleic acid with a binding agent that binds to the isolation label.

Typically, the binding agent selectively binds to the isolation label. For example, the binding agent preferentially binds to a nucleic acid comprising the isolation label over a nucleic acid lacking the isolation label. Suitable binding agents are known in the art.

Typical binding agents include biotin-binding proteins such as streptavidin, avidin, anti-biotin antibody or neutravidin (which binds biotin); glutathione (which binds a GST-tag); and antibodies (which bind epitope tags such as myc- and FLAG-).

Preferably, the binding agent is streptavidin.

The binding agents may be immobilized on a solid support. A solid support is an insoluble, non-gelatinous body which presents a surface on which the capture molecule can be immobilized for capture of the labeled nucleic acid. Examples of suitable supports include glass slides, microwells, membranes, microbeads or nanoparticles. The support may be in particulate or solid form, including for example a plate, a test tube, bead, a ball, filter, fabric, polymer or a membrane. The binding agents may be, for example, be fixed to an inert polymer, a 96-well plate, or to a stationary phase used in chromatography. The immobilization of binding agents to the surface of a solid support is well-known in the art. In some embodiments, the solid support itself may be immobilized. For example, microbeads may be immobilized on a second solid surface. In preferred embodiments, the solid support is a microbead, such as a magnetic microbead.

In some embodiments, the labeled nucleic acid may be extracted from a sample. In such cases, the method comprises extracting the immobilized binding agents having the labeled nucleic acid bound thereto from the sample. Suitable methods for extraction are known in the art and include filtration, centrifugation or, where magnetic microbeads are used, by using a magnet.

Following extraction, the immobilized binding agents having the labeled nucleic acid bound thereto may be washed. Washing removes sample components that are not selectively bound to the binding agent. For example, unlabeled nucleic acid or other sample components.

Following isolation, the labeled nucleic acid may be released from the immobilized binding agent. Methods for releasing bound substrates are well known in the art.

As noted above, the probe may be removed using a nucleophile, such as an amine nucleophile. In a preferred embodiment, the labeled nucleic acid may be released from the immobilized binding agent using an amine nucleophile. That is, the immobilized binding agents having the labeled nucleic acid bound thereto may be contacted with an amine nucleophile. Typical amine nucleophiles include primary nucleophiles. Examples of primary amine nucleophiles include compounds having the formula:

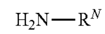

where $—R^N$ is a $C_{1-6}$ alkyl group or $—NH_2$

Preferably, the nucleophile is hydrazine. The hydrazine may be aqueous hydrazine.

The released nucleic acid comprises N6-(hydrazonomethyl) group ($—N═C(H)═N—NH_2$) on adenine. That is, the release nucleic acid may be represented by the formula:

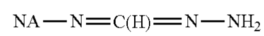

where NA is a nucleic acid.

Enrichment

In one embodiment, an $N^6$mAde-containing nucleic acid may be extracted from a population of nucleic acids. The $N^6$mAde-containing nucleic acids may be labeled with an isolation label ($—X_{Iso}$) using the methods of the invention. The labeled $N^6$mAde-containing nucleic acids may be isolated by contacting the labeled $N^6$mAde-containing nucleic with a binding agent, such as an immobilized binding agent. The immobilized binding agents having the labeled $N^6$mAde-containing nucleic acids bound thereto may be extracted from the population of nucleic acids.

Following extraction, the immobilized binding agents may be washed. Washing removes sample components that are not bound to the binding agent. For example, nucleic acids lacking labeled $N^6$mAde. Typically washing procedures include washing with solvents that can remove nucleic acids, such as aqueous buffer.

Following isolation, the labeled $N^6$mAde-containing nucleic acids may be released from the immobilized binding agent. Methods for realising bound substrates are well known in the art.

As noted above, the probe may be removed using a nucleophile, such as an amine nucleophile. In a preferred embodiment, the $N^6$mAde-containing nucleic acids may be released from the immobilized binding agent using hydrazine. That is, the immobilized binding agents having the labeled $N^6$mAde-containing nucleic acids bound thereto may be contacted with hydrazine.

The inventors have found that a minor by-product formed in the labeling method attaches the radical acceptor to guanine (Gua). The inventors have also found that treatment of the immobilized binding agents having the labeled nucleic acids bound thereto preferentially releases labeled $N^6$mAde-containing nucleic acids and retains labeled Gua-containing nucleic acids on the binding agent.

Detection

The method of the present invention comprises labeling a nucleic acid comprising N6-methyl adenine. In some embodiments, the method comprises detecting the labeled nucleic acid.

In some embodiments, the probe comprises a detection label ($—X_{Det}$). This allows the labeled nucleic acids to be detected using experimental techniques that detect the detection label.

Typical experimental techniques include fluorescence spectroscopy (utilizing a fluorescent label), phosphorescence spectroscopy (utilizing a phosphorescent label) and mass spectrometry or nuclear magnetic resonance (utilizing a radiolabel).

The detection may take place within a cell. The cell may be in vitro and may be an isolated cell, for example an isolated cell line or cell isolated from an individual. Alternatively, the cell may be in vitro and within a living organism.

Mapping

The method of the present invention comprises labeling a nucleic acid comprising N6-methyl adenine. Labeling a nucleic acid on $N^6$mAde allows the position of $N^6$mAde in the nucleotide sequence of the nucleic acid to be determined.

Accordingly, the present invention provides a method for mapping the position of $N^6$mAde within a target nucleic acid, the method comprising:

i) providing a target nucleic acid comprising $N^6$mAde, wherein the target nucleic acid has a known primary nucleotide sequence;
ii) labeling the target nucleic acid using the method for labeling $N^6$mAde described herein;
iii) amplifying the target nucleic acid to produce a population of nucleic acid fragments;
iv) sequencing the population of nucleic acid fragments to determine the base sequence of the nucleic acid fragments; and
v) comparing the nucleotide sequence of the nucleic acid fragments to the nucleotide sequence of the target nucleic acid, wherein termination of the nucleotide sequence of the nucleic acid fragments indicates the position of an $N^6$mAde residue in the nucleotide sequence of the target nucleic acid.

The amplification (or replication) step may be caried out using any suitable amplification method. Suitable amplification methods are known and include, for example, the polymerase chain reaction (PCR) (see, for instance, Green et al., Cold Spring Harb. Protoc., 2019; doi:10.1101/pdb.top095109).

The amplification step typically comprises contacting the labeled nucleic acid with a suitable polymerase or polymerase fragment. Suitable polymerases include DNA polymerase such as Taq DNA polymerase, Pfu DNA polymerase and Vent DNA Polymerase. Suitable polymerase fragments include the Klenow fragment of *E. coli* DNA polymerase I.

The amplification step typically comprises contacting the labeled nucleic acid with a suitable primer for initiation of the polymerase reaction. Where the primary nucleotide sequence of the target nucleic acid is known, a suitable primer can be designed using known techniques. Suitable techniques and protocols for the hybridisation of primers to a nucleic acid are known.

Preferably, the method may comprise ligating an adapter to one or both ends of the target nucleic acid. Suitable adapters typically comprise a primer binding site (a region that is complementary to a primer, such as a universal sequencing primer). This provides a known sequence so that an amplification or sequencing process may use a known primer. The adapter may additionally comprise a region that is complementary to an oligonucleotide bound to a solid support (e.g. a flow cell or bead). This allows the nucleic acid to be immobilized on a solid support. The adapter may additionally comprise a unique index sequence. This provides a sample identifier and permits multiplexing/pooling of multiple samples in a single sequencing run or flow cell lane. Suitable adapters are known in the art and typically depend on the sequencing platform to be employed. Suitable sequencing platforms include Illumina (e.g. MiSeq™ and TruSeq™), LifeTech IonTorrent, Roche 454 and PacBio RS.

Suitable methods for ligating an adapter to a nucleic acid are known. For example, a population of double-stranded genomic nucleic acids may contain dA overhangs (dA tails), for example following amplification or extension with a dA tailing polymerase, such as DreamTaq™ or Klenow exo-, or the double-stranded nucleic acid molecules may be blunt-ended and dA overhangs may be added to facilitate ligation of the first sequencing adapter. Suitable methods for adding dA overhangs to blunt ended nucleic acid molecules are known.

Typically, ligation of an adapter to one or both ends of the target nucleic acid is performed before the labelling reaction.

The amplification reaction may stall (terminate) once the labelled $N^6$mAde site is reached. Accordingly, the amplification step produces a population of a nucleic acid fragments that terminate at the site immediately before the $N^6$mAde site (position -1). The amplification step may be known as a "polymerase stop" assay.

Stalling may also occur at the position opposite the $N^6$mAde site (position 0) and the position after the $N^6$mAde site (position +1). However, the inventors observe that these stalling events are less frequent, and that stalling occurs predominately at position −1. Thus, the major product of the amplification step is a nucleic acid fragment terminating at position −1 relative to the full-length target nucleic acid.

Stalling (termination) of the amplification reaction can be improved if a larger (more sterically bulky) group is introduced during the labelling reaction. The inventors have found that labelling the nucleic with an isolation label ($—X_{Iso}$) and then binding the labelled nucleic acid with a binding agent that immobilized on a solid support is particularly effective for ensuring termination of the amplification reaction at the appropriate site (position −1). In such cases, the amplification reaction can be carried out while the nucleic acid is bound to the solid support (e.g., an "on bead" amplification).

The nucleic acid may be labelled with an isolation label ($—X_{Iso}$) by contacting the nucleic acid with a radical acceptor probe comprising the isolation label, or by further modifying a nucleic acid labelled with a modification label ($—X_{Mod}$) with a bifunctional probe containing an isolation label ($—X_{Iso}$).

Accordingly, in a preferred embodiment, the method for mapping the position of $N^6$mAde within a target nucleic acid comprises:

i) providing a target nucleic acid comprising $N^6$mAde, wherein the target nucleic acid has a known primary nucleotide sequence;

ii) labeling the target nucleic acid with an isolation label ($—X_{Iso}$) as described herein;

iii) contacting the nucleic acid with a binding agent that binds to the isolation label ($—X_{Iso}$), wherein the binding agent is immobilized on a solid support;

iv) amplifying the target nucleic acid bound to the solid support to produce a population of nucleic acid fragments;

v) sequencing the population of nucleic acid fragments to determine the nucleotide sequence of the nucleic acid fragments; and vi) comparing the nucleotide sequence of the nucleic acid fragments to the nucleotide sequence of the target nucleic acid, wherein termination of the nucleotide sequence of the nucleic acid fragments indicates the position of an $N^6$mAde residue in the nucleotide sequence of the target nucleic acid.

Suitable isolation labels ($—X_{Iso}$) are set out above for the group $—X^2$. Preferably, the isolation label is biotin.

Suitable binding agents are set out above for the extraction step. Preferably, the binding agent is streptavidin.

Suitable solid supports are set out above for the extraction step. Preferably, the solid support is a microbead, such as a magnetic microbead.

After the amplification step (and prior to the sequencing step), the label may be removed from the nucleic acid. As noted above, the probe compounds disclosed herein (e.g. the probe of formula I) react with the N6-methyl position of $N^6$mAde to form an N-hydroxyformamidine linkage. This N-hydroxyformamidine linkage can be cleaved using a nucleophile. Accordingly, the method may comprise, after the amplification step, contacting the labeled nucleic acid with a nucleophile to remove the label. Suitable nucleophiles are set out for the probe removal step above, and the same preferences apply.

The amplification step stalls at the site immediately before the $N^6$mAde site (position −1). Thus, the amplification step results in a nucleic acid fragment bound to (hybridised to) the full-length target nucleic acid. Thus, there is a double-stranded nucleic acid portion and a single-stranded overhang portion. Preferably, the single-strand overhang is removed prior to the sequencings step. Methods for removing or digesting single-stranded nucleic acids are known. Preferably, an exonuclease is used. Accordingly, the method may comprise, prior to the sequencing step, contacting the nucleic acids with an exonuclease to remove the overhang.

The sequencing step may be caried out using any suitable sequencing technique or platform. Suitable sequencing techniques and platforms including Sanger sequencing, Solexa-Illumina sequencing (for example, MiSeq™ or TruSeq™), ligation-based sequencing (SOLiD™), pyrosequencing, single molecule real-time sequencing (SMRT™), PacBioscience sequencing. and semiconductor array sequencing (Ion Torrent™). Preferably, sequencing is performed by next-generation sequencing. More preferably, Solexa-Illumina sequencing (for example, MiSeq™) is used.

Suitable protocols, reagents and apparatus for nucleic acid sequencing are known and are available commercially. Specific examples include *NEBNext Ultra II FS DNA Library Prep Kit* (New England Biolabs).

The sequencing technique or platform employed will be compatible with the adapters ligated to the target nucleic acid. That is, the adapters comprise a primer binding site for the amplification reaction and a primer binding site for the sequencing platform. These two primer binding sites may be the same or different.

The method comprises comparing the nucleotide sequence of the nucleic acid fragments to the nucleotide sequence of the target nucleic acid. The amplification step stalls (terminates) once the $N^6$mAde position is reached (that is, polymerase stalling occurs just before incorporation of the nucleotide opposite to the $N^6$mAde, position −1). Accordingly, aligning and comparing the nucleotide sequence of the nucleic acid fragments with the nucleotide sequence of the target nucleic acid indicates the position of $N^6$mAde in the nucleotide sequence of the target nucleic acid.

In some embodiments, sequencing is repeated to provide a set of sequence reads of nucleic acid fragments. For example, 10 or more, 100 or more, or 1000 or more sequence reads may be determined.

The sequence reads may be analysed by routine bioinformatic techniques. For example, low quality sequence reads and reads arising only from sequencing adaptors may be removed and the sequence reads may be aligned with reference sequences.

The identified sequence reads of the nucleic acid fragments may be analysed to determine the location of $N^6$mAde sites in a population of nucleic acids. When the population of nucleic acids are genomic DNA, the nucleic acid fragments may be analysed to determine the location of $N^6$mAde sites in the genome. For example, a sequence read of the nucleic acid fragments that terminates at a position in the sequence of a nucleic acid in the population may be indicative of the presence of an $N^6$mAde site at that position. In some embodiments, an increased proportion of sequence reads that terminate at a position in the sequence of a nucleic acid in the population relative to other positions may be indicative of the presence of an $N^6$mAde site at that position.

A pattern or map of $N^6$mAde sites in the population of nucleic acids may be determined from the set of sequence reads. For a population of genomic DNA molecules obtained from a sample of cells, the pattern or map of $N^6$mAde sites in the genome or part of the genome of the cells may be determined from the set of sequence reads.

In the mapping method set out above, the primary nucleotide sequence of the target nucleic acid is known. That is, the sequence of canonical bases (A, T, C, G, U) is known. However, the methods of the invention can also be used to determine the position of $N^6$mAde in the nucleotide sequence of a target nucleic acid whose primary nucleotide sequence is not known. In such cases, the method comprises determining the primary nucleotide sequence of the target nucleic acid using standard sequencing techniques. Standard sequencing techniques such as Sanger sequencing and Solexa-Illumina sequencing (for example, MiSeq™ or TruSeg™) do not differentiate between adenine (A) and N6-methyl adenine, reading A at that position.

Accordingly, the method may comprise:

i) providing a population of target nucleic acids comprising $N^6$mAde, wherein the target nucleic acid has an unknown primary nucleotide sequence;

ii) sequencing a first portion of the population to determine the primary nucleotide sequence of the target nucleic acid.

Methods for determining the primary nucleotide sequence of a target nucleic acid having an unknown nucleotide sequence are known. Suitable sequencing techniques and platforms including Sanger sequencing, Solexa-Illumina sequencing (for example, MiSeq™ or TruSeq™), ligation-based sequencing (SOLiD™), pyrosequencing, single molecule real-time sequencing (SMRT™), PacBioscience sequencing. and semiconductor array sequencing (Ion Torrent™). Preferably, sequencing is performed by next-generation sequencing. More preferably, Solexa-Illumina sequencing (for example, MiSeq™) is used.

Suitable protocols, reagents and apparatus for nucleic acid sequencing are known and are available commercially. Specific examples include NEBNext Ultra II FS DNA Library Prep Kit (New England Biolabs).

The sequencing step typically comprises ligating an adapter to one or both ends of the target nucleic acid. Suitable adapters comprise a primer binding site for the sequencing process may use a known primer, optionally together with a site for binding to a solid support (e.g. a flow cell or bead), and/or a unique index sequence. Suitable adapters are known in the art and typically depend on the sequencing platform to be employed. Suitable sequencing platforms include Illumina (e.g. MiSeq™ and TruSeq™), LifeTech IonTorrent, Roche 454 and PacBio RS.

Suitable methods for ligating an adapter to a nucleic acid are known.

Uses

In some aspects of the invention, there is provided the use of a compound of formula (I) as a radical acceptor:

(I)

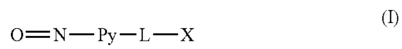

where -Py- is a pyridinediyl group, -L- is a linker and X is a label.

Preference for each component of the compound of formula (I) are set out above.

Preferably, the compounds of formula (I) is used as a radical acceptor for an alpha-amino radical formed on the N6-methyl position of N6-methyl adenine ($N^6$mAde).

Compounds

In some aspects of the invention, there is provided a compound of formula (III):

(III)

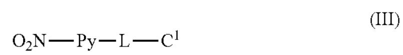

where, -Py- is a pyridinediyl group, -L- is a linker and —$C^1$ is a click reaction partner such as a group selected from alkynyl, alkenyl or isocyanide (—$N^+{\equiv}C^-$).

Preferences for each of the components of the compound of formula (III) (-Py-, -L-) are the same as those for the probe of formula (I) as set out above.

In a particularly preferred embodiment, there is provided a compound having the formula:

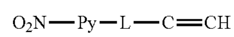

where -Py- is a pyridinediyl group and -L- is a linker, as set out for the probe of formula (I) and the same preferences apply.

In a particularly preferred embodiment, there is provided a compound selected from compounds of formula P1 to P7. Preferably, the compound is P7.

| Compound | Structure |
|---|---|
| P1 | 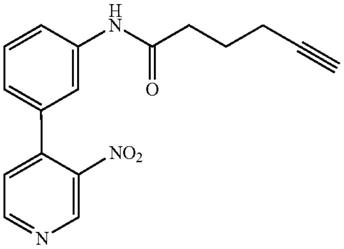 [SMILES: C#CCCCC(=O)Nc1cccc(-c2ccncc2[N+](=O)[O-])c1] |
| P2 | 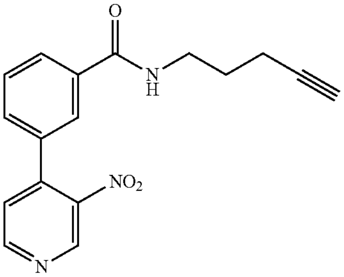 [SMILES: C#CCCCNC(=O)c1cccc(-c2ccncc2[N+](=O)[O-])c1] |
| P3 | 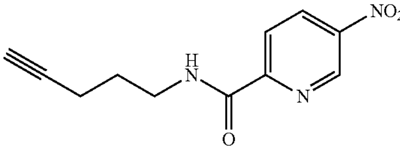 |
| P4 | 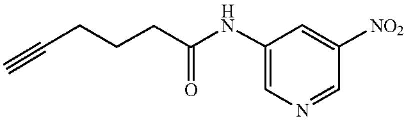 [SMILES: C#CCCCC(=O)Nc1cncc([N+](=O)[O-])c1] |
| P5 | 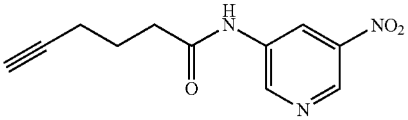 [SMILES: C#CCCCC(=O)Nc1cncc([N+](=O)[O-])c1] |
| P6 | 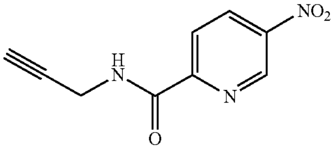 |
| P7 | 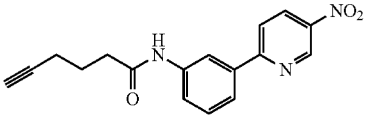 [SMILES: C#CCCCC(=O)Nc1cccc(-c2ccc([N+](=O)[O-])cn2)c1] |

Kits

One aspect of the invention pertains to a kit comprising:

(a) a compound comprising a nitropyridyl group ($O_2N$-Py-); and (b) a tertiary amine; and (c) a photocatalyst.

Suitable compounds comprising a nitropyridyl group are set out above. Preferably, the compound comprising a nitropyridyl group is a precursor of formula (II):

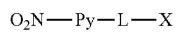

(II)

where -Py- is a pyridinediyl group, -L- is a linker and X is a label, as set out above.

Suitable tertiary amines are set out above. Preferably, the tertiary amine is a quinuclidine having the formula:

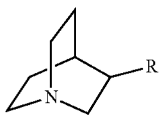

where, R is selected from a hydrogen atom, a hydroxyl group, a $C_{1-6}$ alkyl group, a $C_{1-6}$ alkoxy group, a $C_{1-6}$ acyloxy group, a $C_{1-6}$ reverse ester group or a group —$C(OH)R_1R^2$ (where $R_1$ and $R_2$ are selected from $C_{1-6}$ alkyl).

Suitable photocatalysts are set out above. Preferably, the photocatalyst is a ruthenium or iridium photocatalyst, such as $[Ru(phen)_3]^{2+}$ or $[Ru(bpz)_3]^{2+}$.

The kit may be provided in a suitable container and/or with suitable packaging;

Optionally, the kit may include instructions for use, e.g., written instructions on how to use the kit in a method of labeling a nucleic acid comprising $N^6$Ade.

The kit may further comprise nucleic acid isolation reagents. Suitable reagents are well-known in the art and include spin-chromatography columns.

The kit may further comprise a labeling buffer for attachment of the compound to nucleic acid containing $N^6$mAde.

The kit may further comprise a specific binding agent. The binding agent may bind specifically to an isolation label of the compound in the kit. For example, the specific binding member may bind to a biotin isolation label. Suitable binding agents include streptavidin. The binding agent may be immobilized or immobilizable on a solid support.

The kit may further comprise a solid support. The solid support may be coated or coatable with the binding agent. Suitable solid supports are described above and include magnetic beads. In some preferred embodiments, the isolation label of the compound is biotin and the solid support is streptavidin-coated magnetic beads. A magnet may be included in the kit for purification of the magnetic beads.

Optionally, the kit may include reagents for removing the compound from the nucleic acid, or for releasing the nucleic acid from the binding agents. Suitable reagents for removing the compound from the nucleic acid include amine nucleophiles and hydrazine as set out above.

A kit may include one or more other reagents required for the method, such as buffer solutions, sequencing and other reagents.

A kit may include sequencing adapters and one or more reagents for the attachment of sequencing adapters to the ends of isolated nucleic acids, such as T4 ligase.

A kit may include one or more reagents for the amplification of a population of nucleic acids using the amplification primers. Suitable reagents may include a thermostable polymerase, for example a high discrimination polymerase, dNTPs and an appropriate buffer.

The kit may further comprise one or more oligonucleotides for use as controls. A suitable positive control oligonucleotide may be a nucleic acid comprising at least one $N^6$mAde.

A suitable negative control oligonucleotide may be a nucleic acid devoid of $N^6$mAde.

A kit for use in labeling, enrichment or detection of $N^6$mAde may include one or more articles and/or reagents for performance of the method, such as means for providing the test sample itself, including DNA and/or RNA isolation and purification reagents, sample handling containers (such components generally being sterile), and other reagents required for the method, such as buffer solutions, sequencing and other reagents.

Salts, Solvates and Other Forms

Examples of salts of the radical acceptor, probe, precursor and photocatalyst include all salts, such as, without limitation, acid addition salts of strong mineral acids such as HCl and HBr salts and addition salts of strong organic acids such as a methanesulfonic acid salt. Further examples of salts include sulphates and acetates such as trifluoroacetate or trichloroacetate.

A reference to a radical acceptor, probe, precursor, photocatalyst or any other compound described herein, is also a reference to a solvate of that compound. Examples of solvates include hydrates.

A radical acceptor, probe, precursor, photocatalyst or any other compound described herein, includes a compound where an atom is replaced by a naturally occurring or non-naturally occurring isotope. In one embodiment the isotope is a stable isotope. Thus a compound described herein includes, for example deuterium containing compounds and the like. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Any of the compound described herein, may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-6}$ alkyl includes n-propyl and iso-propyl; butyl includes n-, iso-, sec-, and tert-butyl; methoxyphenyl includes ortho-, meta-, and para-methoxyphenyl).

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallization and chromatographic means) of such isomeric forms are either known in the art or are readily obtained by adapting the methods taught herein, or known methods, in a known manner.

One aspect of the present invention pertains to compounds in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Definitions

An alkyl group is monovalent saturated hydrocarbon group. The alkyl group may be a $C_{1-6}$ alkyl group, for example a $C_{1-4}$, $C_{1-3}$ or a $C_{1-2}$ alkyl group. In this context, the prefix (e.g. $C_{1-6}$) denotes the number of carbon atoms in the hydrocarbon backbone. The alkyl group may be linear or branched.

Examples of $C_{1-6}$ linear alkyl groups include methyl (-Me), ethyl (-Et), n-propyl (-nPr), n-butyl (-nBu), n-pentyl (-Amyl) and n-hexyl. Examples of $C_{1-6}$ branched alkyl groups include iso-propyl (-iPr), iso-butyl (-iBu), sec-butyl (-sBu), tert-butyl (-tBu), iso-pentyl, sec-pentyl, tert-pentyl, neo-pentyl, iso-hexyl, sec-hexyl, tert-hexyl and neo-hexyl.

An alkenyl group is a monovalent unsaturated hydrocarbon group containing one or more carbon-carbon double bonds. The alkenyl group may be a $C_{2-20}$ alkenyl group, for example a $C_{2-10}$, $C_{2-6}$ or a $C_{2-4}$ alkenyl group. In this context, the prefix (e.g. $C_{1-6}$) denotes the number of carbon atoms in the hydrocarbon backbone. The alkenyl group may be linear or branched. The alkenyl group may be incorporated into a ring system.

Examples of linear alkenyl groups include ethenyl (vinyl), 1-propenyl, 2-propenyl (allyl), 1-butenyl, 1-pentenyl, and 1-hexenyl. Examples of branched alkenyl groups include isopropenyl (1-methylvinyl). Examples of alkenyl groups incorporated into a ring system include norbornene, oxanorbornene and trans-cycloctene.

An alkynyl group is a monovalent unsaturated hydrocarbon group containing one or more carbon-carbon triple bonds. The alkynyl group may be a $C_{2-20}$ alkynyl group, for example a $C_{2-10}$, $C_{2-6}$ or a $C_{2-4}$ alkynyl group. In this context, the prefix (e.g. $C_{1-6}$) denotes the number of carbon atoms in the hydrocarbon backbone. The alkynyl group may be linear or branched. The alkenyl group may be incorporated into a ring system.

Examples of linear alkynyl groups include ethynyl and 2-propynyl (propargyl). Examples of alkynyl groups incorporated into a ring system include cyclooctyne (OCT).

An aryl group is a monovalent hydrocarbon group comprising an aromatic ring in which all of the ring atoms are carbon atoms. The aryl group may be a $C_{5-20}$ aryl group, for example a $C_{5-14}$, $C_{5-10}$ or a $C_{5-6}$ aryl group. In this context, the prefix (e.g. $C_{5-10}$) denotes the number or range of ring atoms. The aryl group may be monocyclic, or it may comprise two or more rings in a fused ring system. In a fused ring system the aryl group comprises two or more rings, wherein at least one of the rings is an aromatic ring in which all of the ring atoms are carbon atoms, and wherein each ring shares two adjacent ring atoms with each neighbouring (fused) ring. Thus, the bridgehead atoms are directly bonded.

Examples of monocyclic aryl groups include those derived from benzene (phenyl). Examples of aryl groups comprising fused rings include groups derived from: indane (2,3-dihydro-1H-indene), indene, isoindene; naphthalene, dialin (1,2-dihydronaphthalene), tetralin (1,2,3,4-tetrahydronaphthalene), azulene; acenaphthene; fluorene, phenalene; and anthracene and phenanthrene.

A heteroaryl group is an aryl group comprising an aromatic ring in which one or more ring atoms are heteroatoms, for example N, O and S. The heteroaryl group may be a $C_{5-20}$ heteroaryl group, for example a $C_{5-14}$, $C_{5-10}$ or a $C_{5-6}$ heteroaryl group. The heteroaryl group may be monocyclic, or it may comprise two or more rings in a fused ring system. In a fused ring system the heteroaryl group comprises two or more rings, wherein at least one of the rings is an aromatic ring in which one or more ring atoms are heteroatoms, and wherein each ring shares two adjacent ring atoms with each neighbouring (fused) ring. Thus, the bridgehead atoms are directly bonded.

Examples of monocyclic $C_{5-20}$ heteroaryl groups include groups derived from: pyrrole (azole), pyrazole (1,2-diazole), imidazole (1,3-diazole), triazole, tetrazole; furan (oxole); thiophene (thiole); oxazole, isoxazole, oxadiazole (e.g. furazan), oxatriazole; thiazole, isothiazole; pyridine (azine), pyridazine (1,2-diazine), pyrimidine (1,3-diazine), pyrazine (1,4-diazine), triazine; and isoxazine.

Examples of $C_{5-20}$ heteroaryl groups comprising fused rings include groups derived from: indole, isoindole, indolizine, indoline, isoindoline, purine, benzimidazole, indazole, azaindole, benzotriazole; benzofuran, isobenzofuran, indole, isoindole, indolizine, indoline, isoindoline, purine, benzimidazole, indazole, benzoxazole, benzisoxazole, benzodioxole, benzofurazan, benzotriazole, benzothiofuran, benzothiazole, benzothiadiazole; benzofuran, isobenzofuran, indole, isoindole, indolizine, indoline, isoindoline, purine, benzimidazole, indazole, benzoxazole, benzisoxazole, benzodioxole, benzofurazan, benzotriazole, benzothiofuran, benzothiazole, benzothiadiazole; benzofuran, isobenzofuran, indole, isoindole, indolizine, indoline, isoindoline, purine, benzimidazole, indazole, benzoxazole, benzisoxazole, benzodioxole, benzofurazan, benzotriazole, benzothiofuran, benzothiazole, benzothiadiazole; quinoline, isoquinoline, quinolizine, quinoxaline, phthalazine, quinazoline, cinnoline, naphthyridine, pyridopyrimidine, pyridopyrazine, pteridine; chromene, isochromene, chromane, isochromane, benzodioxan, quinoline, isoquinoline, quinolizine, benzoxazine, benzodiazine, pyridopyridine, quinoxaline, quinazoline cinnoline, phthalazine, naphthyridine, pteridine; benzodiazepine; carbazole, carboline, perimidine, pyridoindole; carbazole, dibenzofuran, dibenzothiophene, carboline, perimidine, pyridoindole; acridine, phenazine, phenanthridine, phenanthroline, phenazine, acridine, xanthene, thioxanthene, oxanthrene, phenoxathiin, phenazine, phenoxazine, phenothiazine, thianthrene, phenanthridine, phenanthroline, phenazine.

A hydroxyl group is —OH or the hydroxide form of this group.

An alkoxy group is —OR, where R is an alkyl group. Examples of alkoxy groups include methoxy (—OMe), ethoxy (—OEt), n-propoxy (—O(nPr)), isopropoxy (—O(iPr)), n-butoxy (—O(nBu)), sec-butoxy (—O(sBu)), isobutoxy (—O(iBu)), and tert-butoxy (—O(tBu)).

An acyl group is —C(═O)H or —C(═O)R, where —R is selected from substituted or unsubstituted alkyl, alkenyl, alkynyl, cycloalkyl, heterocyclyl, aryl and heteroaryl. Examples of acyl groups include formyl, acetyl (—Ac), propionyl, tert-butyryl and benzoyl (-Bz).

An acyloxy (ester) group is —C(O)OR, where —R is selected from substituted or unsubstituted alkyl, alkenyl, alkynyl, cycloalkyl, heterocyclyl, aryl and heteroaryl.

A reverse ester group is —OC(O)R, where R is selected from substituted or unsubstituted alkyl, alkenyl, alkynyl, cycloalkyl, heterocyclyl, aryl and heteroaryl. Examples of reverse ester groups include acetoxy (—OAc).

An amide (carboxamide) group is $—C(═O)NR^1R^2$, where $—R^1$ and $—R^2$ are independently selected from substituted or unsubstituted alkyl, alkenyl, alkynyl, cycloalkyl, heterocyclyl, aryl and heteroaryl. Examples of amide groups include, but are not limited to, $—C(═O)NH_2$, $—C(═O)NHCH_3$, $—C(═O)N(CH_3)_2$, —C(═O)NHEt, and $—C(═O)NEt_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

A reverse amide group is $—N(R^1)C(═O)R^2$, where $—R^1$ and $—R^2$ are selected from independently selected from substituted or unsubstituted alkyl, alkenyl, alkynyl, cycloalkyl, heterocyclyl, aryl and heteroaryl. Examples of reverse amide groups include acetamide (—NHC(═O)Me), —NHC(═O)Et, and —NHC(═O)Ph. $R^1$ and $R^2$ may together form a cyclic structure, as in, for example, succinimidyl, maleimidyl, and phthalimidyl An alkylene (alkanediyl) group is a divalent saturated hydrocarbon group in which the two free valencies independently form part of a single bond to separate adjacent atom.

The alkylene group may be a $C_{1-6}$ alkylene group, for example, a $C_{1-4}$ or a $C_{1-3}$ alkylene group. In this context, the prefix (e.g. $C_{1-6}$) denotes the number of atoms in the hydrocarbon backbone. The alkylene group may be linear or branched. Examples of linear alkylene groups include methanediyl (methylene bridge), ethane-1,2-diyl (ethylene bridge), propane-1,3-diyl, butan-1,4-diyl, pentan-1,5-diyl and hexan-1,6-diyl. Examples of branched alkylene groups include ethane-1,1-diyl and propane-1,2-diyl.

A heteroalkylene group is an alkylene group in which one or more carbon atoms is replaced with a heteroatom, for example N, O and S. The heteroalkylene group may be a $C_{1-6}$ heteroalkylene group, for example, a $C_{1-4}$ or a $C_{1-3}$ heteroalkylene group. In this context, the prefix (e.g. $C_{1-6}$) denotes the number of atoms in the heteroalkylene backbone, whether carbon atoms or heteroatoms. The heteroalkylene group may be linear or branched. Examples of linear heteroalkylene groups include those derived from oxymethylene (e.g. polyoxymethylene, POM), ethylene glycol (e.g. polyethylene glycol, PEG), ethylenimine (e.g. linear polyethylenimine, PEI; polyaziridine) and tetramethylene glycol (e.g. polytetramethylene glycol, PTMEG; polytetrahydrofuran). Examples of branched heteroalkylene groups include those derived from propylene glycol (e.g. polypropylene glycol PPG). Where a nitrogen atom is present in a heteroalkylene group, that nitrogen atom may be unsubstituted (NH) or optionally substituted with an alkyl group. Where a sulfur atom is present in a heteroalkylene group, that sulfur atom may be S, S(O) or $S(O)_2$.

A cycloalkylene group is a divalent saturated hydrocarbon group which comprises a ring in which all of the ring atoms are carbon atoms, and in which the two free valencies each form part of a single bond to an adjacent atom. The cycloalkylene group may be a $C_{5-6}$ cycloalkylene group. In this context, the prefix (e.g. $C_{5-6}$) denotes the number or range of ring atoms. The cycloalkylene group may be monocyclic. Examples of monocylic cycloalkylene groups include 1,3-cyclopentylene and 1,4-cyclohexylene.

A heterocycloalkylene (heterocyclene) group is a cycloalkylene group in which one or more carbon atoms is replaced with a heteroatom, for example N, O and S, or in which one or more carbon atoms has an oxo substituent (=O). The heterocycloalkylene group may be a $C_{5-6}$ heterocycloalkylene group. In this context, the prefix (e.g. $C_{5-6}$) denotes the number or range of ring atoms, whether carbon atoms or heteroatoms. The heterocycloalkylene group may be monocyclic. Where a nitrogen atom is present in a heteroalkylene group, that nitrogen atom may be unsubstituted (NH) or optionally substituted with an alkyl group. Where a sulfur atom is present in a heteroalkylene group, that sulfur atom may be S, S(O) or $S(O)_2$.

An arylene (arenediyl) group is a divalent hydrocarbon group comprises an aromatic ring in which all of the ring atoms are carbon atoms, and in which the two free valencies each form part of a single bond to an adjacent atom. The arylene group may be a $C_{6-10}$ arylene group. In this context, the prefix (e.g. $C_{6-10}$) denotes the number or range of ring atoms. The arylene group may be monocyclic, or it may comprise two or more rings. Examples of monocyclic arylene groups include 1,4-phenylene (1,4-benzenediyl). Examples of bicyclic arylene groups include 2,6-naphthalenediyl.

A heteroarylene group is an arylene group comprising an aromatic ring in which one or more ring atoms are heteroatoms, for example N, O and S, or in which one or more carbon atoms has an oxo substituent (=O). The heteroarylene group may be a $C_{6-10}$ heteroarylene group. In this context, the prefix (e.g. $C_{6-10}$) denotes the number or range of ring atoms, whether carbon or heteroatom. The heteroarylene group may be monocyclic, or it may comprise two or more rings. Examples of monocyclic heteroarylene groups include 2,5-pyridinediyl and 2,5-pyrrolediyl.

An amide linkage is —N($R^N$)—C(═O)— where —$R^N$ is selected from hydrogen, alkyl, alkenyl, alkynyl, cycloalkyl and aryl. The amine linkage may be oriented such that either the nitrogen atom or the carbonyl carbon atom binds to the adjacent groups.

An ester linkage is —O—C(═O)—. The ester linkage may be oriented such that either the ether oxygen atom or the carbonyl carbon atom binds to the adjacent groups.

A carbonyl linkage is —C(═O)—.

An amine linkage is —N($R^N$)— where $R^N$ is selected from hydrogen, alkyl, alkenyl, alkynyl, cycloalkyl and aryl.

A ether (oxy) linkage is —O—.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Sequences

The present invention is described herein with reference to the sequence identification numbers listed below.

SEQ ID NO 1: DNA template 1

SEQ ID NO 2: DNA template 2

SEQ ID NO 3: Reverse primer 1

SEQ ID NO 4: Reverse primer 2

Experimental and Results

1. General Remarks

Proton nuclear magnetic resonance ($^1H$ NMR) spectra were recorded at ambient temperature on a 400 MHz Bruker Avance III HD spectrometer (400 MHz) or a 500 MHz BrukerAvance III HD Smart Probe spectrometer (500 MHz). Chemical shifts (6) were reported in ppm and quoted to the nearest 0.01 ppm relative to the residual protons in CDCl3 (7.26 ppm), DMSO-d6 (2.50 ppm), methanol-d4 (3.31 ppm) and coupling constants (J) were quoted in Hertz (Hz). Coupling constants were quoted to the nearest 0.1 Hz and multiplicity reported according to the following convention: s=singlet, d=doublet, t=triplet, q=quartet, qnt=quintet, sxt=sextet, spt=septet, oct=octet, m=multiplet, br=broad and associated combinations, e.g. dd=doublet of doublets. Where coincident coupling constants have been observed, the apparent (app) multiplicity of the proton resonance has been reported. Data were reported as follows: chemical shift (multiplicity, coupling constants, number of protons and molecular assignment).

Carbon nuclear magnetic resonance (13C NMR) spectra were recorded at ambient temperature on a 400 MHz Bruker Avance III HD spectrometer (101 MHz) or a 500 MHz BrukerAvance III HD Smart Probe spectrometer (126 MHz). Chemical shifts (δ) were reported in ppm and quoted to the nearest 0.1 ppm relative to the residual solvent peaks in CDCl3 (77.16 ppm), DMSO-d6 (39.52 ppm), and methanol-d4 (49.00 ppm). DEPT135, NOE experiments and 2-dimensional experiments (COSY, HMBC and HSQC) were used to support assignments when appropriate but were not included herein.

LCMS spectra were recorded on an Amazon X ESI-MS (Bruker) connected to an Ultimate 3000 LC (Dionex). Oligodeoxyribonucleotidess were analysed using a gradient of 5-30% methanol vs. an aqueous solution of 10 mM triethylamine and 100 mM hexafluoro-2-propanol on a XTerra MS C18 column (125 Å, 2.5 μm, 2.1×50 mm) with TMS endcapping. Small molecules were analysed with a gradient of 0-100% acetonitrile with 0.1% formic acid vs. water with 0.1% formic acid on a Kinetex® C18 column (100 Å, 2.6 μm, 50×2.1 mm).

Nucleosides in functionalization studies and after digestion of functionalized ODNs were analyzed with gradient of 0-100% acetonitrile vs. water with 10 mM ammonium acetate on a Kinetex® C18 column (100 Å, 2.6 μm, 50×2.1 mm). Mass chromatograms shown are base peak chromatograms, UV absorption was recorded at 260 nm.

High-resolution mass spectra (HRMS) of small molecules were conducted using Shimadzu LC-MS 9030 QToF. Oligodeoxyribonucleotidess were analysed using a gradient of 5-30% methanol vs. an aqueous solution of 10 mM triethylamine and 100 mM hexafluoro-2-propanol on a XTerra MS C18 column (125 Å, 2.5 μm, 2.1×50 mm) with TMS endcapping. Small molecules were analysed with a gradient of 0-100% acetonitrile with 0.1% formic acid vs. water with 0.1% formic acid on a Kinetex® C18 column (100 Å, 2.6 μm, 50×2.1 mm). Analytical thin layer chromatography (TLC) was performed using pre-coated Merck glass-backed silica gel plates (Silicagel 60 F254 0.2 mm). Visualization was achieved using ultraviolet light (254 nm) and chemical staining with basic potassium permanganate solution as appropriate. Flash column chromatography was undertaken on Fluka or Material Harvest silica gel (230-400 mesh) under a positive pressure of air or on a CombiFlash Rf 200 (Teledyne Isco) system using 50 μm Si—HP PuriFlash columns.

Automated gel electrophoresis was performed using an Agilent Technologies 2200 Tapestation and D1000 ScreenTapes and sample buffer.

qPCR was performed using a CFX96 Real-TimeSystem (BioRad), and data was processed using CFX software manager 3.1 (BioRad). qPCR reactions (volume: 10 μL) contained DNA calibration or sample mixtures (1 μL), the corresponding forward and reverse primers (1 μM each), and Brilliant III ultra-Fast SYBR green qPCR mastermix (Agilent Technologies, 5 μL). Reactions were run according to the manufacturer's protocol. Calibration curves were made to determine the amounts of target DNA in the analysed samples.

Oligodeoxyribonucleotides (ODNs), including short ONDs for reactions, 99 nt ssDNA strands and template and primers for the synthesis of 99 nt dsDNA strands were custom synthesised and HPLC-purified by ATDBio or Sigma-Aldrich and used without further purification after dissolution into milliQ H2O.

Reagents were obtained from Sigma-Aldrich, Acros, Alfa Aesar, TCI, or Jena Bioscience and used without further purification. Enzyme solutions were obtained from Zymo, New England BioLabs, and Sigma and used directly. Probe compounds 5-nitro-2-phenylpyridine and 3-nitro-4-phenylpyridine are available from commercial sources (Sigma-Aldrich, Toronto Research Chemicals).

Dichloromethane, ethyl acetate, tetrahydrofuran, toluene, and petroleum ether (40-60) were dried and distilled using standard methods. Water was purified on a milliQ system. Other solvents used were purchased anhydrous and used without further purification unless otherwise stated.

Reactions were carried out under nitrogen atmosphere unless otherwise stated. Reactions were monitored by LCMS.

General Procedures

General Procedure A: Functionalization of $N^6$mdA in Short ODNs with Quinuclidine and Derivatives A 2 mL microwave vial was charged with a solution containing the ODN substrate (200 μM in milliQ $H_2O$, 12.5 μL). In a separate Eppendorf tube, the appropriate amount of quinuclidine or its derivative was dissolved using a stock solution of $[Ru(bpz)_3](PFe)_2$ (2 mg in 1 mL of 20% MeCN in milliQ $H_2O$, 2.3 mM, 12.5 μL) or $[Ru(phen)_3]Cl_2$ (2 mM in 20% MeCN in milliQ $H_2O$, 12.5 μL). The latter mixture was then added to the ODN solution and the microwave vial was sealed under nitrogen atmosphere after flushing for 15-20 seconds. The vial was then placed at 5 cm from a 15 W CFL bulb. The reaction was irradiated for 5 hours, diluted with milliQ $H_2O$ (25 μL) and filtered through a prewashed Mini Quick Spin Oligo Column (Roche). The obtained mixture was analyzed directly by LCMS.

General Procedure B: Functionalization of $N^6$mdA in Short ODNs with 3-Nitropyridine and Derivatives A 2 mL microwave vial was charged with a solution containing the ODN substrate (200 μM in milliQ $H_2O$, 12.5 μL). In a separate Eppendorf tube, quinuclidine (5.5 mg, 50 μmmol) and the appropriate amount of 3-nitropyridine or respective derivatives were dissolved using a stock solution of $[Ru(bpz)_3](PF_6)_2$ (2 mg in 1 mL of 20% MeCN in milliQ $H_2O$, 2.31 mM, 12.5 μL) or $Ru(Phen)_3Cl_2$ (1.5 mg in 1 mL of 20% MeCN in milliQ $H_2O$, 2.1 mM, 12.5 μL). The latter mixture was then added to the oligo solution and the microwave vial was sealed under nitrogen atmosphere, flushing for 15-20 seconds. The vial was then placed in a distilled-water bath at approximately 1 cm from a 15 W CFL or 55 W CFL bulb or inside a 55W CFL bulb, in which case a fan was used for temperature control. The reaction was irradiated for 10 min (if not stated otherwise), diluted with water (25 μL) and filtered through a prewashed Mini Quick Spin Oligo Column (Roche). The obtained mixture was analyzed directly by LCMS.

General Procedure C: Click Reaction on the Functionalized $N^6$mdA in Short ODNs To the resulting ODN mixture from general procedure B (25 μL) in a 1.5 ml Eppendorf tube was added quinuclidine (5.5 mg, 50 μmol, dissolved in 10 μL of milliQ $H_2O$), azide-$PEG_3$-biotin conjugate (20 mM, 5 μL), sodium ascorbate (40 mM, 5 μL) and $CuSO_4$ (2 mM, 5 μL). Final concentrations: quinuclidine 1 M, azide-$PEG_3$-biotin conjugate: 2 mM, sodium ascorbate: 4 mM, $CuSO_4$ 0.2 mM. After 30 min reaction at room temperature, the reaction was filtered through a prewashed Mini Quick Spin Oligo Column (Roche). The obtained mixture was analyzed directly by LCMS.

General Procedure D: Enrichment of Short $N^6$mdA ODNs with Streptavidin Magnetic Beads To the resulting ODN mixture from general procedure C in a 1.5 ml Eppendorf DNA LoBind microcentrifuge tube was added 5× adapted binding buffer (40 μL; 25 mM Tris, 2.5 mM EDTA, 5 M NaCl, pH 8.5) and milliQ $H_2O$ (for a final volume of 200 μL). Streptavidin MagneSphere® Paramagnetic Particles (300 μL of a 1 mg/ml suspension) were suspended in a 1.5 ml Eppendorf DNA LoBind microcentrifuge tube, separated from the storage buffer on a magnetic stand, washed twice with 0.5×SSC buffer (200 μL; 75 mM NaCl, 7.5 mM sodium citrate, pH 7.2) and once with 1× adapted binding buffer (200 μL; 5 mM Tris, 0.5 mM EDTA, 1 M NaCl, pH 8.5). The oligo solution (200 μL) was added to the paramagnetic particles and after 10 minutes incubation at r.t. the supernatant was collected for LCMS analysis. The beads were carefully washed with 1× adapted binding buffer (3×200 μL), then transferred into a new microcentrifuge tube with 200 ul adapted binding buffer and washed another time with adapted binding buffer (1×200 μL). They were then incubated in 100 mM NaOH (3×10 min at r.t. with 200 μL), and finally washed again with adapted binding buffer (3×200 μL). Elution of the retained oligonucleotides was performed by incubation with 10% aqueous hydrazine (25 μL) for 5 min at r.t. followed by and an additional wash with water (25 μL). Both fractions of 25 uL were combined, filtered through a prewashed Mini Quick Spin Oligo Column (Roche) and analyzed directly by LCMS.

General Procedure E: Functionalization of $N^6$mdA in 99 nt ssDNA with the 3-Nitropyridine Probe for Enrichment A 2 mL microwave vial was charged with a mixture of two ODN substrates (methylated and unmethylated, 2 μM in milliQ $H_2O$, 12.5 μL each). In a separate Eppendorf tube, quinuclidine (8.25 mg, 75 μmol) and the 3-nitropyridine probe (0.3 mg, 1.3 μmol) were dissolved using a stock solution of $[Ru(phen)_3]Cl_2$ (3 mM in 1 mL of 30% MeCN in milliQ $H_2O$, 12.5 μL). The latter mixture was then added to the ODN mixture. For the reactions with added salmon sperm DNA, 2 ul of a salmon sperm ssDNA solution (5 mg/ml, abcam ab229278) were added before the photoredox reaction. Final concentrations: ODNs: 0.67 μM each, quinuclidine: 2 M, 3-nitropyridine probe: 33 mM, $[Ru(phen)_3]Cl_2$: 1 mM, 10% MeCN in $H_2O$. The microwave vial was sealed under nitrogen atmosphere after flushing for 15-20 seconds. The vial was then placed inside a 55W CFL bulb. The mixture was irradiated for 5 min while the temperature was maintained with a fan and subsequently filtered through a prewashed Micro BioSpin 6 column (BioRad) after the reaction.

General Procedure F: Click Reaction on the Functionalized $N^6$mdA in 99 nt ssDNA To the resulting ODN mixture from general procedure E in a 1.5 ml Eppendorf tube was added quinuclidine (8.25 mg, 75 μmole in 10 μL $H_2O$), Azide-$PEG_3$-biotin conjugate (20 mM, 7.5 μL), sodium ascorbate (40 mM, 7.5 μL) and $CuSO_4$ (2 mM, 7.5 μL). Final concentrations: quinuclidine: 1 M, Azide-$PEG_3$-biotin conjugate: 2 mM, sodium ascorbate: 4 mM, $CuSO_4$ 0.2 mM. After 30 minutes reaction at r.t., the mixture was filtered twice through a prewashed Micro BioSpin 6 column (BioRad).

General Procedure G: Functionalization of $N^6$mdA in 99 nt dsDNA with the 3-Nitropyridine Probe for Enrichment A 2 mL microwave vial was charged with a mixture of two dsODN substrates (methylated and unmethylated, 0.25-0.35 μM in milliQ $H_2O$, 8.3 μL each). In a separate Eppendorf tube, quinuclidine (5.5 mg, 50 μmol) and the 3-nitropyridine probe (0.2 mg) were dissolved using a stock solution of $[Ru(phen)_3]Cl_2$ (3 mM in 1 mL of 30% MeCN in milliQ $H_2O$, 8.3 μL). The latter mixture was then added to the ODN mixture. For the reactions with added salmon sperm DNA, 2 ul of a salmon sperm ssDNA solution (5 mg/ml, abcam ab229278) were added before the photoredox reaction Final concentrations: ODNs: 0.08-0.12 μM each, quinuclidine: 2 M, 3-nitropyridine probe: 33 mM, $[Ru(phen)_3]Cl_2$: 1 mM, 10% MeCN in $H_2O$. The microwave vial was sealed under nitrogen atmosphere after flushing for 15-20 seconds. The vial was then placed inside a 55W CFL bulb. The mixture was irradiated for 5 min while the temperature was maintained with a fan and subsequently filtered through a prewashed Micro BioSpin 6 column (BioRad) after the reaction.

General Procedure H: Click Reaction on the Functionalized $N^6$mdA in 99 nt dsDNA To the resulting ODN mixture from general procedure E in a 1.5 ml Eppendorf tube was added quinuclidine (5.5 mg, 50 μmol in 5 μL $H_2O$), Azide-$PEG_3$-biotin conjugate (20 mM, 7.5 μL), sodium ascorbate (40 mM, 7.5 μL) and $CuSO_4$ (2 mM, μL). Final concentrations: quinuclidine: 1 M, Azide-$PEG_3$-biotin conjugate: 2 mM, sodium ascorbate: 4 mM, $CuSO_4$ 0.2 mM. After 30 minutes incubation at r.t., the reaction was filtered twice through a prewashed Micro BioSpin 6 column (BioRad).

General Procedure I: Enrichment of $N^6$mdA 99 nt ssDNA and dsDNA ODNs with Streptavidin Magnetic Beads To the resulting ODN mixture from general procedure C (75 or 50 μL) in a 1.5 ml Eppendorf DNA LoBind microcentrifuge tube was added 5× adapted binding buffer (40 μL; 25 mM Tris, 2.5 mM EDTA, 5 M NaCl, pH 8.5), poly[dl:dC](5 μL; 5 μg/μl), and water (80 or 105 μL, to a total volume of 200 μL). Streptavidin MagneSphere® Paramagnetic Particles (100 μL of a 1 mg/ml suspension) were separated from the storage buffer on a magnetic stand, washed twice with 0.5×SSC buffer (200 μL; 75 mM NaCl, 7.5 mM sodium citrate, pH 7.2) and once with 1× adapted binding buffer (200 μL; 5 mM Tris, 0.5 mM EDTA, 1 M NaCl, pH 8.5) with poly[dl:dC](5 μL; 5 μg/μL). The oligo solution (200 μL) was added to the prewashed paramagnetic particles and after 10 minutes incubation at r.t. the supernatant was collected for the quantification of both ODN sequences by qPCR. The beads were washed three times with 1× adapted binding buffer (3×200 μL), then transferred into a new microcentrifuge tube with 200 uL adapted binding buffer and washed another time with adapted binding buffer (200 μL). They were then incubated in 100 mM NaOH at r.t. for 10 min three times (3××200 μL), and finally washed again three times with adapted binding buffer (3×200 μL). Elution of the bound oligonucleotides was performed by incubation with 10% aqueous hydrazine (25 μL) at r.t. for 5 min. After an additional wash of the paramagnetic particles with water (25 μL), both fractions were combined, purified using Zymo Oligo Clean & Concentrator™ spin columns (according to the manufacturers protocol) and the oligonucleotides eluted with 15 μL milliQ water. 7.5 μL of this purified fraction was kept for the determination of enrichment factors by quantifying both ODN sequences by qPCR. The other 7.5 μL were diluted with 5× adapted binding buffer (10 μL) and water (32.5 μL) and treated with prewashed Streptavidin MagneSphere® Paramagnetic Particles (100 μL of a 1 mg/ml suspension) to remove any residue of unselectively biotinylated oligonucleotides. The supernatant was purified using Zymo Oligo Clean & Concentrator™ spin columns according to the manufacturers protocol and the oligonucleotides eluted with 15 μL milliQ water. The enrichment factor was determined by quantifying both ODN sequences by qPCR.

Synthesis and Characterization of Derivatives of Quinuclidine and 3-nitropyridine Compounds General Procedure J: Suzuki Coupling of Aryl Boronic Acids to Chloro- or Bromo-3-Nitropyridines The appropriate chloro- or bromo-3-nitropyridine and arylboronic acid were dissolved in a 1:1 (v/v) mixture of THF and 20% (wt) $Na_2CO_3$ in $H_2O$ under an atmosphere of argon. Tetrakis(triphenylphosphine)palladium(0) (10-20 mol %) was added and the mixture was refluxed for 2 h. After dilution with $H_2O$ the mixture was extracted with $CH_2Cl_2$ (3×). The combined organic layers were dried ($MgSO_4$) and the solvents evaporated. Crude products were purified by flash column chromatography.

General Procedure K: Amide Couplings of Aromatic Amines or Carboxylic Acids with 5-hexynoic Acid or Propargylamine/4-pentyne-1-amine The appropriate carboxylic acid (1 equiv.), amine (1 equiv.) and $Et_3N$ (1 equiv.) were dissolved in dry DMF under an atmosphere of argon. The mixture was cooled to 0° C. and pyBOP (1 equiv.) was added. The mixture was stirred overnight, allowing it to slowly reach r.t. It was then diluted with $H_2O$ and extracted with EtOAc. The combined organic layers were dried ($MgSO_4$) and the solvents evaporated. Crude products were purified by flash column chromatography.

(3-(hex-5-ynamido)phenyl)boronic acid

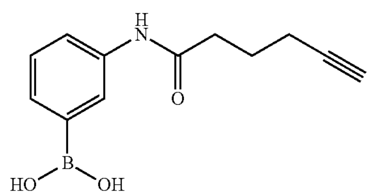 [SMILES: C#CCCCC(=O)Nc1cccc(B(O)O)c1]

Synthesised according to General Procedure K from 3-aminophenylboronic acid monohydrate (310 mg, 2.0 mmol) and 5-hexynoic acid (0.22 ml, 2.0 mmol) to afford the product as a white solid containing 15 mol % tripyrrolidinophosphine oxide (344 mg, 1.3 mmol, 67%) which was used without further purification for subsequent suzuki couplings.

$^1$H NMR (400 MHz, Methanol-$d_4$) δ (ppm) 7.84-7.72 (m, 1H), 7.61 (d, J=7.3 Hz, 1H), 7.51-7.22 (m, 2H), 3.14 (td, J=6.6, 3.7 Hz, 2H), 2.50 (t, J=7.5 Hz, 2H), 2.32-2.23 (m, 1H), 1.88 (p, J=7.3 Hz, 2H). $^{13}$C NMR (101 MHz, Methanol-$d_4$) δ (ppm) 173.8, 139.2, 130.2, 129.1, 126.2, 122.6, 84.1, 70.3, 36.6, 25.7, 18.7 (one quaternary aromatic C not detected). HMRS-ESI (m/z): found [M+H]$^+$ 232.1135, $C_{12}H_{15}BNO_3$ requires 232.1140.

N-(3-(5-nitropyidin-2-yl)phenyl)hex-5-ynamide

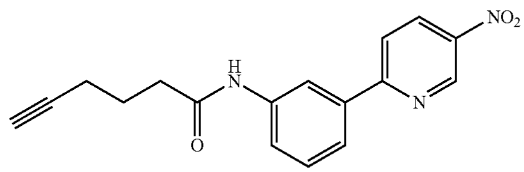 [SMILES: C#CCCCC(=O)Nc1cccc(-c2ccc([N+](=O)[O-])cn2)c1]

Synthesised according to General Procedure J from 2-bromo-5-nitropyridine (102 mg, 0.5 mmol) and (3-(hex-5-ynamido)phenyl)boronic acid (116 mg, 0.5 mmol) to afford the product as a pale yellow solid (52 mg, 0.17 mmol, 34%).

$^1$H NMR (400 MHz, $CDCl_3$) δ (ppm) 9.48 (dd, J=2.7, 0.6 Hz, 1H), 8.53 (dd, J=8.8, 2.7 Hz, 1H), 8.35 (app s, 1H), 7.94 (dd, J=8.8, 0.6 Hz, 1H), 7.83 (app d, J=8.0 Hz, 1H), 7.68 (app d, J=8.0 Hz, 1H), 7.49 (t, J=8.0 Hz, 1H), 7.42-7.32 (bs, 1H), 2.57 (t, J=7.3 Hz, 2H), 2.36 (td, J=6.8, 2.6 Hz, 2H), 2.04 (t, J=2.6 Hz, 1H), 1.99 (qnt, J=7.1 Hz, 2H); $^{13}$C NMR (101 MHz, $CDCl_3$) δ (ppm) 170.9, 162.0, 145.3, 143.2, 138.9, 138.0, 132.1, 130.0, 123.6, 122.1, 120.4, 119.0, 83.5, 70.0, 36.1, 24.0, 17.9; HMRS-ESI (m/z): found [M+H]$^+$ 310.1188, $C_{17}H_{18}N_3O_3$ requires 310.1186.

N-(3-(5-nitropyridin-3-yl)phenyl)hex-5-ynamide

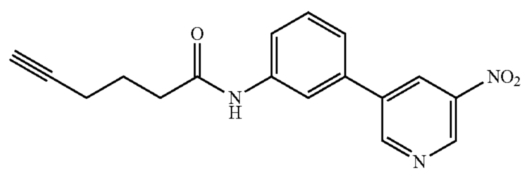 [SMILES: C#CCCCC(=O)Nc1cccc(-c2cncc([N+](=O)[O-])c2)c1]

Synthesised according to General Procedure J from 3-bromo-5-nitropyridine (51 mg, 0.25 mmol) and (3-(hex-5-ynamido)phenyl)boronic acid (53 mg, 0.23 mmol) to afford the product as a pale orange solid (46 mg, 0.15 mmol, 65%).

$^1$H NMR (400 MHz, $CDCl_3$) δ (ppm) 9.42 (d, J=2.4 Hz, 1H), 9.13 (d, J=2.0 Hz, 1H), 8.66 (app. t, J=2.3 Hz, 1H), 8.01 (app. s, 1H), 7.52-7.42 (m, 3H), 7.37 (d, J=7.0 Hz, 1H), 2.58 (t, J=7.3 Hz, 2H), 2.36 (td, J=6.7, 2.6 Hz, 2H), 2.03 (t, J=2.6 Hz, 1H), 1.97 (app. q, J=7.0 Hz, 2H). $^{13}$C NMR (101 MHz, $CDCl_3$) δ (ppm) 171.0, 153.2, 144.6, 143.6, 139.1, 137.4, 136.2, 130.3, 129.3, 123.2, 120.5, 118.7, 83.5, 69.7, 36.1, 23.9, 17.9. HMRS-ESI (m/z): found [M+H]$^+$ 310.1181, $C_{17}H_{16}N_3O_3$ requires 310.1186.

N-(3-(3-nitropyridin-4-yl)phenyl)hex-5-ynamide

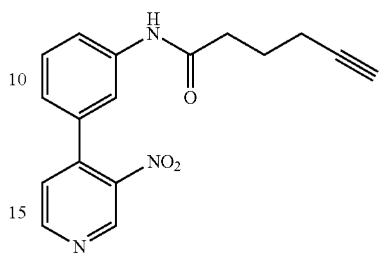

Synthesised according to General Procedure J from 4-chloro-3-nitropyridine (150 mg, 0.95 mmol) and (3-(hex-5-ynamido)phenyl)boronic acid (200 mg, 0.87 mmol) to afford the product as an off-white solid (187 mg, 0.61 mmol, 70%).

$^1$H NMR (400 MHz, $CDCl_3$) δ (ppm) 9.08 (s, 1H), 8.81 (d, J=5.0 Hz, 1H), 7.70 (app s, 1H), 7.51 (app d, J=8.4 Hz, 1H), 7.43 (d, J=5.8 Hz, 1H), 7.41 (t, J=8.0 Hz, 1H), 7.36-7.31 (bs, 1H), 7.07 (app d, J=7.8 Hz, 1H), 2.54 (t, J=7.3 Hz, 2H), 2.34 (td, J=6.8, 2.6 Hz, 2H), 2.02 (t, J=2.6 Hz, 1H), 1.96 (qnt, J=7.0 Hz, 2H); $^{13}$C NMR (101 MHz, $CDCl_3$) δ (ppm) 170.7, 152.9, 145.5, 145.2, 134.5, 129.7, 125.8, 123.4, 120.6, 118.9, 83.3, 69.6, 35.9, 23.7, 17.8; HMRS-ESI (m/z): found [M+H]$^+$ 310.1189, $C_{17}H_{16}N_3O_3$ requires 310.1186.

3-(3-nitropyridin-4-yl)benzoic acid

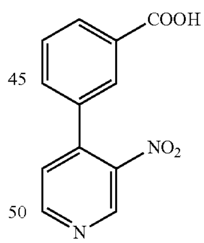

Synthesised according to General Procedure J from 4-chloro-3-nitropyridine (200 mg, 1.26 mmol) and 3-carboxyphenylboronic acid (231 mg, 1.39 mmol) with extended reaction time (reflux for 20 h) to afford the product as a pale orange solid (162 mg, 0.60 mmol, 47%).

$^1$H NMR (500 MHz, $CDCl_3$) δ (ppm) 9.19 (s, 1H), 8.88 (d, J=5.0 Hz, 1H), 8.23 (d, J=7.5 Hz, 1H), 8.11 (s, 1H), 7.61 (app. t, J=7.5 Hz, 1H), 7.57 (d, J=7.8 Hz, 1H), 7.45 (d, J=4.9 Hz, 1H). $^{13}$C NMR (126 MHz, $CDCl_3$) δ 168.9, 153.1, 145.6, 145.1, 143.1, 135.2, 132.7, 131.2, 130.1, 129.4, 129.3, 125.8. HMRS-ESI (m/z): found [M+H]$^+$ 245.0551, $C_{12}H_9N_2O_4$ requires 245.0557.

3-(3-nitropyridin-4-yl)-N-(pent-4-yn-1-yl)benzamide

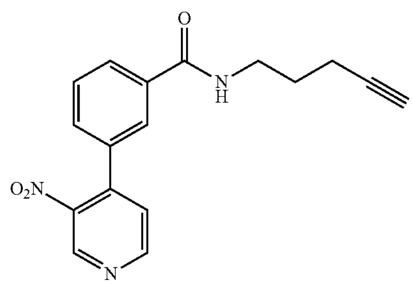 [SMILES: C#CCCCNC(=O)c1cccc(-c2ccncc2[N+](=O)[O-])c1]

Synthesised according to General Procedure K from 3-(3-nitropyridin-4-yl)benzoic acid (18 mg, 0.074 mmol) and 4-pentyne-1-amine hydrochloride (11 mg, 0.089 mmol) to afford the product as an off-white solid (17 mg, 0.055 mmol, 74%).

$^1$H NMR (500 MHz, $CDCl_3$) δ (ppm) 9.15 (s, 1H), 8.85 (d, J=5.0 Hz, 1H), 7.83 (ddd, J=7.7, 1.8, 1.1 Hz, 1H), 7.80 (dt, J=1.8, 0.9 Hz, 1H), 7.54 (td, J=7.7, 0.6 Hz, 1H), 7.46-7.41 (m, 2H), 6.47 (app. s, 1H), 3.61 (td, J=6.7, 5.8 Hz, 2H), 2.34 (td, J=6.8, 2.7 Hz, 2H), 2.03 (t, J=2.7 Hz, 1H), 1.88 (app. p, J=6.8 Hz, 2H); $^{13}$C NMR (126 MHz, $CDCl_3$) δ 166.8, 153.2, 145.6, 145.3, 143.5, 135.8, 135.4, 130.6, 129.4, 127.7, 126.7, 126.0, 83.76, 69.7, 39.7, 28.0, 16.5; HMRS-ESI (m/z): found $[M+H]^+$ 310.1182, $C_{17}H_{16}N_3O_3$ requires 310.1186.

5-nitro-N-(pent-4-yn-1-yl)picolinamide

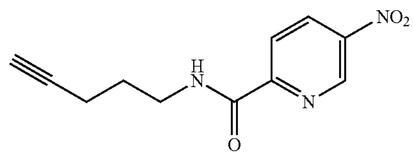 [SMILES: C#CCCCNC(=O)c1ccc([N+](=O)[O-])cn1]

Synthesised according to General Procedure K from 5-nitropyridine-2-carboxylic acid (141 mg, 0.84 mmol) and 4-pentyne-1-amine hydrochloride (100 mg, 0.84 mmol) to afford the product as an off-white solid (166 mg, 0.71 mmol, 85%).

$^1$H NMR (400 MHz, $CDCl_3$) δ (ppm) 9.37 (d, J=2.5 Hz, 1H), 8.64 (dd, J=8.5, 2.3 Hz, 1H), 8.42 (d, J=8.5 Hz, 1H), 8.16 (app. s, 1H), 3.64 (app. q, J=6.6 Hz, 2H), 2.33 (td, J=6.9, 2.6 Hz, 2H), 2.02 (t, J=2.6 Hz, 1H), 1.90 (app. p, J=6.9 Hz, 2H); $^{13}$C NMR (101 MHz, $CDCl_3$) δ (ppm) 162.4, 154.2, 145.7, 143.9, 132.9, 123.0, 83.2, 69.6, 39.0, 28.2, 16.3; HMRS-ESI (m/z): found $[M+H]^+$ 234.0868, $C_{11}H_{12}N_3O_3$ requires 234.0879.

N-(5-nitropyridin-3-yl)hex-5-ynamide, 2b

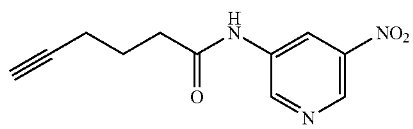 [SMILES: C#CCCCC(=O)Nc1cncc([N+](=O)[O-])c1]

Synthesised according to General Procedure K from 3-amino-5-nitropyridine (139 mg, 1.00 mmol) and 5-hexynoic acid (0.11 ml, 1.00 mmol) to afford the product as a pale orange solid (96 mg, 0.41 mmol, 41%). $^4$H NMR (400 MHz, $CDCl_3$) δ (ppm) 9.16 (d, J=2.3 Hz, 1H), 9.02 (app. t, J=2.5 Hz, 1H), 8.90 (d, J=2.3 Hz, 1H), 7.68 (s, 1H), 2.63 (t, J=7.2 Hz, 2H), 2.36 (td, J=6.7, 2.7 Hz, 2H), 2.04 (t, J=2.7 Hz, 1H), 1.99 (app. p, J=7.0 Hz, 2H); $^{13}$C NMR (101 MHz, $CDCl_3$) δ (ppm) 171.9, 145.1, 143.2, 137.3, 136.9, 123.2, 83.2, 70.0, 35.9, 23.57, 17.9; HMRS-ESI (m/z): found $[M+H]^+$ 234.0876, $C_{11}H_{12}N_3O_3$ requires 234.0879.

5-nitro-N-(prop-2-yn-1-yl)picolinamide

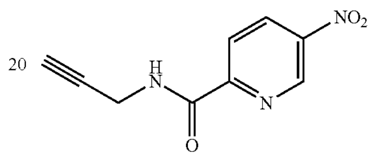

Synthesised according to General Procedure K from 5-nitropyridine-2-carboxylic acid (141 mg, 0.84 mmol) and propargylamine (54 µl, 0.84 mmol) to afford the product as a pale yellow solid (124 mg, 0.60 mmol, 72%).

$^1$H NMR (400 MHz, $CDCl_3$) δ (ppm) 9.39 (d, J=2.5 Hz, 1H), 8.65 (dd, J=8.6, 2.5 Hz, 1H), 8.42 (d, J=8.6 Hz, 1H), 8.15 (app. s, 1H), 4.30 (dd, J=5.6, 2.6 Hz, 2H), 2.31 (t, J=2.6 Hz, 1H); $^{13}$C NMR (101 MHz, $CDCl_3$) b (ppm) 162.0, 153.6, 145.9, 144.0, 132.9, 123.2, 78.8, 72.3, 29.7; HMRS-ESI (m/z): found $[M+H]^+$ 206.0557, $C_9H_8N_3O_3$ requires 206.0566.

Enzymatic Synthesis of N$^6$mdA-Containing dsDNA dsDNA was synthesised enzymatically by primer elongation with Vent® DNA Polymerase (NEB) using a non-methylated template (sequences see below), the according reverse primer (sequences see below) and either a set of canonical dNTPs (to synthesise non-methylated dsDNA) or a mixture dCTP, dGTP, N$^6$mdATP and dTTP (to synthesise dsDNA with N$^6$mdA at the indicated positions in bold).

SEQ ID NO 1: DNA Template 1
AACGGAAGCAGAACAGAACGAAGCAAGACGAGCAACACGAACAGAACAC
GAAACGATGCAAGAGAGCAAGCAAGCAACGTTCGTTGCTGTTCGCTGTT
G SEQ ID NO 2: DNA Template 2
AACGAAGCAGAACGCAGAAGAAGCAAGACGACCAACACGTACGGAACAC
GAAACGAAGCATGCGCCGAAGCAAGCCACGTTCGGTTGCTGTTCTGTTC
G SEQ ID NO 3: Reverse primer 1
CAACAGCGAACAGCAACGAA SEQ ID NO 4: Reverse primer 2
CGAACAGAACAGCAACCGAA SEQ ID NO 5: Oligonucleotide 5
CTTGACAG[N$^6$mdA]CTAG SEQ ID NO 6: 41nt ssDNA
GCGC TTGG CTGG TGGG TGAT TCTG CAAC TC[N$^6$mdA]G ATCA
TGCT A A series of 5-10 parallel reactions were run with following optimised concentrations:

| Reagent | Final c/amount |
|---|---|
| template | 0.5 μg |
| primer | 10 μM |
| Vent ® DNA Polymerase (NEB) | 2 U |
| ThermoPol ® Reaction buffer (NEB) | 1X |
| dATP or $N^6$m-dATP | 2 mM |
| dCTP | 2 mM |
| dGTP | 2 mM |
| dTTP | 2 mM |
| $H_2O$ | for a final volume of 20 μL |

The reactions were run using the following optimised temperature cycle:

| Step | Time | Temperature |
|---|---|---|
| melting/denaturing | 30 sec | 95° C. |
| primer annealing | 1 min | 60° C. |
| polymerization | 10 min | 72° C. |
| storage | inf. | 4° C. |

Upon reaction, the parallel PCR reactions were combined and the PCR products purified with the GeneJet PCR purification kit (Thermo Scientific) according to the manufacturer's protocol (without the use of iPrOH). The products were analysed by automated gel electrophoresis (Tapestation) and LCMS to confirm the identity of the synthesised strands.

2. Results

Nucleic acids can contain several types of $C(sp^3)$-H bonds, each with subtly different intrinsic reactivities that can be influenced by steric, inductive and conjugative effects imparted by the proximal chemical environment. Discrimination of these $C(sp^3)$-H bonds using a chemical reagent, however, presents a significant challenge. The C—H bonds in $N^6$mdA's methyl group can have fairly high bond dissociation energies (BDE, -92-94 kcal/mol) (Dombrowski 1999). Moreover, such a reagent will need to target a strong C—H bond that may be present at extremely low effective concentration (N6mdA levels in eukaryotes may be as low as a few parts per million $N^6$mdA/A), amongst a plethora of similar strength or weaker C—H bonds: for example, deoxyribose units contain many different C—H bonds, each with similar BDE's; and the methyl group in thymidine (and epigenetically-marked 5-methylcytosine) displays activated C—H bonds with lower BDE (~89-90 kcal/mol) (Blanksby 2003). Alongside these essential selectivity requirements, the $N^6$mdA functionalization strategy should productively intercept the 'on-DNA' α-amino-radical to fashion a stable covalent linkage to the oligonucleotide. The challenges associated with addressing these problems are multifaceted: firstly, use of a proximity-driven rebound mechanism thought to facilitate enzymatic demethylation is unlikely to be feasible in a synthetic scenario and so the coupling step should be fast in order to accommodate the likely short lifetime of the DNA-derived α-amino-radical; and secondly, the HAA and covalent functionalization steps should operate in concert without displaying deleterious and non-selective reactivity. These difficulties place additional constraints on potential chemical solutions that should already operate at low concentrations, in aqueous solutions and avoiding acidic or oxidative conditions, which might damage the DNA architecture.

It was recognized that C—H bonds in the methyl group of $N^6$mdA would likely be partially polarized as a result of their interaction with the lone pair on the N6-atom and display a 'hydridic' character (Roberts 1999; Jeffrey 2015) (FIG. 1A).

In contrast, it was recognized that the C—H bonds of in the methyl group of thymine, although weaker, are relatively neutral as a result of being adjacent to the less polarizing pyrimidine heterocycle. This subtle electronic effect may provide a sufficiently distinct reactivity profile to enable a kinetically-controlled polarity match between an electrophilic hydrogen atom abstracting agent and the more hydridic C—H bonds in the N6-methylamine motif in $N^6$mdA. The resulting C—H bond cleavage can lead to formation of an α-amino radical on the modified nucleotide. The intercepting reagent can react quickly with the incipient $N^6$mdA-derived α-amino radical and form an open shell species more stable than its precursor. It was reasoned that deployment of a spin trapping reagent could provide a potential solution to this challenge. Spin trapping reagents (STRs) are highly reactive molecules, used in excess quantities to capture radicals in the form of persistent radical products, which can enable the identification of short-lived species in complex systems. Among STRs, nitrosoarenes are particularly suitable for the interception of nucleophilic carbon-centered radicals, the properties of which should be inherent to an $N^6$mdA-derived α-amino radical (FIG. 1B).

Nitrosoarene-derived STRs are, however, highly electrophilic and often display promiscuous non-radical reactivity with nucleophiles, can undergo facile dimerization and readily decompose to non-productive products. To compound these problems, a nitrosoarene must also be compatible with the HAA step, itself a radical reaction, without displaying deleterious reactivity. These problems could be circumvented if a process could be designed wherein the STR was generated in situ as a consequence of chemistry required to facilitate the HAA step, thereby closely linking the proximity of this reactive species to the incipient $N^6$mdA-derived radical. Accordingly, it was hypothesized that a mild method to reduce a water-soluble nitroarene might be leveraged alongside the HAA step for the in situ generation of a nitrosoarene STR and lead to a selective functionalization process.

Quinuclidine radical cation (int I), generated from quinuclidine 1, was chosen as an electrophilic hydrogen atom abstractor for $N^6$mdA (FIG. 1C).

Protonated quinuclidine has a BDE of 101 kcal/mol (Liu 1996) meaning that its radical cation will be sufficiently reactive to remove a hydrogen atom from the $N^6$mdA-methyl group. The quinuclidine radical cation may be generated under mild reaction conditions via Ir-catalyzed photoredox-mediated single electron oxidation and displays polarity-matched reactivity for strong electron-rich C—H bonds. It was speculated that $Ru(bpz)_3(PF6)_2$ could function as a suitable photocatalyst because it displays adequate aqueous solubility and the reductive quenching cycle of its triplet excited-state is well matched to the oxidation potential of quinuclidine (E[Ru(II)*/Ru(I)]=1.45 V compared to quinuclidine $E^{ox}$=1.10 V vs SCE). Therefore, a reductive quenching cycle can generate int I, which could engage $N^6$mdA through selective HAA to form the desired α-amino radical (int 11). Consequently, the reductive quenching cycle can produce $[Ru(I)(bpz)_3]$-, a species which requires oxidation back to the active catalyst. This mechanistic requirement could be exploited using 3-nitropyridine 2a, a water-soluble organic oxidant, to accept an electron from [Ru(I)$(bpz)_3$]-($E^{red}$=−0.44 V vs SCE estimated for 4-nitropyridine), thereby producing a radical anion int III (as well as returning the active catalyst). The nitropyridine radical anion may undergo hydrogen atom transfer with the bulk solvent (or perhaps $N^6$mdA) to int IV and eliminate water to form the STR, 3-nitrosopyridine 3a. Crucially, the concentration of the 3-nitrosopyridine (3a) can be controlled by the photochemical activity of the catalyst, avoiding the presence of potentially deleterious super-stoichiometric levels of STR. Reaction of 3-nitrosopyridine with the $N^6$mdA-derived α-amino radical int II can then generate a nitroxide persistent radical (int V), which can ultimately undergo oxidative decay to fashion a covalent modification at the N6-position of the nucleobase in the form of a N-hydroxyformamidine linkage 4.

Figure 2:
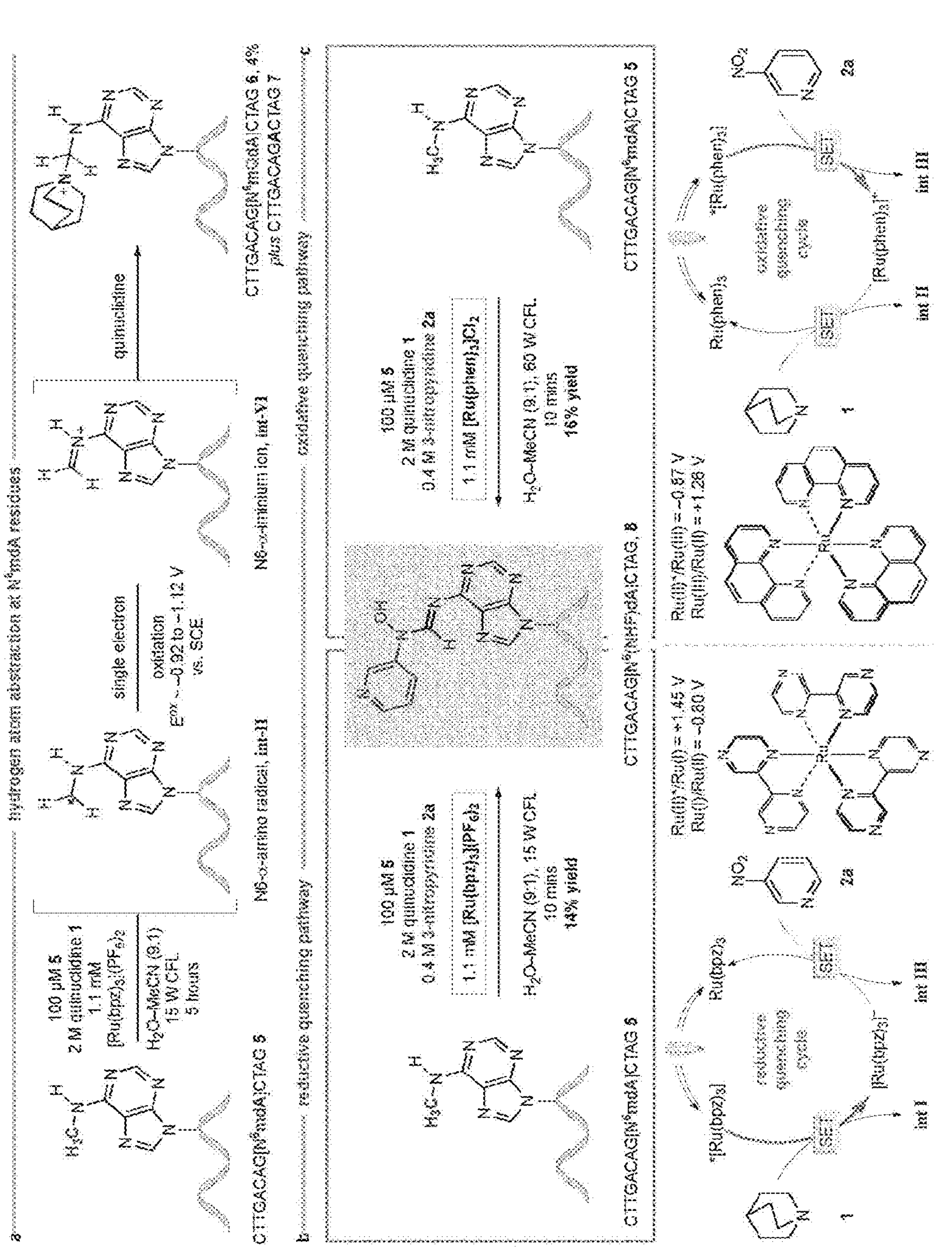
FIG. 2 is a schematic overview of the visible light-mediated photoredox strategy for covalent functionalization of N6mdA. a) Shows the HAA on the N6-methyl group of N6mdA. b) Shows the conjugation via HAA and radical trapping via a reductive photocatalytic quenching cycle with $[Ru(II)(bpz)_3](PF6)_2$ on an oligonucleotide comprising $N^6$mdA. c) Shows the conjugation via HAA and radical trapping via a oxidative photocatalytic quenching cycle with $[Ru(II)(phen)_3]Cl_2$ on an oligonucleotide comprising $N^6$mdA.

The initial studies focussed on establishing a HAA protocol on a representative oligonucleotide 5 (CTTGACAG[$N^6$mdA]CTAG). A series of exploratory experiments revealed that irradiation of a solution of 5, 1 and [Ru$(bpz)_3$]$(PFe)_2$ with a 15 W CFL bulb for 5 hours at room temperature, led to the formation of oligonucleotide 6 with 4% conversion to product, wherein a single quinuclidine molecule had been covalently incorporated, as determined by LC-MS analysis (FIG. 2A).

The conjugation to 6 was also accompanied by the formation of some demethylated-oligonucleotide (CTTGACAGACTAG 7, 16%). The formation of 6 and 7 is consistent with an α-amino radical int-II formed at the N6 group of $N^6$mdA and subsequent reaction through iminium ion int-VI, which can react with quinuclidine to form the modified oligonucleotide (6) or be hydrolyzed (demethylating to 7). Encouraged by the validation of the HAA step, the in situ generation of the nitrosoarene STR 3a from 3-nitropyridine 2a and its interception of the $N^6$mdA-derived α-amino radical was investigated next. It was found that irradiation of a solution of oligonucleotide 5, quinuclidine, [Ru$(bpz)_3$]$(PF6)_2$ and 3-nitropyridine 2a for 10 minutes at room temperature produced conjugate 8; 8 was identified by LC-MS analysis with 14% conversion to product and arises from the formal dehydrative coupling of 3-nitropyridine with the $N^6$mdA to form a N-hydroxyformamidine linkage (Table 1). The conjugation to 8 was again accompanied by the formation of demethylated-oligonucleotide 7 (26%). The oligonucleotide conjugate 8 has a half-life of approximately 12 hours at room temperature in neutral or basic solutions (pH=7-11).

Reaction conditions and yields for the selective functionalization reactions of $N^6$mdA ODN 5 with different 3-nitropyridine derivatives are shown below in Scheme 1 and Table 1.

Scheme 1

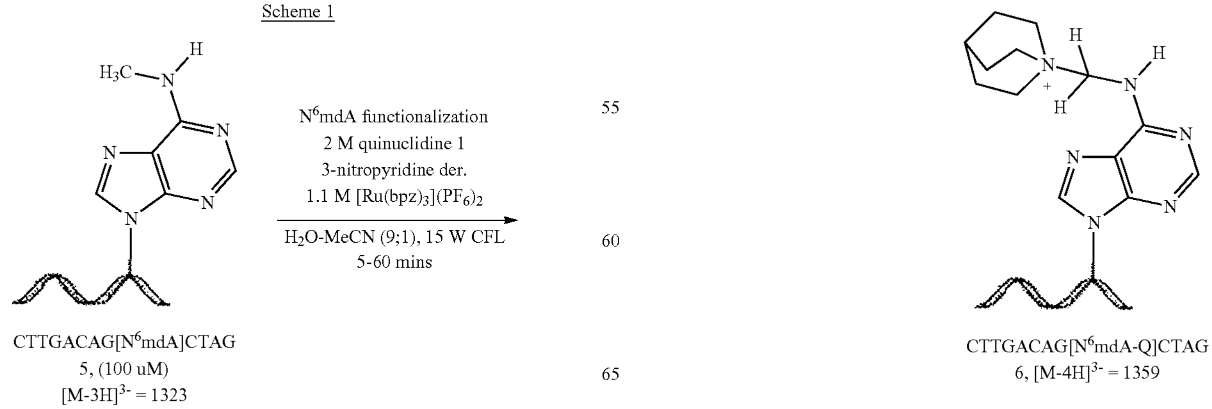

CTTGACAG[$N^6$mdA]CTAG
5, (100 uM)
$[M-3H]^{3-}$ = 1323

CTTGACAG[$N^6$mdA-Q]CTAG
6, $[M-4H]^{3-}$ = 1359

-continued

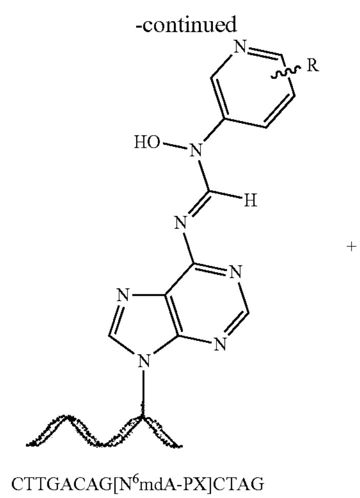

CTTGACAG[$N^6$mdA-PX]CTAG

+

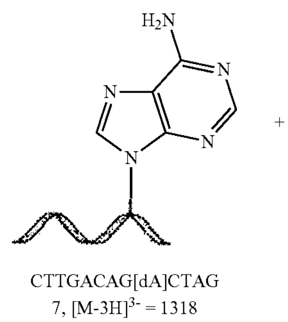

CTTGACAG[dA]CTAG
7, $[M-3H]^{3-}$ = 1318

+

TABLE 1
| 3-Nitropyridine der. | [c] | Reaction time[a] | Yield $[N^6mdA\text{-}PX]^b$ (m/z $[M-3H]^{3-}$) | Yield $[dA]^b$ | Yield $[N^6mdA\text{-}Q]^b$ |
|---|---|---|---|---|---|
| 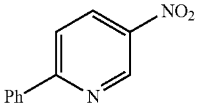 [SMILES: O=[N+]([O-])c1ccc(-c2ccccc2)nc1] | 0.4M | 1 h<br>15 W CFL | 5%<br>(1384) | 15% | 2% |
| 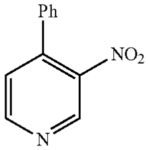 [SMILES: O=[N+]([O-])c1cnccc1-c1ccccc1] | 0.4M | 1 h<br>15 W CFL | 7%<br>(1384) | 17% | 2% |
| 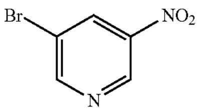 | 0.4M | 10 min<br>15 W CFL | 4%<br>(1385) | 38% | 3% |
| 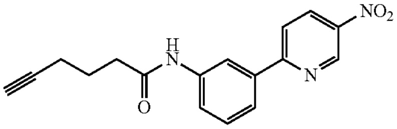 [SMILES: C#CCCCC(=O)Nc1cccc(-c2ccc([N+](=O)[O-])cn2)c1] | 0.2M | 1 h<br>15 W CFL | 2%<br>(1420) | 11% | 3% |
| 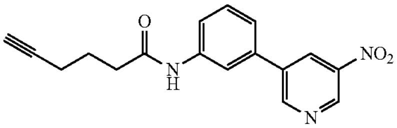 [SMILES: C#CCCCC(=O)Nc1cccc(-c2cncc([N+](=O)[O-])c2)c1] | 0.13M | 1 h<br>15 W CFL | 1%<br>(1420) | 19% | 2% |
| 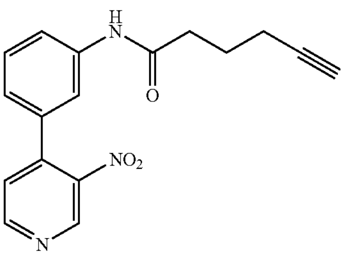 [SMILES: C#CCCCC(=O)Nc1cccc(-c2ccncc2[N+](=O)[O-])c1] | 0.13M | 1 h<br>15 W CFL | 2%<br>(1420) | 13% | 2% |
| 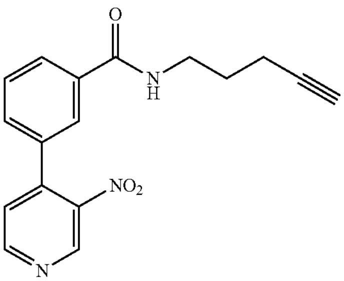 [SMILES: C#CCCCNC(=O)c1cccc(-c2ccncc2[N+](=O)[O-])c1] | 0.08M | 1 h<br>15 W CFL | 3%<br>(1420) | 28% | 2% |
| 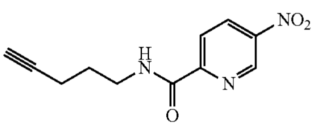 [SMILES: C#CCCCNC(=O)c1ccc([N+](=O)[O-])cn1] | 0.1M | 20 min<br>15 W CFL | 7%<br>(1394) | 35% | 1% |
| 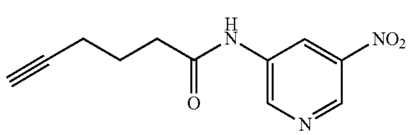 [SMILES: C#CCCCC(=O)Nc1cncc([N+](=O)[O-])c1] | 0.1M | 20 min<br>15 W CFL | 8%<br>(1394) | 17% | 5% |

TABLE 1-continued

| 3-Nitropyridine der. | [c] | Reaction time[a] | Yield $[N^6mdA-PX]^b$ (m/z $[M-3H]^{3-}$) | Yield $[dA]^b$ | Yield $[N^6mdA-Q]^b$ |
|---|---|---|---|---|---|
| 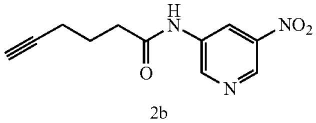 2b | 0.1M | 20 min 60 W CFL | 17% (1394) | 37% | 2% |
| 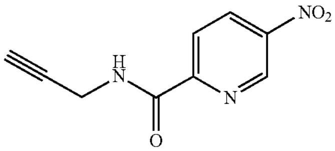 | 0.1M | 20 min 15 W CFL | 8%[c] (1385) | 25% | 2%[c] |

[a]other reaction conditions according to General Procedure B
[b]assay yields by LCMS
[c]species coeluting in LCMS, approximate yields according to MS signal intensities While the photocatalytic process can proceed via a reductive quenching cycle (FIGS. 1C and 2B), the transformation can also be affected by a complementary oxidative quenching cycle, effectively reversing the order of engagement of the reaction partners, if a more reducing photocatalyst, such as $Ru(phen)_3Cl_2$ was used (E[Ru(II)*/Ru(III)]=−0.87 V).

In this case, 3-nitropyridine 2a would oxidatively quench the triplet excited state form of the photocatalyst to first generate radical anion, nitrosoarene precursor int III, (FIG. 2B) alongside a $[Ru(III)(phen)_3]$ intermediate, which would subsequently engage quinuclidine 1 to form the radical cation int I needed for the HAA step.

Figure 3:
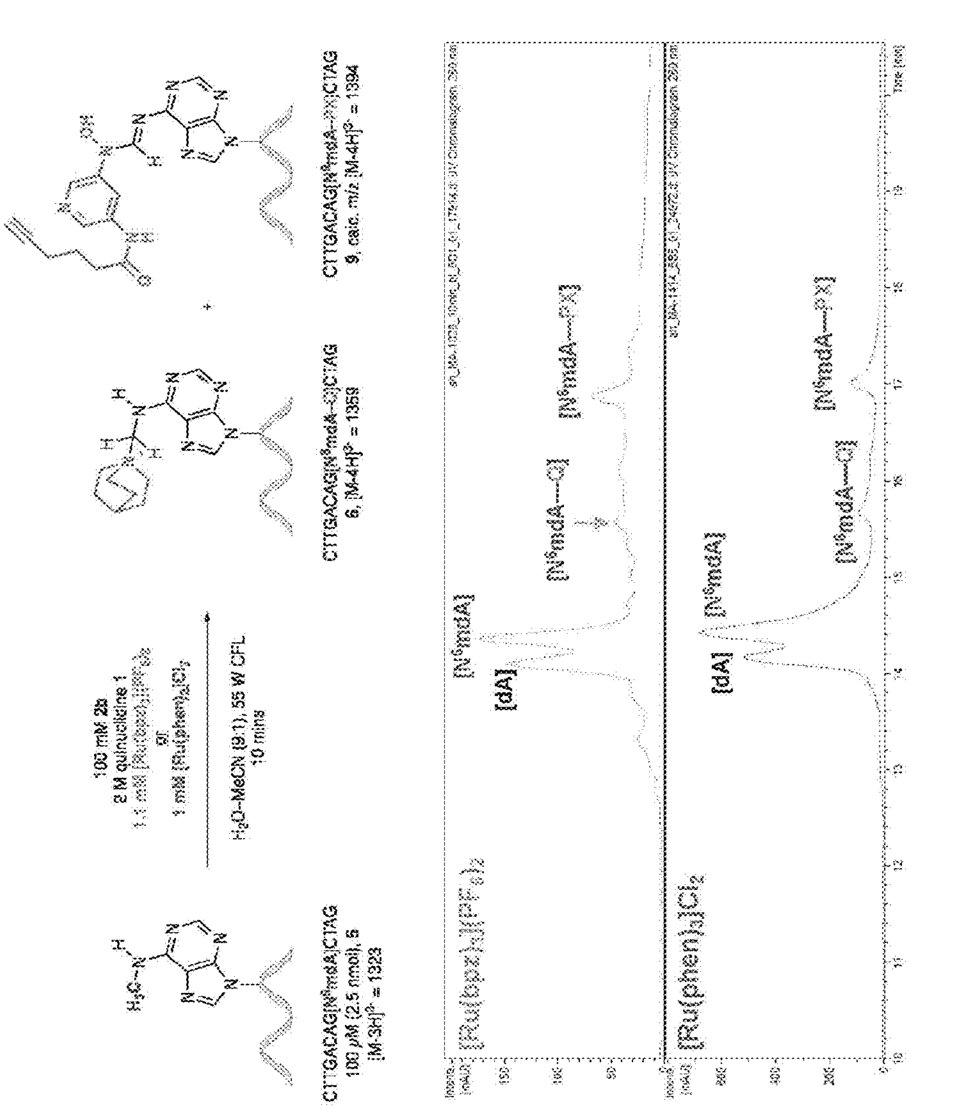
FIG. 3 shows a reaction scheme and LCMS trace of the $N^6$mAde functionalization in ODN 5 using the reductive quenching pathway of $[Ru(bpz)_3](PFe)_2$ (upper trace) and the oxidative quenching of $[Ru(phen)_3]Cl_2$ (lower trace).

Consequently, it was found that irradiation of a reaction with $Ru(phen)_3C_{12}$ as catalyst furnished the desired N-hydroxyformamidine-$N^6$mdA oligonucleotide conjugate 8 with 16% conversion to product. A 30% conversion to the de-methylated oligonucleotide 7 was also observed. It is notable that the $[Ru(III)(phen)_3]$ species formed during the oxidative quenching step has lower oxidizing power (E[Ru (III)/Ru(II)]=+1.26 V) than the triplet excited state intermediate formed from the $Ru(II)(bpz)_3$ photocatalyst in the corresponding reductive quenching cycle (E[Ru(II)*/Ru(I)] =+1.45 V), yet is still sufficiently reactive to oxidize quinuclidine to its radical cation and regenerate photocatalyst. The lower oxidizing power of the $Ru(III)(phen)_3$ intermediate together with the constant oxidative quenching of triplet excited state of $[Ru(III)(phen)_3]$ by 3-nitropyridine and high concentration of quinuclidine may prevent oxidative damage of DNA, especially at G nucleobases. This is reflected in the observation that the transformation using the $Ru(phen)_3C_{12}$ as catalyst produces a cleaner reaction profile compared to the use of $[Ru(II)(bpz)_3](PF6)_2$ (FIG. 3).

Figure 4:
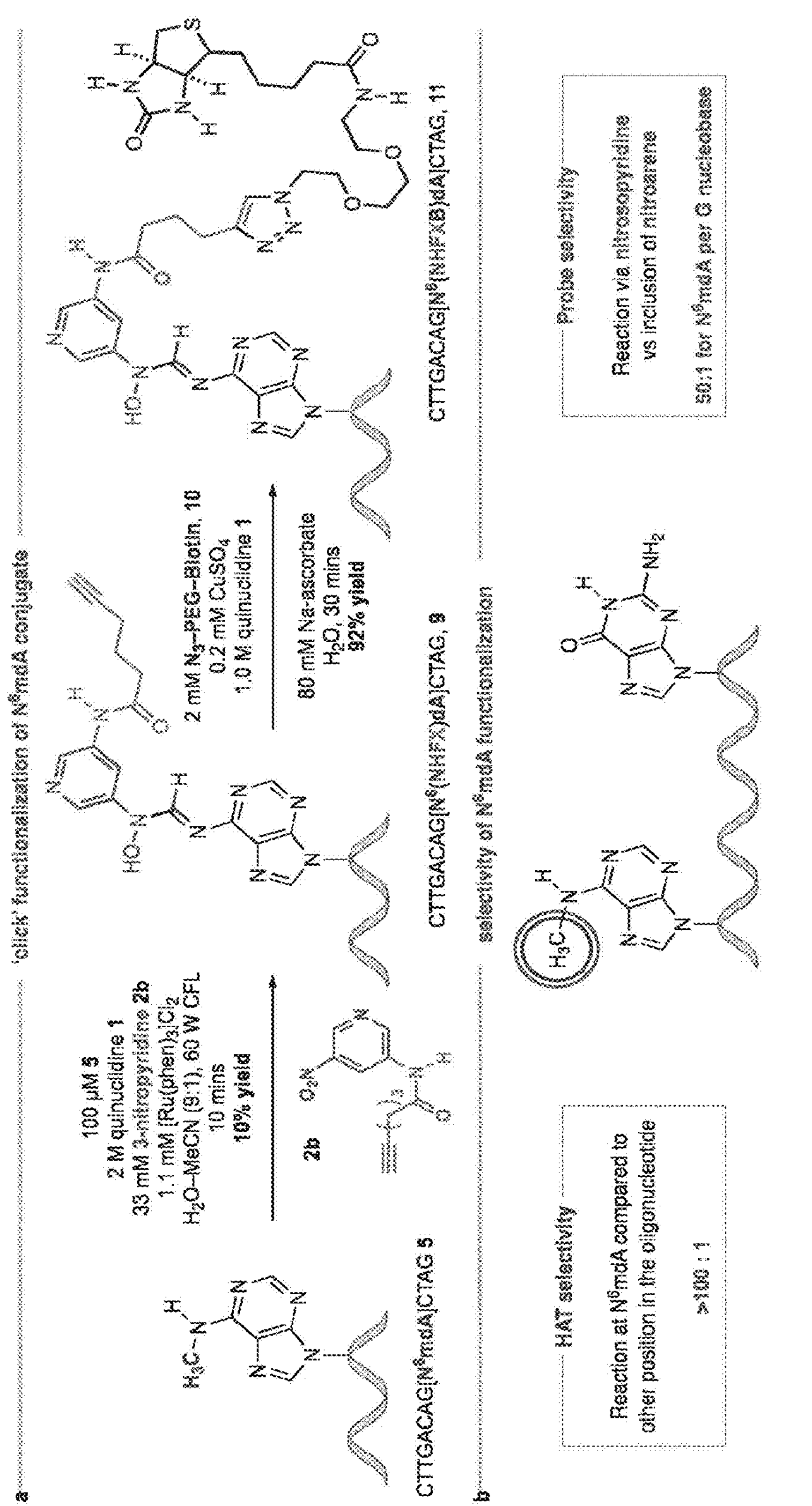
FIG. 4 shows the photoredox functionalization and downstream modification at $N^6$mdA in DNA. a) Shows the use of modular nitropyridine probes in oligonucleotide functionalization and subsequent elaboration by Huisgen cycloaddition. b) Shows selectivity parameters in the oligonucleotide functionalization are defined as 'HAA selectivity' (reflecting the position of C—H bond cleavage) and 'Probe selectivity' (reflecting the selectivity of reaction via nitrosopyridine vs nitropyridine).

Next, a latently reactive functionality capable of downstream elaboration was incorporated to tailored nucleic acid fragments. A design-augmentation process revealed an alkyne-containing, amide-linked nitropyridine 2b could be coupled with 5 upon treatment with the $Ru(phen)_3Cl_2$, quinuclidine and irradiation for 10 minutes (FIG. 4A), forming the desired alkyne-containing oligonucleotide 9.

It is notable that 2b is devoid of potentially competitive hydridic C—H bonds and the amide substituent does not seem to affect the oxidative reactivity of the 3-nitropyridine core. Exploiting the newly installed alkyne functionality, it was found that a 'click' Huisgen-cycloaddition between 9 and PEG3 biotin-derived azide 10 necessitated specific conditions for an effective reaction; a solution of copper sulfate and sodium ascorbate required the addition of quinuclidine (presumably to act as a ligand for the copper-catalyst) to facilitate cycloaddition to the biotin-conjugated oligonucleotide 11 with 92% conversion to product.

Reaction conditions and yields for the Huisgen cycloaddition of various alkyne-functionalized $N^6$mdA ODN with azide-$PEG_3$-biotin 10 are shown in Scheme 2 and Table 2. THTPA: Tris(benzyltriazolylmethyl)amine, TCEP: tris(2-carboxyethyl)phosphine, Na-asc.: sodium ascorbate.

Scheme 2

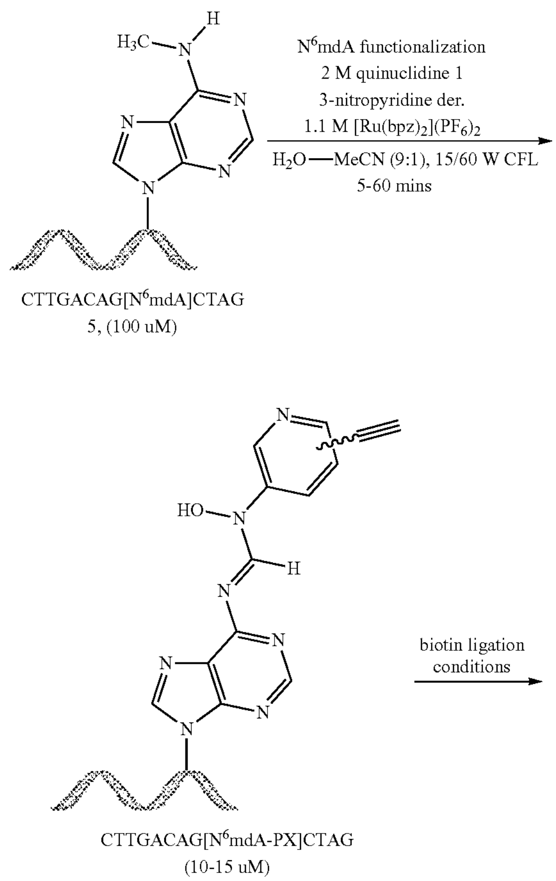

CTTGACAG[$N^6$mdA]CTAG
5, (100 uM)

CTTGACAG[$N^6$mdA-PX]CTAG
(10-15 uM)

-continued

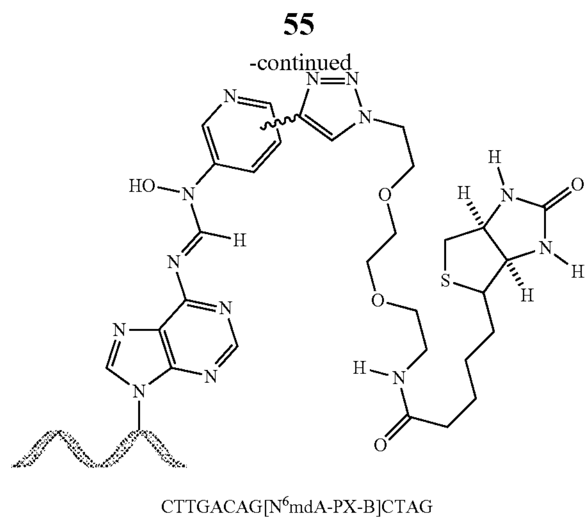

CTTGACAG[$N^6$mdA-PX-B]CTAG

Importantly, the photoredox transformation with 2b or other 3-nitropyridine alkyne-derivatives on an oligonucleotide without an $N^6$mdA residue (7) showed no conversion to product, indicating the transformation is selective for this feature (Scheme 3). Moreover, careful analysis of the mass spectral data acquired from this reaction revealed no detectable trace of a modification derived from the 3-nitrosopyridine unit at any nucleotide. In spite of the vast number of similar C—H bonds in 5, it is remarkable that the HAA step through which the methyl group of $N^6$mdA residues is functionalized is so exquisitely selective (termed 'HAA selectivity', reaction at $N^6$mAde compared to other position in a nucleic acid, >100:1). These results not only indicate an exquisite selectivity for the functionalization of $N^6$mdA, but also unambiguously confirm the position of the new label on the $N^6$ methyl group. Indeed, labeled oligonucleotide 7 would be detected if the HAA were to occur unselectively on deoxyribose moieties or any canonical nucleobase.

TABLE 2

| 3-Nitropyridine der. | [c] | Photoredox conditions[a] | Yield[b] [$N^6$mdA-P[X] (m/z $[M-3H]^{3-}$) | 'Click' conditions | Yield[b] [$N^6$mdA-PX-B] (m/z $[M-3H]^{3-}$) |
|---|---|---|---|---|---|
| 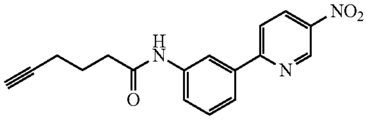 [SMILES: C#CCCCC(=O)Nc1cccc(-c2ccc([N+](=O)[O-])cn2)c1] | 0.04M | 1 h, 15 W CFL | 3.5% (1420) | 2 mM 10<br>0.2 mM $CuSO_4$<br>1 mM THPTA<br>0.8 mM TCEP<br>r.t., 1 h | not detected (1568) |
| 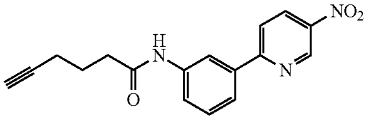 [SMILES: C#CCCCC(=O)Nc1cccc(-c2ccc([N+](=O)[O-])cn2)c1] | 0.04M | 1 h, 15 W CFL | 3.5% (1420) | 2 mM 10<br>0.2 mM CuBr<br>1 mM THPTA<br>r.t., 1 h | not detected (1568) |
| 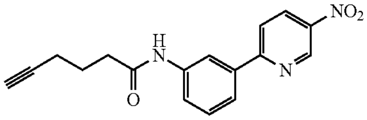 [SMILES: C#CCCCC(=O)Nc1cccc(-c2ccc([N+](=O)[O-])cn2)c1] | 0.04M | 1 h, 15 W CFL | 3.5% (1420) | 2 mM 10<br>0.2 mM $CuSO_4$<br>1 mM THPTA<br>0.8 mM Na-asc.<br>r.t., 1 h | 23% (1568) |
| 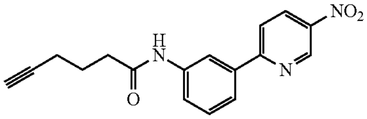 [SMILES: C#CCCCC(=O)Nc1cccc(-c2ccc([N+](=O)[O-])cn2)c1] | 0.04M | 1 h, 15 W CFL | 3.4% (1420) | 2 mM 10<br>0.2 mM $CuSO_4$<br>1M quinuclidine<br>0.8 mM Na-asc.<br>r.t., 1 h | 24% (1568) |
| 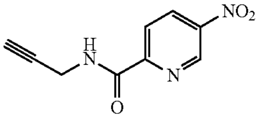 | 0.04M | 1 h, 15 W CFL | 8.0% (1385) | 2 mM 10<br>0.2 mM $CuSO_4$<br>1M quinuclidine<br>0.8 mM Na-asc.<br>r.t., 1 h | not detected (1533) |
| 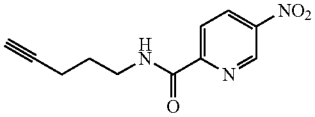 [SMILES: C#CCCCNC(=O)c1ccc([N+](=O)[O-])cn1] | 0.05M | 1 h, 15 W CFL | 6.6% (1394) | 2 mM 10<br>0.2 mM $CuSO_4$<br>1M quinuclidine<br>0.8 mM Na-asc.<br>r.t., 30 min | 88% (1542) |
| 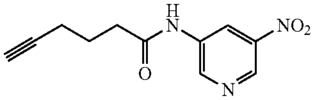 [SMILES: C#CCCCC(=O)Nc1cncc([N+](=O)[O-])c1] | 0.05M | 10 min, 60 W CFL | 10% (1394) | 2 mM 10<br>0.2 mM $CuSO_4$<br>1M quinuclidine<br>0.8 mM Na-asc.<br>r.t., 30 min | 92% (1542) |

[a]other reaction conditions according to General Procedure B

[b]assay yields by LCMS

[c][$N^6$mdA-Q] (ODN 6) species coeluting in LCMS, approximate yields according to MS signal intensities Scheme 3

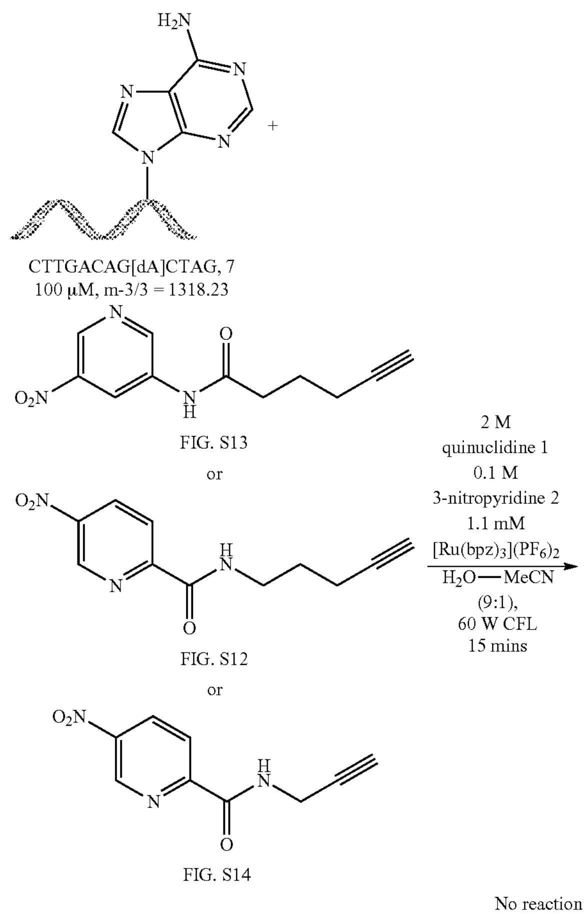

CTTGACAG[dA]CTAG, 7
100 μM, m-3/3 = 1318.23

No reaction

However, under the photoredox conditions with 2b, trace levels of oligonucleotides were detectable that had a mass ion reflecting the inclusion of an intact 3-nitropyridine (16 mass units higher than N-hydroxyformamidine-derived oligonucleotide 9). Although the structure of this trace-level, off-target modification was not elucidated, a series of control experiments revealed that the trace-level addition of 3-nitropyridine was taking place at G residues. The selectivity for the formation of the desired $N^6$mdA-derived N-hydroxyformamidine linkage compared to the inclusion of 3-nitropyridine at G was calculated as 50:1 for $N^6$mdA per G nucleobase (termed 'Probe selectivity', reaction via nitrosopyridine vs inclusion of nitroarene), a ratio which is, again, notably high.

Figure 5:
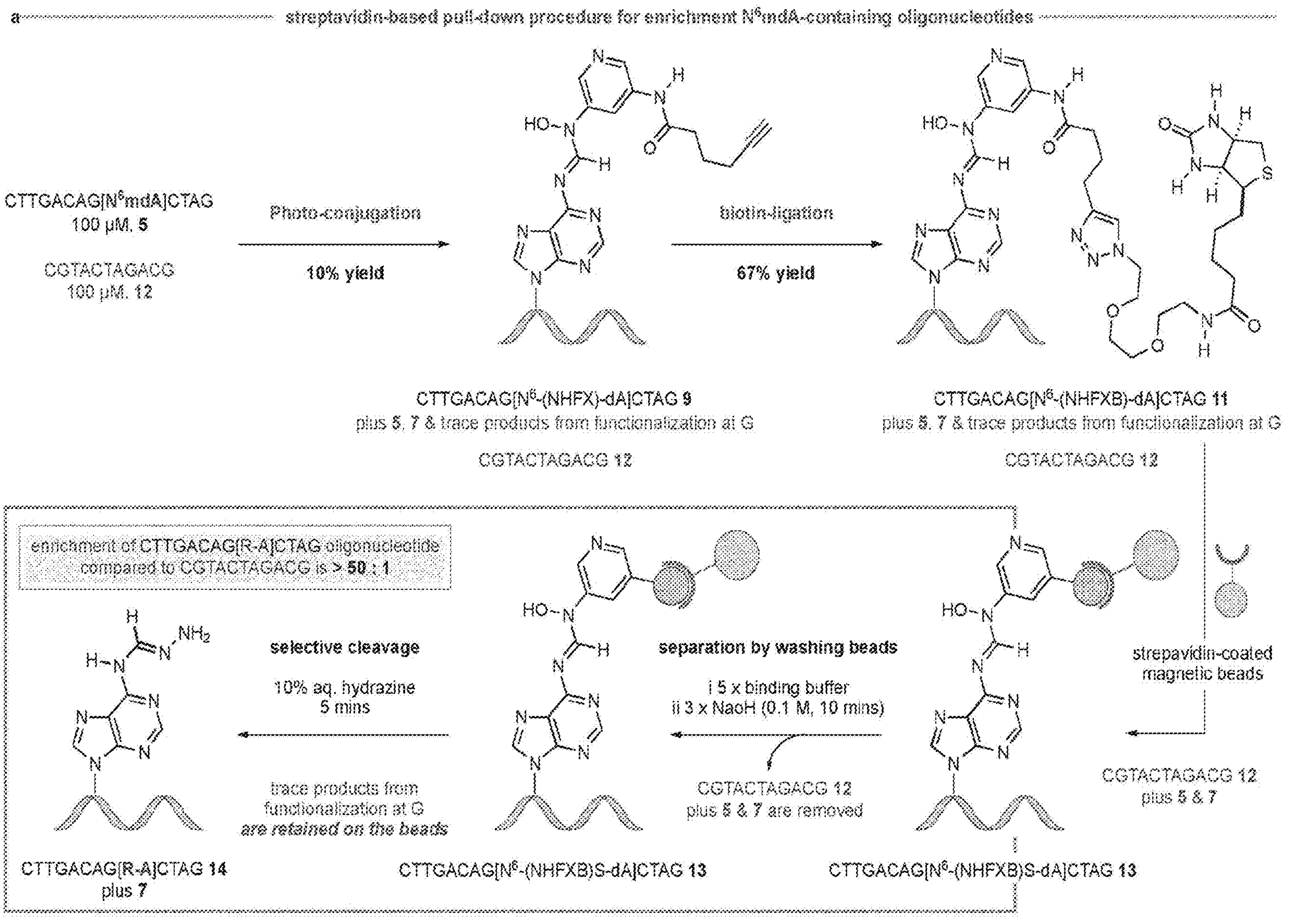
FIG. 5 shows a pull down procedure involving photoredox functionalization with an alkyne-derived nitropyridine, Huisgen cycloaddition with a biotin-derived azide, immobilization on streptavidin coated magnetic beads, oligonucleotide separation by sequential washing and selective cleavage of $N^6$mdA-derived oligonucleotides. The process delivers an enrichment of >50:1.

The versatile biochemical properties inherent to the biotin motif provide a means to isolate the modified $N^6$mdA-derived oligonucleotide from other nucleic acid fragments via a streptavidin-based pull-down procedure (immobilization, washing, cleavage and retrieval of the target oligonucleotide), which could enable the detection of $N^6$mdA-containing oligonucleotides in complex mixtures. Known methods for substrate retrieval from streptavidin pull-down protocols involve relatively harsh reaction conditions, which are designed to denature the protein scaffold. However, the present photoredox conjugation procedure installs the N-hydroxyformamidine linkage, a more labile functional group. Accordingly, we reasoned that significantly milder, nucleophile-mediated, cleavage conditions could be used in the retrieval of the labeled oligonucleotide. This is important because mass analysis of the photoredox reaction mixtures had suggested that the traces products arising from unselective functionalization at G do not contain an electrophilic N-hydroxyformamidine linkage. Consequently, it was speculated that these off-target products of functionalization at G could be retained on the streptavidin beads during cleavage, thereby enhancing the selectivity observed in the photoredox step and enrichment of the $N^6$mdA-derived oligonucleotide. Guided by this hypothesis, the photo-conjugation with oligonucleotide 5 and nitropyridine 2b was conducted in the presence of a distinct, but importantly non-methylated oligonucleotide CGTACTAGACG 12, as a means to test whether the method could be used to enrich $N^6$mdA-containing oligonucleotides within nucleic acid mixtures (FIG. 5A). The N-hydroxyformamidine product 9 was formed in 10% conversion and observed by LC-MS alongside unreacted 5, the demethylated oligonucleotide 7, the control oligonucleotide 12 and traces of the G-nitropyridine functionalized oligonucleotide (50:1 probe selectivity, $N^6$mdA/G).

The N-formamidine group follows a distinct hydrolysis process which provides two sets of hydrolysed products containing N-formyl derivatives (Vincent 1999). Given this unique feature, hydrolysis studies were conducted on the labeled oligonucleotide 9 to confirm the identity of the N-hydroxyformamidine structural linkage (Scheme 3). As expected, treatment of the reaction mixture acquired from the photoredox conjugation (containing product 9) with acetate buffer at pH=4.7 for 60 minutes provided three new products: N-formyl oligonucleotide 15, 3-N-hydroxypyridine derivative 16 and 3-N-formyl-N-hydroxypyridine derivative 17 (all the products were characterized by HRMS). Importantly, a control experiment where oligonucleotide 7 was subjected to the same procedure (photoredox and hydrolysis) did not result in formation of any of the hydrolysis products according to scans of calculated exact masses with error ranges of up to 100 ppm. Together, these results undoubtedly confirm the presence of an N-hydroxyformamidine linkage in the photoredox $N^6$mdA product.

Scheme 3

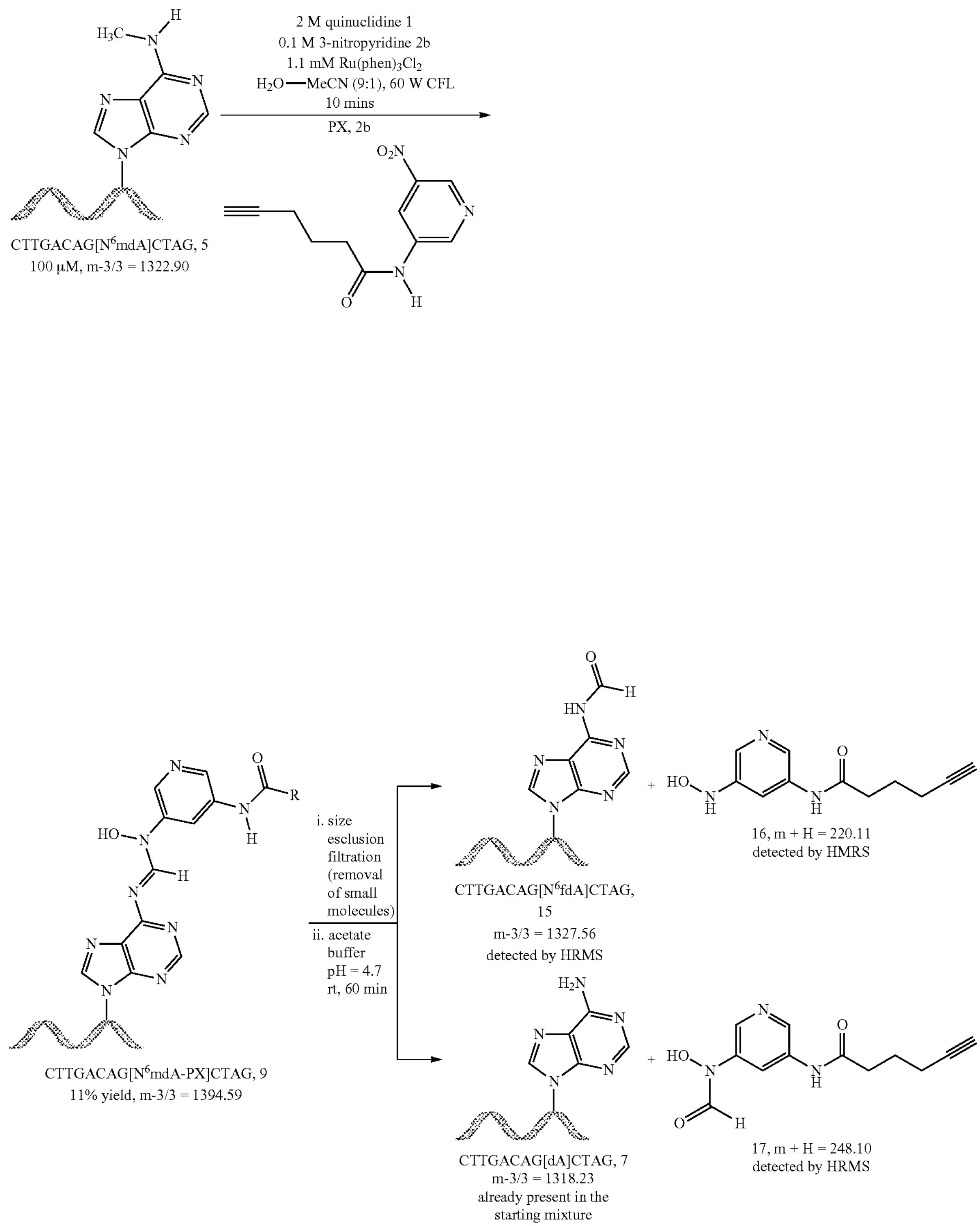

Additional evidence for the N-hydroxyformamidine linkage were provided by reactivity studies using hydrazine as nucleophile instead of water (Scheme 4). In this case, the corresponding N—$NH_2$ formamidine product 14 was detected by HRMS at the end of the pull-down procedure. Treatment of immobilized DNA fragment 13 with 10% hydrazine aqueous solution for 5 minutes delivered N—$NH_2$ formamidine product 14 along with small amount of 7 (due to the hydrolysis of 14). The formation of a new hydrazine product as well as its oxidation state (confirmed by its molecular mass) is a further proof for the identity of the N-hydroxyformamidine moiety.

Scheme 4

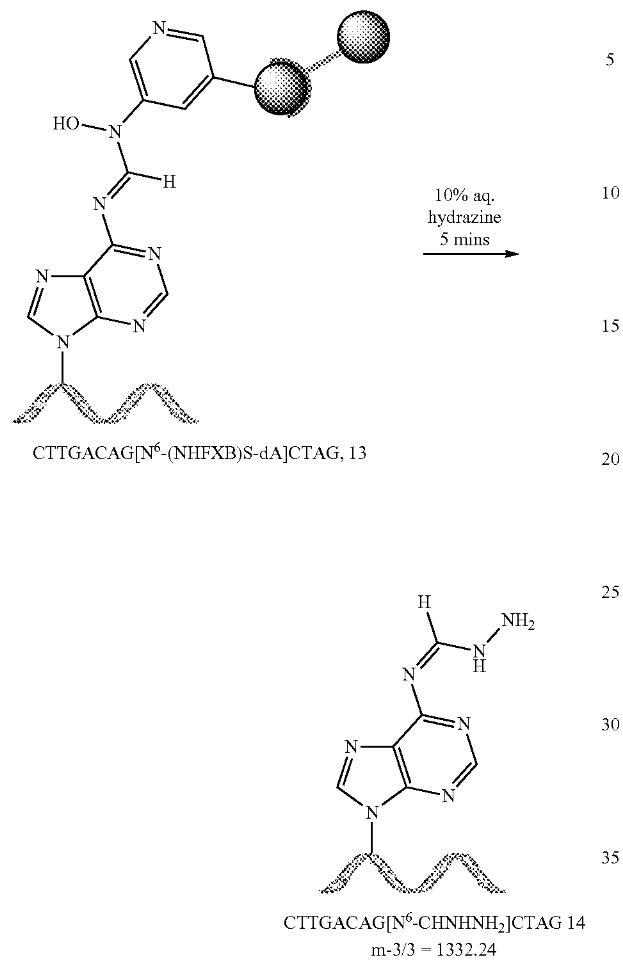

CTTGACAG[$N^6$-(NHFXB)S-dA]CTAG, 13

CTTGACAG[$N^6$-$CHNHNH_2$]CTAG 14
m-3/3 = 1332.24

Another indication of the presence of N-hydroxyformamidine is the detection of Ni(II) and Zn(II) adducts of product 9 and the corresponding click product 11 during HRMS and isotopic pattern studies (Scheme 5). Interestingly, Ni(II) and Zn(II) adducts are only visible for the oligonucleotides that contain an N-hydroxyformamidine moiety (9 and 11), in accordance to previous reports describing these particular moieties as good bidentate ligands (Krajete 2004: Cibian 2016).

Scheme 5

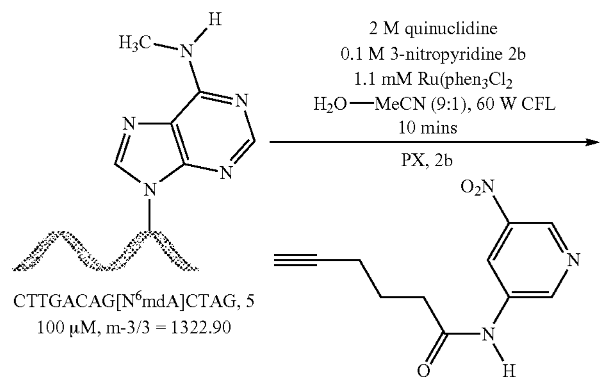

CTTGACAG[$N^6$mdA]CTAG, 5
100 μM, m-3/3 = 1322.90

-continued

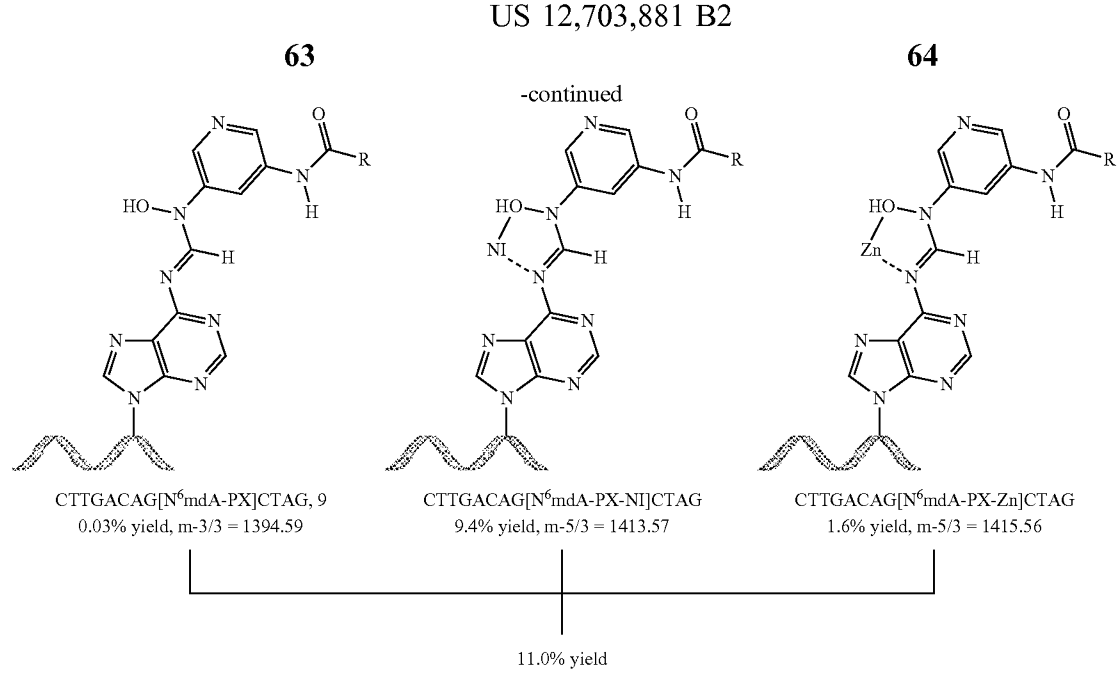

Cycloaddition of 9 with biotin-azide 10 afforded the selective N$^6$mdA biotin-conjugated oligonucleotide 11. Treatment of the oligonucleotide mixture with streptavidin-coated magnetic beads allowed immobilization of all the species containing biotin (13 plus trace levels of product arising from unselective reaction at G residues) and permitted the removal of unlabeled oligonucleotides via successive washing procedures. As noted above, it was found that the electrophilic nature of the N-hydroxyformamide linkage made it susceptible to reaction with aqueous hydrazine and led to the release of an N6-(hydrazonomethyl)dA-containing oligonucleotide 14 with a small amount of 7 (arising from the hydrolysis of 14) and trace quantities of the other oligonucleotides that had been indiscriminately retained by the streptavidin-coated beads. The recovery of both 14 and 7 provides direct evidence for the presence of N$^6$mdA in the starting sequence and their ratio to all other oligonucleotides gives rise to an enrichment greater than 50:1. It is particularly important to note that the maximum theoretical enrichment value that can be obtained as a result of the observed photoredox probe selectivity is -17:1, since oligonucleotide 14 contains three G residues (probe selectivity of 50:1 N$^6$mdA per G residue). Therefore, the observed enrichment of >50:1 clearly demonstrates that the hydrazine cleavage procedure is selective for N-hydroxyformamidine linkage in the N$^6$mdA-derived oligonucleotide conjugates versus products of reaction at G (that are presumably retained on the beads), leading to the observed enhanced enrichment.

The N$^6$mdA-selective oligonucleotide functionalization and enrichment protocol was further demonstrated on longer single-stranded (ss) DNA fragments. Now using quantitative PCR (qPCR) to analyse the enriched fractions and determine the amplifiable amount of both initially methylated and unmethylated DNA sequences after the pull-down, it was found that the photoredox-based functionalization protocol enriched the N$^6$mdA-containing oligonucleotide from a mixture of two 99-nucleotide ssDNA fragments with an enrichment of 6.4:1 (FIG. 6, experiment i, wherein the upper strand is the N$^6$mdA-containing oligonucleotide). Importantly, a parallel experiment ii in FIG. 6 using the same nucleic acid sequences but having the N$^6$mdA residue in the other (lower) sequence showed a similar level of enrichment. These results confirm that N$^6$mdA is required for the enrichment and highlights that the observed enrichment is not dependent of the used DNA sequences.

Figure 6:
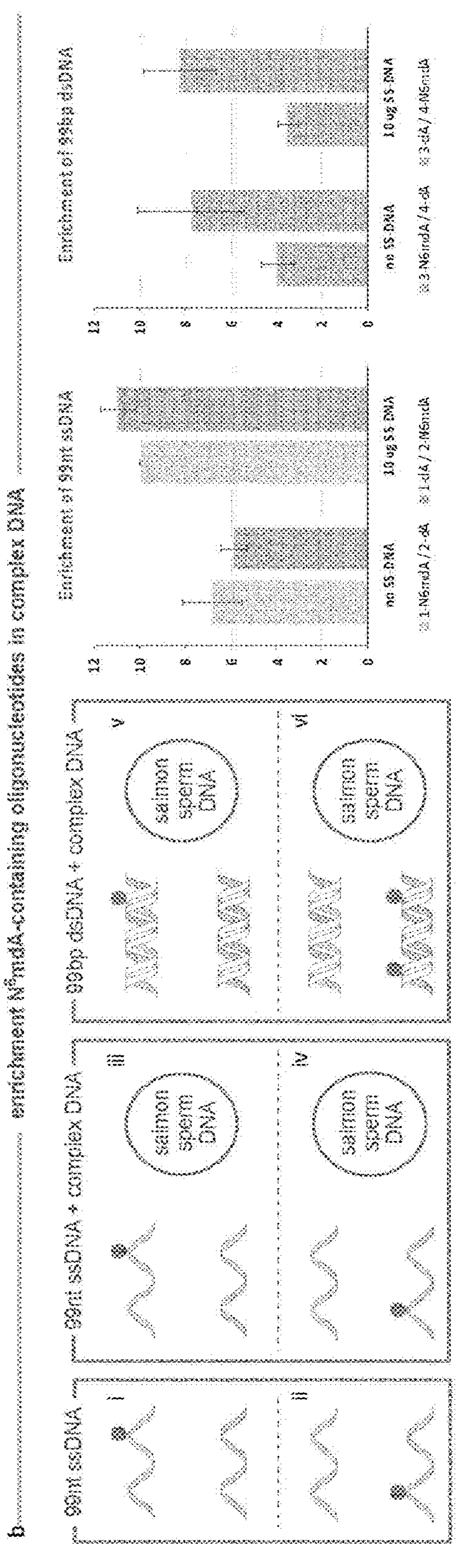
FIG. 6 shows the results of pull down experiments using 99 nt ssDNA and 99 bp dsDNA in the presence and absence of salmon sperm (SS) DNA. This demonstrates enrichment in complex mixtures of DNA sequences. Filled dot indicates an $N^6$mdA residue.

To simulate the complex matrix of a cellular DNA sample, where the concentration of N$^6$mdA with respect to dA will be very low, the ssDNA fragments was combined with a 10-fold excess of salmon sperm DNA, to create mixtures with N6mdA/dA ratios of 1:383 (0.26%). Applying the photo-conjugation and pull-down procedure to these samples, the results in FIG. 6 show that the N$^6$mdA-containing ssDNA fragments were enriched to levels of approximately 10.5:1 (experiments iii & iv in FIG. 6) compared to experiments in the absence of the salmon sperm DNA (~6.4:1, experiments i & ii in FIG. 6).

In double stranded DNA, the methyl group of N$^6$mdA is thought to project into the major groove of double stranded helix, providing an additional challenge for the photoredox functionalization of complex nucleic acid samples due to potentially adverse steric and electronic effects that arise from the local chemical environment. Despite this congestion, it was found that on applying the sequential photoredox conjugation, click reaction and pull-down procedure to a mixture of N$^6$mdA-containing 99 base pair dsDNA and a non-methylated double stranded fragment that had been combined with salmon sperm DNA (N$^6$mdA/dA ratio is 1:3433, 0.03%), the N$^6$mdA-containing DNA sequence was recovered with an enrichment of 4:1 (experiment v in FIG. 6, wherein the upper stand is the N$^6$mdA-containing dsDNA). It is important to note that the theoretical probe selectivity should be 1:1 (on the basis of the dsDNA fragment containing 50 G residues). A parallel experiment vi in FIG. 6 using the same nucleic acid sequences but having two N$^6$mdA residues in the second template (lower dsDNA strand; N$^6$mdA/dA ratio is 1:1717, 0.06%) showed an increased enrichment of 8:1 for the N$^6$mdA-derived oligonucleotide, indicating a positive cumulative effect (FIG. 6).

Taken together, this set of experiments demonstrates the applicability of the developed chemistry on longer ssDNA, dsDNA, as well as in complex samples with excess DNA, providing a proof of concept for the enrichment of N$^6$mdA-DNA strands and showcasing the potential for future application in mapping this underexplored methylated nucleotide.

While the cell's biochemical machinery is capable of regulating the methylation state of A in nucleic acids, we have developed a selective chemical transformation that generates and intercepts an 'on-DNA' α-amino radical to form a stable covalent modification at $N^6$mdA residues. Orchestrated by a visible light-activated photoredox catalyst, a polarity-matched hydrogen atom abstraction step at the N6-methyl group of $N^6$mdA generates an α-amino radical and dovetails with a distinct, in situ, reaction to form a nitrosopyridine spin trapping reagent, which together lead to radical cross coupling process that introduces a modular functional handle into oligonucleotide sequences. Importantly, this strategy provides a basic technology upon which a chemical method for locating $N^6$mdA in genomic DNA can be founded, potentially leading to sequencing methods that will further unravel the role of this epigenetic modification and should also be amenable to targeting methylated nucleobases in the many forms of RNA that regulate cellular function.

The same strategy can be used to functionalize $N^6$ mA residues in RNA. An RNA oligonucleotide containing $N^6$ mA is functionalized using the photoredox reaction in Scheme 6.

Scheme 6

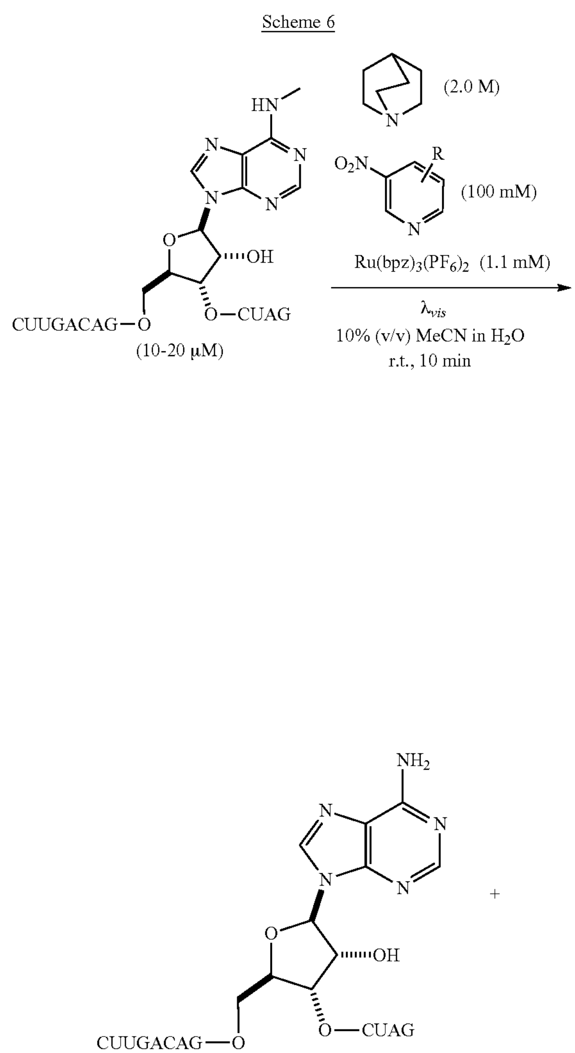

-continued

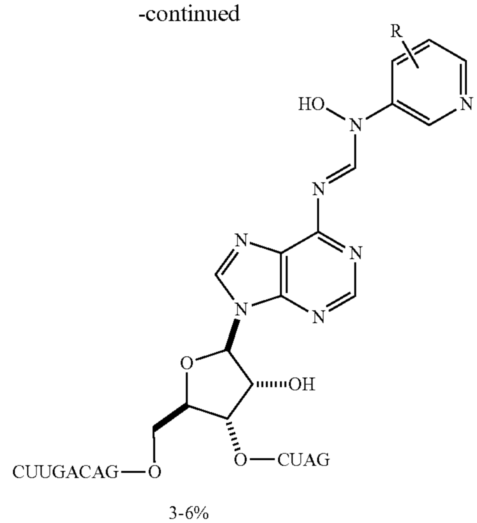

Improvement of the Photoredox Reaction Outcomes with Ac-Dha-Me

Figure 7:
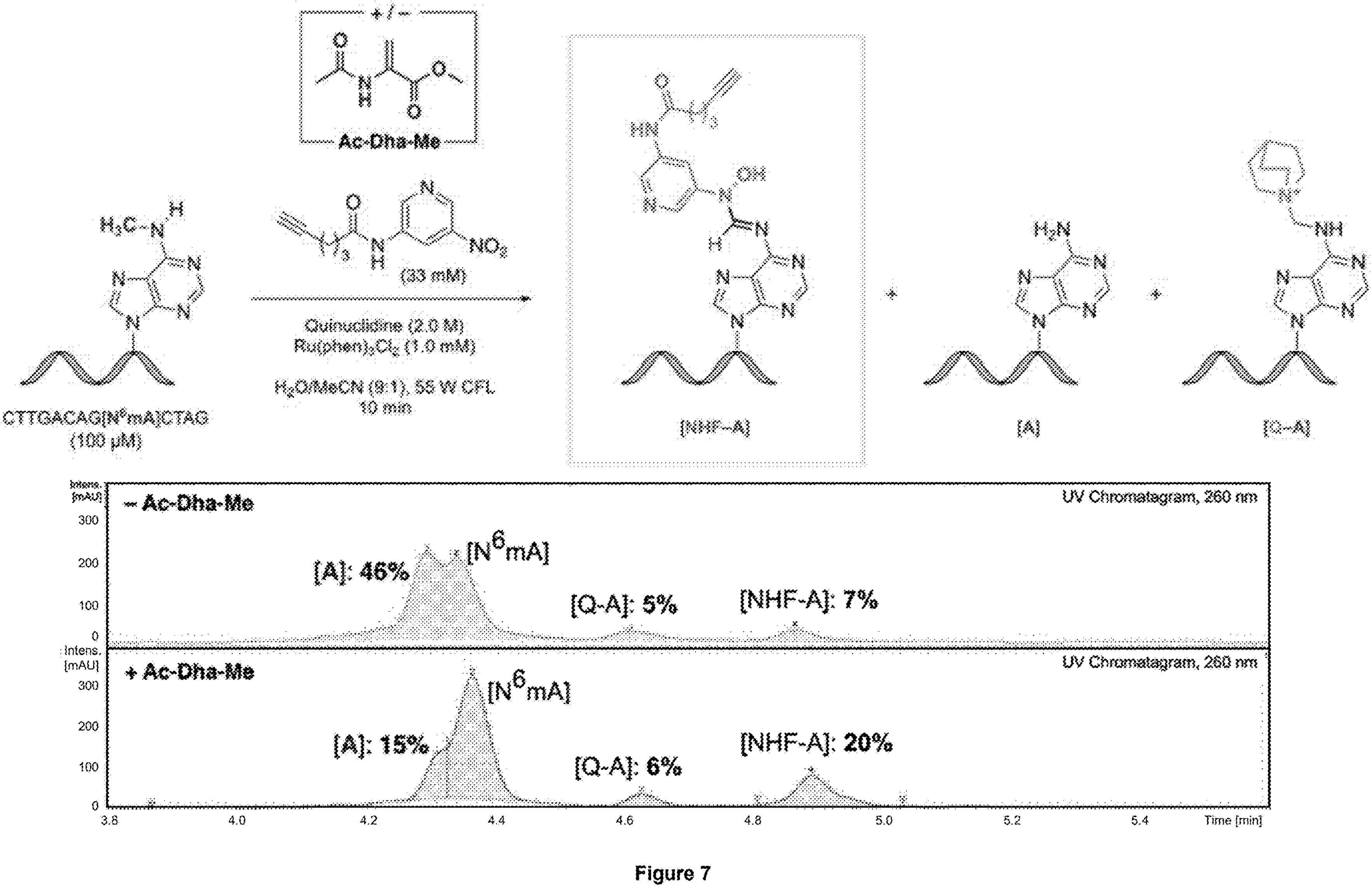
FIG. 7 shows that the presence of N-acetyl dehydroalanine methyl ester (Ac-Dha-Me, 8 mM) in the photoredox reaction results in the decreased demethylation of $N^6$ mA (to form [A]) and increased selective formation of the N-hydroxyformamidine derivative [NHF-A].

The use of different activated alkenes as additives in the photoredox reaction was investigated. It was found that the presence of N-acetyl dehydroalanine methyl ester (Ac-Dha-Me) resulted in slightly elevated yields for the N-hydroxyformamidine (NHF) formation (15-20% versus 6-13% (LCMS) for the reaction with the alkynylated 3-nitropyridine probe performed on the short model oligonucleotide 5; FIG. 7).

Figure 8:
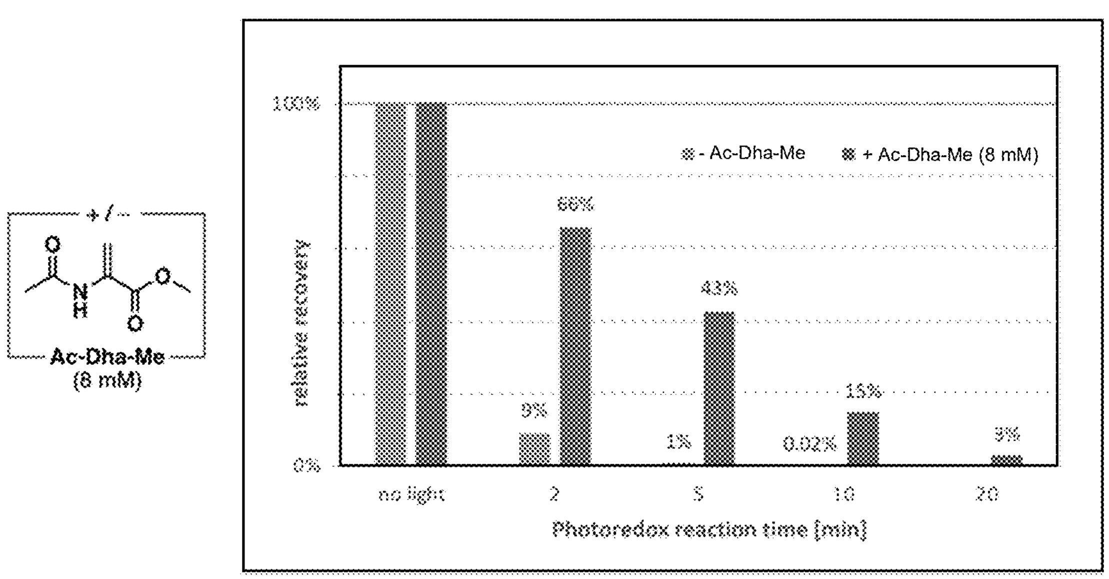
FIG. 8 shows the recovery of a 99 base-pair double stranded DNA sequence (quantified by qPCR) after different irradiation times and in the presence and absence of N-acetyl dehydroalanine methyl ester (Ac-Dha-Me, 8 mM). The results confirm that the presence of Ac-Dha-Me diminishes decomposition of oligonucleotides during the photoredox reaction to functionalise $N^6$ mA.

Analysis of the photoredox reaction in the presence of Ac-Dha-Me on longer oligonucleotide substrates further indicated that in addition to ablatively higher yields, trace side reactions and decomposition of the substrate oligonucleotides could be diminished. This observation was confirmed by quantifying recovery of a 99 base pair (bp) double stranded (ds) DNA substrate upon photoredox reactions with different irradiation times (FIG. 8).

'On-Bead' Primer Extension on Short Model Oligonucleotides

The use of the photoredox labeling reaction to map the location of a $N^6$mAde site within a nucleotide was investigated. We reasoned that the labelling reaction could include a polymerase stop event in a primer extensions reaction, resulting in a truncated nucleotide ending immediately before the $N^6$mAde site. However, such a method is challenging because the relative instability of the NHF linkage and the insufficient bulkiness of the chemical moiety attached on $N^6$mAde may give rise to uninterrupted polymerase read through. Accordingly, we decided to proceed with the biotinylation of $N^6$mAde as previously described and immobilize the functionalized oligonucleotides on streptavidin-coated magnetic particles. Not only had we previously observed that the streptavidin-bound $N^6$mAde-biotin-NHF was more stable, but the tight interaction with streptavidin was also reasoned to prevent polymerase read-through at the site of interest. Moreover, the possibility to combine enrichment and polymerase stop was reasoned to considerably increase sensitivity in envisaged genome-wide base resolution $N^6$ mA mapping applications.

Figure 9:
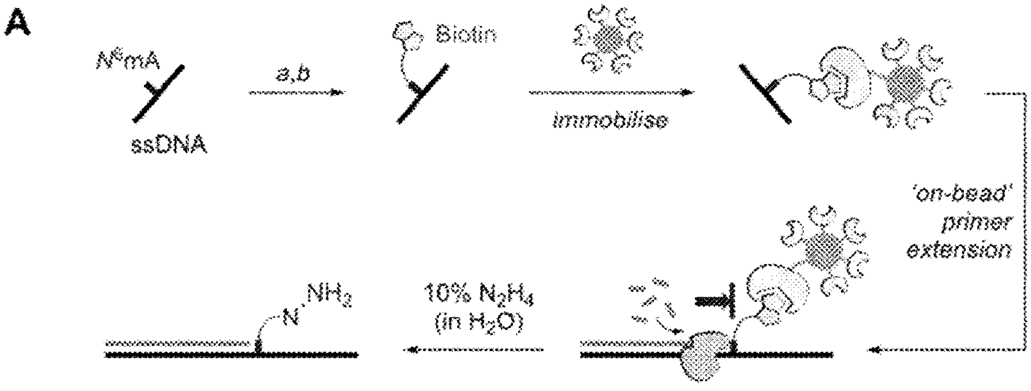
FIG. 9 A) provides an overview of the workflow to test polymerase stalling after selective chemical biotinylation of synthetic oligodeoxynucleotides at $N^6$ mA moieties and immobilization on streptavidin-coated magnetic beads. B) shows an LC-MS analysis confirming the presence of one major and two minor polymerase stalling products.
Figure 9:
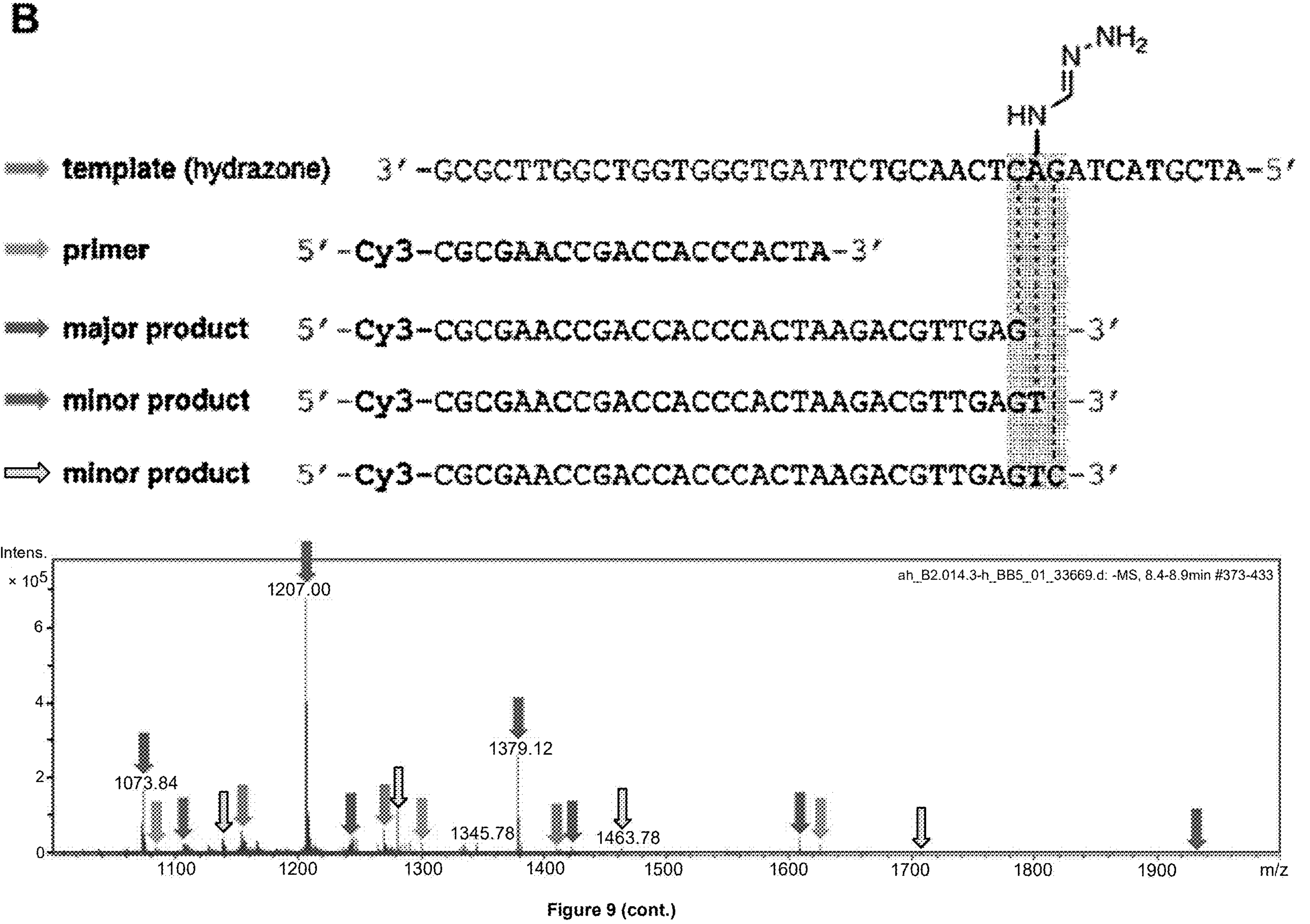

Initial experiments with a 41 nt ssDNA sequence yielded promising results (FIG. 9). Upon biotinylation at $N^6$mAde and immobilisation on streptavidin-coated magnetic beads, treatment with a primer, nucleoside triphosphates and Klenow Fragment (3'-5' exo-) at 37° C. over 20 min resulted in a clearly discernible polymerase stalling product occurring together with fully elongated primer. LCMS analysis of the product indicated that the major product was due to polymerase stalling just before incorporation of the nucleotide opposite to the functionalised $N^6$ mA (position −1). Two minor products arose from stalling after incorporation at position 0 (opposite to the site of functionalisation) and +1.

Figure 10:
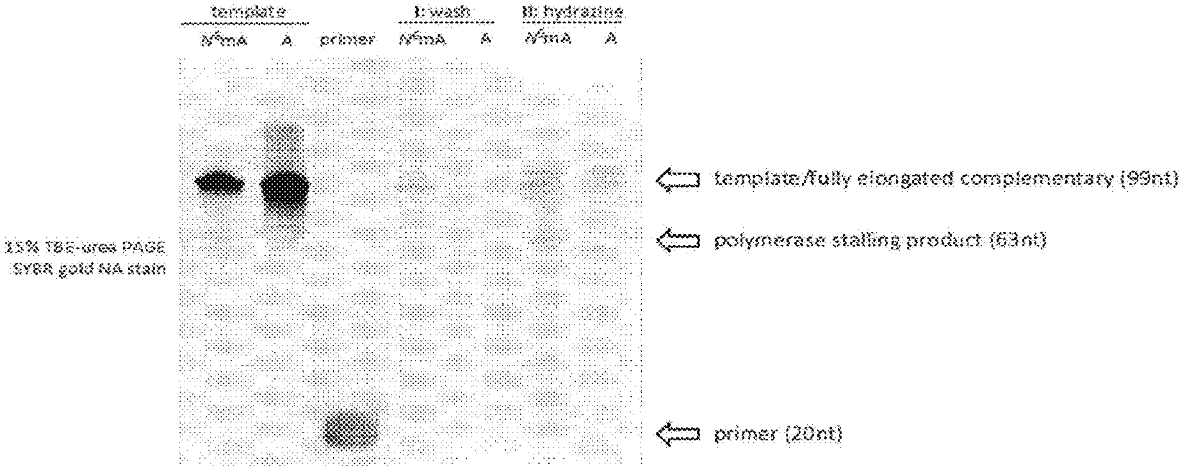
FIG. 10 shows polyacrylamide gel electrophoresis (PAGE) of products of 'on-bead' polymerase stalling experiments, clearly demonstrating an $N^6$ mA-dependent occurrence of the polymerase stalling product.

Polymerase stalling events could also be observed on longer (99 nt) ssDNA, using denaturing polyacrylamide gel electrophoresis (PAGE). FIG. 10 shows a distinct polymerase stop signal for the oligonucleotide containing $N^6$mAde, while no band was visible for the same sequence without methylation. Densitometric analysis on different gels from various experiments allowed an estimate of polymerase stalling efficiency as 30-50%. It is not yet known if the partial read-through of the polymerase can happen on the immobilised template or if it is not due to cleavage of the NHF bond preceding full primer extension. Nevertheless, it is visible in the gel image in FIG. 10 that both the full-length and stalling product were mainly recovered upon nucleophilic cleavage of the NHF bond, and not by a simple wash with buffer, indicating that read-through of the polymerase happens on immobilised template rather than after a NHF bond cleavage.

Figure 11:
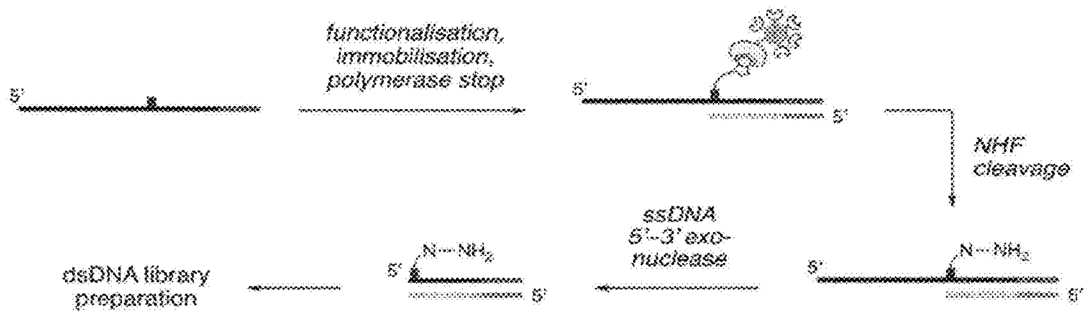
FIG. 11 provides a schematic overview of the strategy for the generation of DNA libraries for sequencing to map $N^6$ mA at base-resolution with the developed 'on-bead' polymerase stop approach.

Towards Base-Resolution Mapping of $N^6$ mA with the 'On-Bead' Polymerase Stop Approach With evidence for an 'on-bead' polymerase stop in hand, a final step towards a method to map $N^6$mAde was to establish a dsDNA library preparation workflow that would allow to read out $N^6$mAde occurrence by next-generation sequencing. The most straightforward approach was deemed to be to generate truncated dsDNA strands by selectively digesting ssDNA after NHF cleavage, using an ssDNA-specific 5'-3'exonuclease such as RecJf. With the obtained, blunt-end dsDNA fragments, one could then proceed to a standard dsDNA library preparation, as depicted in FIG. 11.

Figure 12:
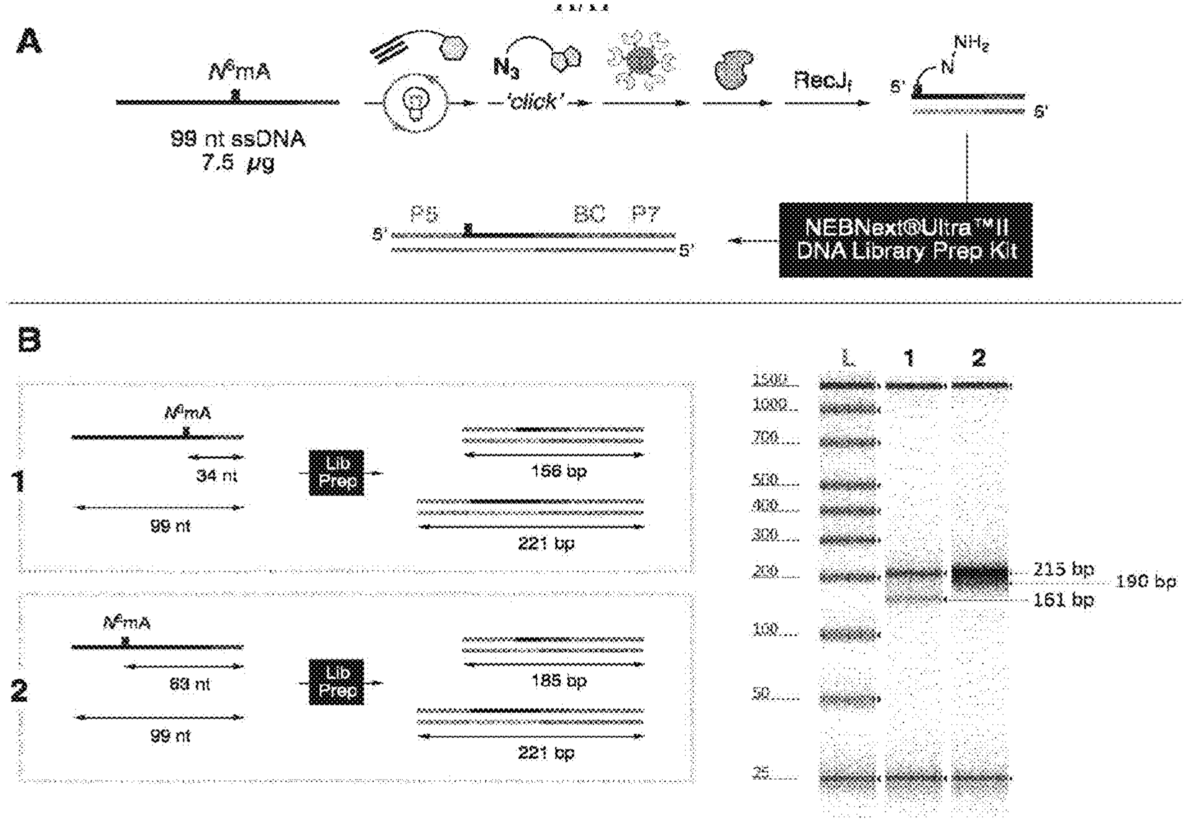
FIG. 12 A) shows the approach for the generation of DNA libraries to map $N^6$ mA from 7.5 μg synthetic 99 nt ssDNA. B) TapeStation analysis of the obtained libraries.

In a first attempt to test this approach, 7.5 μg of two different 99 nt ssDNA oligonucleotides featuring one $N^6$mAde base at different positions and a primer region at the 3'-end to be used in the 'on-bead' primer extension reaction were used (FIG. 12A). With some of the recovered material after the $RecJ_f$ digestion (40 ng, respectively), a standard NEBNext® Ultra™ II DNA library preparation was performed. The purification steps after adaptor ligation and final amplification were run without size selection according to the manufacturers protocol with 0.9×NEB purification beads.

Excitingly, analysis by TapeStation of the amplified and purified libraries showed two main bands (FIG. 12B); one corresponding to the expected full-length fragment (221 bp, from the initial 99 nt sequence plus ligated adaptors) and one corresponding to an initial fragment (156 bp and 185 bp, respectively, from 34 nt and 63 nt fragments plus ligated adaptors) with the expected length for a successful polymerase stalling at the initial NemA site. This indicated that sequencing of these libraries and identification of sharp drops of the sequence coverage in the output data would allow to detect $N^6$mAde occurrence at base resolution.

Figure 13:
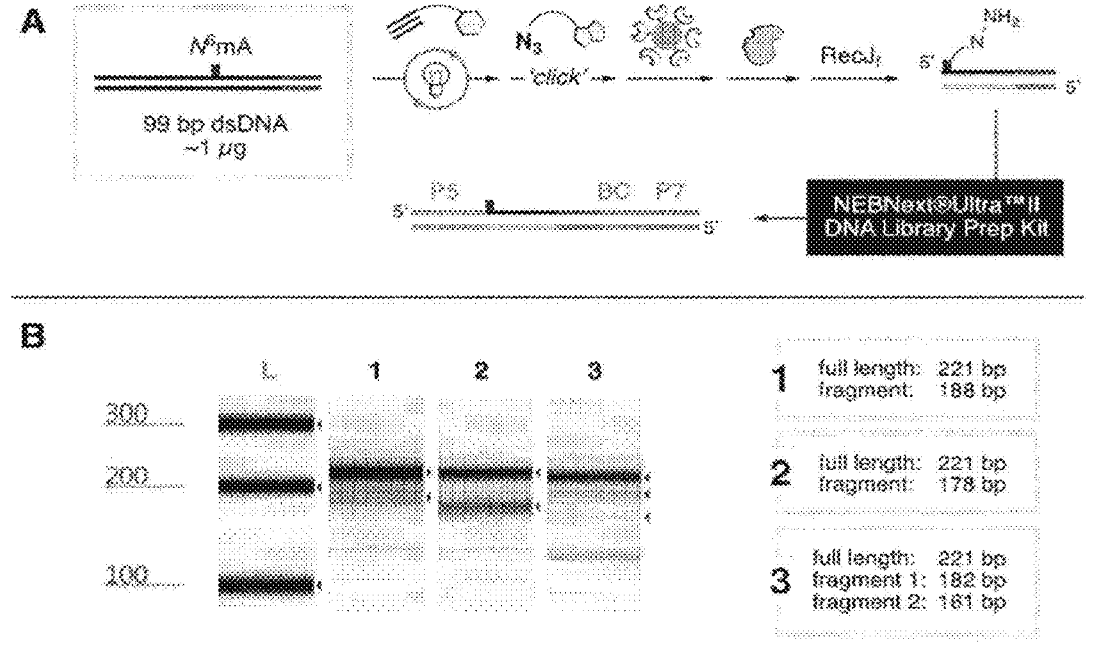
FIG. 13 A) shows the approach for the generation of DNA libraries to map $N^6$ mA from 1 μg synthetic 99 bp dsDNA. B) TapeStation analysis of the obtained libraries.

To confirm that the protocol would also be applicable on smaller samples and dsDNA, 1 μg of three different synthetic 99 bp dsDNA, all containing one or two NemA base at different positions were subjected to the same protocol (FIG. 13A). For the sequencing library preparation, 1 ng of the DNA recovered after the $RecJ_f$ digestion was used. Further optimisation of the purification steps during the library preparation were required, since the gradual dsDNA length cut-off when using 0.9×NEB purification beads resulted in partial loss of the shorter fragments. Purification using spin columns with a sharp cut-off of 25 bp (GeneJET PCR purification kit) resulted in slightly impure libraries according to TapeStation analysis (with an additional band around 120 bp, possibly due to amplification of primer dimers). Excitingly, analysis by TapeStation also showed expected fragments due to polymerase stalling at initial NemA positions (FIG. 13B), confirming that similar results can be obtained when starting from 1 μg dsDNA samples.

REFERENCES

All documents mentioned in this specification are incorporated herein by reference in their entirety.

Blanksby, S. J. et al. *Acc. Chem. Res.* 36, 255-263 (2003).
Cibian M. et al. *Eur. J. Inorg. Chem.* 177-185 (2016).
Dombrowski, G. W. et al. *J. Org. Chem.* 64, 427-431 (1999).
Douviataniotis, K. et al. *Science Advances* 6, eaay3335 (2020).
Gomez-Mejiba, S. E. et al. *Free Radic. Biol. Med.* 46, 853-865 (2009).
Jeffrey, J. L. et al. *Science* 349, 1532-1536 (2015).
Krajete, A. et al. *Eur. J. Inorg. Chem.* 1740-1752 (2004).
Lentini, A. et al. *Nat. Methods* 15, 499-504 (2018).
Liu, W.-Z. et al. *J. Org. Chem.* 61, 4778-4783 (1996).
O'Brown, Z. K. et al. *BMC Genomics* 20, 445-459 (2019).
Roberts, B. P. *Chem. Soc. Rev.* 28, 25-35 (1999).
Sánchez-Romero, M. A. et al. *Curr. Opin. Microbiol.* 25, 9-16 (2015).
Schübeler, D. *Nature* 517, 321-326 (2015).
Vincent, S. et al. *J. Org. Chem.* 64, 991-997 (1999).

The invention claimed is:

1. A method for labeling a nucleic acid comprising N6-methyl adenine ($N^6$mAde), the method comprising:

i) forming an alpha-amino radical on the N6-methyl group of $N^6$mAde; and ii) capturing the alpha-amino radical with a radical acceptor comprising a nitrosopyridyl group (O═N-Py-).

2. The method of claim 1, wherein the alpha-amino radical is formed by contacting the nucleic acid comprising $N^6$mAde with an amine-centered radical cation to abstract a hydrogen atom from the N6-methyl group of $N^6$mAde.

3. The method of claim 2, comprising oxidizing an amine to generate the amine-centered radical cation.

4. The method of claim 3, wherein the amine is a tertiary amine having the formula:

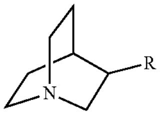

where R is selected from a hydrogen atom, a hydroxyl group, a $C_{1-6}$ alkyl group, a $C_{1-6}$ alkoxy group, a $C_{1-6}$ acyloxy group, a $C_{1-6}$ reverse ester group or a group —C(OH)$R^1R^2$, wherein $R^1$ and $R^2$ are each selected from $C_{1-6}$ alkyl.

5. The method of claim 3, wherein a photocatalyst is used to oxidize the amine, optionally wherein the photocatalyst, in either the excited state or reduced form, has a reduction potential of at least +1.10 volts (V) vs saturated calomel electrode (SCE) to at most +1.45 V vs SCE.

6. The method of claim 5, wherein the photocatalyst is a transition metal photocatalyst.

7. The method of claim 1, wherein the radical acceptor is a probe having the formula (I):

$$O{=}N{-}Py{-}L{-}X \quad (I)$$

where -Py- is a pyridinediyl group, -L- is a linker and —X is a label.

8. The method of claim 7, wherein -L- is:

$$—L^1—L^2—L^3—$$

where:

-$L^1$- is selected from a covalent bond or a $C_{6-10}$ arylene group;

-$L^2$- is selected from an amide linkage, an ester linkage, a carbonyl linkage, an amine linkage, or an ether linkage; and -$L^3$- is selected from $C_{1-10}$ alkylene and $C_{1-10}$ heteroalkylene.

9. The method of claim 7, wherein —X is a click reaction partner (—$C^1$) selected from the group consisting of $C_{2-20}$ alkynyl, $C_{2-20}$ alkenyl, isocyanide, azido, nitrone, nitrile oxide and tetrazine.

10. The method of claim 8, wherein the probe is formed insitu from a precursor having the formula (II):

$$O_2N{-}Py{-}L{-}X \quad (II)$$

where -Py- is a pyridinediyl group, -L- is a linker and —X is a label.

11. The method of claim 10, wherein the precursor is selected from compounds of formula P1 to P7:

(P1)

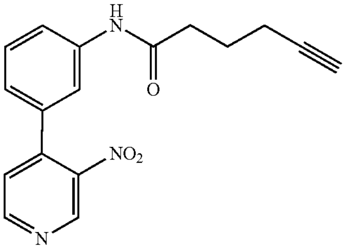

(P2)

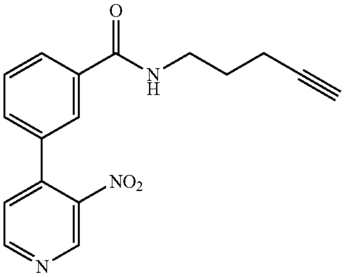

(P3)

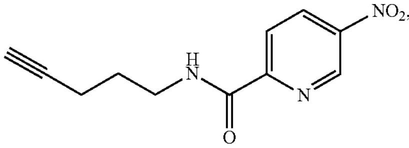

(P4)

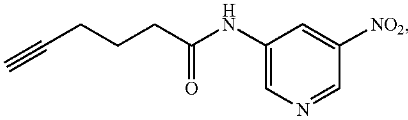

(P5)

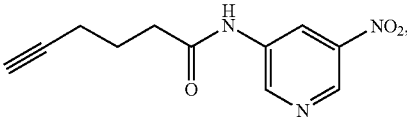

(P6)

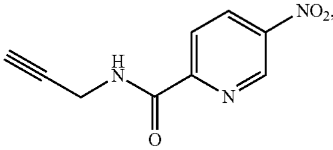

(P7)

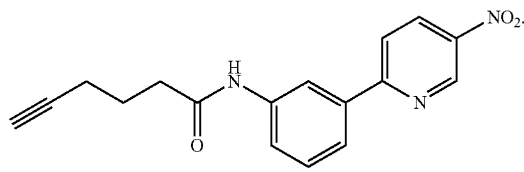

12. The method of claim 10, wherein the probe is formed by reducing the precursor of formula (II).

13. The method of claim 12, wherein a photocatalyst is used to reduce the precursor of formula (II).

14. The method of claim 7, wherein the method further comprises:

iii) contacting the nucleic acid with a bifunctional probe having the formula:

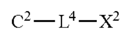

where —$C^2$ is a complementary click reaction partner, -$L^4$- is a linker and —$X^2$ is a label, wherein the bifunctional probe covalently binds to the nucleic acid.

15. The method of claim 14, wherein:

(i) —$C^2$ is an azido group (—$N_3$); or (ii) the linker -$L^4$- is:

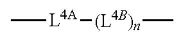

where:

-$L^{4A}$- is $C_{1-4}$ alkylene;

-$L^{4B}$- is $C_{1-4}$ heteroalkylene; and n is 0 to 8.

16. The method of claim 14, wherein —$X^2$ is an isolation label (—$X_{Iso}$) that binds to a binding agent, wherein the isolation label (—$X_{Iso}$) is biotin.

* * * * *